United States Patent
Chen

(10) Patent No.: US 8,324,369 B2
(45) Date of Patent: Dec. 4, 2012

(54) DENDRITIC CELL VACCINE COMPOSITIONS AND USES OF SAME

(75) Inventor: Si-Yi Chen, Pasadena, CA (US)

(73) Assignee: Baylor College of Medicine, Houston, TX (US)

( * ) Notice: Subject to any disclaimer, the term of this patent is extended or adjusted under 35 U.S.C. 154(b) by 42 days.

(21) Appl. No.: 12/744,651

(22) PCT Filed: Nov. 26, 2008

(86) PCT No.: PCT/US2008/084916
§ 371 (c)(1),
(2), (4) Date: May 25, 2010

(87) PCT Pub. No.: WO2009/082593
PCT Pub. Date: Jul. 2, 2009

(65) Prior Publication Data
US 2010/0255023 A1   Oct. 7, 2010

Related U.S. Application Data

(60) Provisional application No. 60/991,478, filed on Nov. 30, 2007.

(51) Int. Cl.
*C07H 21/04* (2006.01)
(52) U.S. Cl. .......... 536/24.5; 536/24.31; 536/24.1; 435/6; 435/325; 435/375; 514/44
(58) Field of Classification Search .......... None
See application file for complete search history.

(56) References Cited

U.S. PATENT DOCUMENTS

| | | | |
|---|---|---|---|
| 4,082,735 A | 4/1978 | Jones et al. | |
| 4,082,736 A | 4/1978 | Jones et al. | |
| 4,101,536 A | 7/1978 | Yamamura et al. | |
| 4,185,089 A | 1/1980 | Derrien et al. | |
| 4,235,771 A | 11/1980 | Adam et al. | |
| 4,406,890 A | 9/1983 | Tarcsay et al. | |
| 4,606,918 A | 8/1986 | Allison et al. | |
| 4,683,202 A | 7/1987 | Mullis et al. | |
| 4,962,091 A | 10/1990 | Eppstein et al. | |
| 5,023,243 A | 6/1991 | Tullis et al. | |
| 5,168,053 A | 12/1992 | Altman et al. | |
| 5,190,931 A | 3/1993 | Inouye | |
| 5,199,942 A | 4/1993 | Gillis et al. | |
| 5,350,674 A | 9/1994 | Boenisch et al. | |
| 5,580,859 A | 12/1996 | Felgner et al. | |
| 5,585,362 A | 12/1996 | Wilson et al. | |
| 5,710,123 A | 1/1998 | Heavner et al. | |
| 5,710,129 A | 1/1998 | Lynch et al. | |
| 5,928,906 A | 7/1999 | Koster et al. | |
| 6,326,193 B1 | 12/2001 | Liu et al. | |
| 6,716,422 B1 | 4/2004 | Gajewski et al. | |
| 2003/0138413 A1 | 7/2003 | Vicari et al. | |
| 2003/0166140 A1 | 9/2003 | Chen et al. | |
| 2003/0171253 A1 | 9/2003 | Ma et al. | |
| 2003/0175971 A1 | 9/2003 | Lindeman et al. | |
| 2004/0259247 A1 | 12/2004 | Tuschl et al. | |
| 2005/0147608 A1 | 7/2005 | Ryo et al. | |
| 2006/0239971 A1 | 10/2006 | Mohapatra | |
| 2006/0269519 A1 | 11/2006 | Chen et al. | |
| 2006/0292119 A1 | 12/2006 | Chen et al. | |
| 2010/0111993 A1* | 5/2010 | Tureci et al. ........ 424/192.1 |

FOREIGN PATENT DOCUMENTS

| | | |
|---|---|---|
| CN | 1763093 | 4/2006 |
| WO | WO 92/07065 | 4/1992 |
| WO | WO 94/07529 | 4/1994 |
| WO | WO 01/29058 | 4/2001 |
| WO | WO 01/75164 | 10/2001 |
| WO | WO 01/96584 | 12/2001 |
| WO | WO 2005/107381 | 11/2005 |

OTHER PUBLICATIONS

Shen et al. Nature Biotechnology 2004, vol. 22: 1546-1553.*
Cuadros et al. Infect. Immun. 2004, 72(5): 2810-2816.*
Brummelkamp et al. (Science 2002, vol. 296: 550-553).*
Schmidt et al. (Blood, Jul. 15, 2003, vol. 102, No. 2).*
Song et al. (Nature Biotechnology 2005, Vo. 23; 709-717).*
Akira et al., "Toll-like Receptor Signaling", Nat. Rev., 2004, Immunol. 4, pp. 499-511.
Akira et al., "Toll-like Receptor Signaling", Journal of Biological Chemistry, 2003, vol. 278, No. 40, pp. 38105-38108.
Alexander et al., "SOCS1 Is a Critical Inhibitor of Interferon y Signaling and Prevents the Potentially Fatal Neonatal Actions of the Cytokine", 1999, Cell 98, pp. 597-608.
Alexander et al., "The Role of Suppressors of Cytokine Signaling (SOCS) Proteins in Regulation of the Immune Response", Annu. Rev., 2004, Immunol. 22, 34 pages.
Baetz et al., "Suppressor of Cytokine Signaling (SOCS) Proteins Indirectly Regulate Toll-like Receptor Signaling in Innate Immune Cells", 2004, J. Biol. Chem. 279, pp. 54708-54715.
Banchereau et al., "Autoimmunity through cytokine-induced dendritic cell activation," 2004, Immunity 20, pp. 539-550.
Banchereau et al., "Dendritic cells and the control of Immunity," 1998, Nature 392, pp. 245-252.
Chong et al., Suppressor of cytokine signaling-1 is a critical regulator of interleukin-7-dependent CD8+ T cell differentiation, 2003, Immunity 18, pp. 475-487.
Crespo et al., "Indirect induction of suppressor of cytokine signaling-I in macrophages stimulated with bacterial lipopolysaccharide: partial role of autocrine/paracrine interferon-a/β," 2000, Biochem. J. 349, pp. 99-104.
Dalpke et al., "Suppressors of Cytokine Signaling (SOCS)-1 and SaCS-3 Are Induced by CpG-DNA and Modulate Cytokine Responses in APCs", 2001, J. Immunol. 166. pp. 7082-7089.

(Continued)

*Primary Examiner* — Kimberly Chong
(74) *Attorney, Agent, or Firm* — Foley & Lardner LLP

(57) ABSTRACT

The present invention provides adjuvants, vaccines and therapies in which antigen presentation is enhanced through inhibition of negative immune regulators. The compositions and methods are useful for generating immune responses against antigens, including microbial pathogens and tumor-associated antigens, by way of inhibiting a negative immune regulator in a cell and providing a proinflammatory stimulus. In particular, nucleotides encoding inhibitors of negative immune regulators, antigens, and co-stimulatory molecules are contacted with immune cells in order to elicit a therapeutic or prophylactic response.

14 Claims, 39 Drawing Sheets

OTHER PUBLICATIONS

Eyles et al., "Negative Regulation of Inerleukin-12 Signaling by Suppressor of Cytokine Signaling-I", 2002, J. Biol. Chem. 277, pp. 43735-43740.

Gilboa, "The promise of cancer vaccines," Nat. Rev. Cancer, vol. 4, :401-411, 2004.

Gingras et al., "Re-examination of the role of suppressor of cytokine signaling 1 (SOCS 1) in the regulation of toll-like receptor signaling," 2004, J. Biol. Chem. 279, pp. 54702-54707.

Grey et al., "A20 Inhibits Cytoking-induced Apoptosis and Nuclear Factor kB-dependent Gene Activation in Islets," 1999, J. Exp. Med. 190, pp. 1135-1145.

Hanada et al., "Suppressor of Cytokine Signaling-I Is Essential for Suppressing Dendritic Cell Activation and Systemic Autoimmunity", 2003, Immunity 19, pp. 437-450.

Heyninck et al., "A20 Inhibits NF-kB Activation by Dual Ubiquitin-Editing Functions," Trends Biochem Sci., Jan. 2005, vol. 1, pp. 1-4.

Kinjyo et al., "SOCS1/JAB Is a Negative Regulator of LPS-Induced Macrophage Activation", 2002, Immunity 17, pp. 583-591.

Kubo et al., "Suppressors of cytokine signaling and immunity", 2003, Nature Immunity 4, pp. 1169-1176.

Marine et al., "SOCS1 Deficiency Causes a Lymphocyte-Dependent Perinatal Lethality", 1999, Cell 98, pp. 609-616.

Matsuda et al., "SOCS-1 can suppress CD3 and Syk-mediated NF-AT activation in a non-lymphoid cell line", FEBS Letters, 2000, vol. 472, pp. 235-240.

Nakagawa et al., "SOSC-1 Participates in Negative Regulation of LPS Responses", 2002, Immunity 17, pp. 677-687.

International Search Report and Written Opinion received for PCT/US08/84916 mailed Jan. 19, 2010.

Okugawa, S. et al., "Bacterial flagellin inhibits T cell receptor-mediated activation of T cells by inducing suppressor of cytokine signalling-1 (SOCS-1)," Cellular Microbiology, vol. 8, No. 10, 2006, pp. 1571-1580.

Opipari et al., "The A20 Zinc Finger Protein Protects Cells from Tumor Necrosis Factor Cytotoxicity," 1992, J. Bio Chem. 267, pp. 12424-12427.

Pisarev, V. et al., "Full-Length Dominant-Negative Survivin for Cancer Immunotherapy," Clinical Cancer Research, vol. 9, Dec. 15, 2003, pp. 6523-6533.

Rao et al., "IL-12 is an Effective Adjuvant to Recombinant Vaccinia Virus-Based Tumor Vaccines," Journal of Immunology, 1996, vol. 156, 20 pages.

Saito, H. et al., "Cross-priming of cyclin B1, MUC-1 and survivin-specific CD8 T cells by dendritic cells loaded with killed allogeneic breast cancer cells," Breast Cancer Research, vol. 8, No. 6, Nov. 27, 2006, 9 pages.

Schmidt et al., "Survivin is a shared tumor-associated antigen expressed in a broad variety of malignancies and recognized by specific cytotoxic T cells," Blood, 2003, vol. 102, No. 2, pp. 571-576.

Wormald et al., "Inhibitors of Cytokine Signal Transduction", 2004, J. Biol. Chem. 279, pp. 821-824.

Yamamoto et al., "SOCS-3 inhibits IL-12 induced STAT4 activation by binding through its SH2 domain to the STAT4 docking site in the IL-12 receptor B2 subunit," Biochem and Biophys Research Comm., 2003, vol. 310, pp. 1188-1193.

You et al., "Induction of vigorous helper and cytotoxic T cell as well as B cell responses by dendritic cells expressing a modified antigen targeting receptor-mediated internalization pathway," 2000, J. Immunol., 165, pp. 4581-4591.

You et al., "Targeting dendritic cells to enhance DNA vaccine potency," 2001 Cancer Research, 61, pp. 3704-3711.

Yu et al., "Cancer vaccines: progress reveals new complexities," 2002, Journal of Clinical Investigation, 110, pp. 289-294.

English Translation of First Office Action; In re: Chinese Patent Application No. 200880125809.X; Dated: Nov. 24, 2011; Applicant: Baylor College of Medicine; (15 pgs.).

Second Office Action received in Chinese application No. 2008-80125809.X issued Aug. 13, 2012 (18 pages-English translation).

* cited by examiner

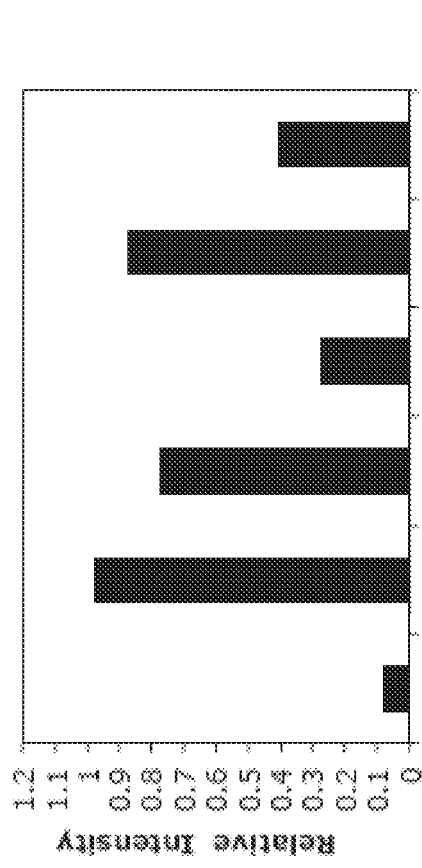
FIG. 2A
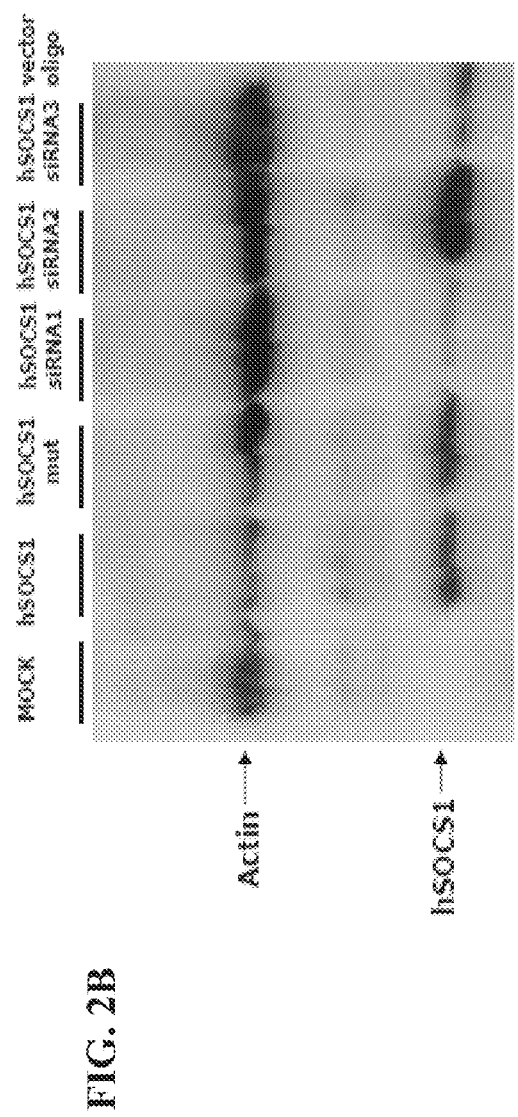
FIG. 2B
FIG. 2

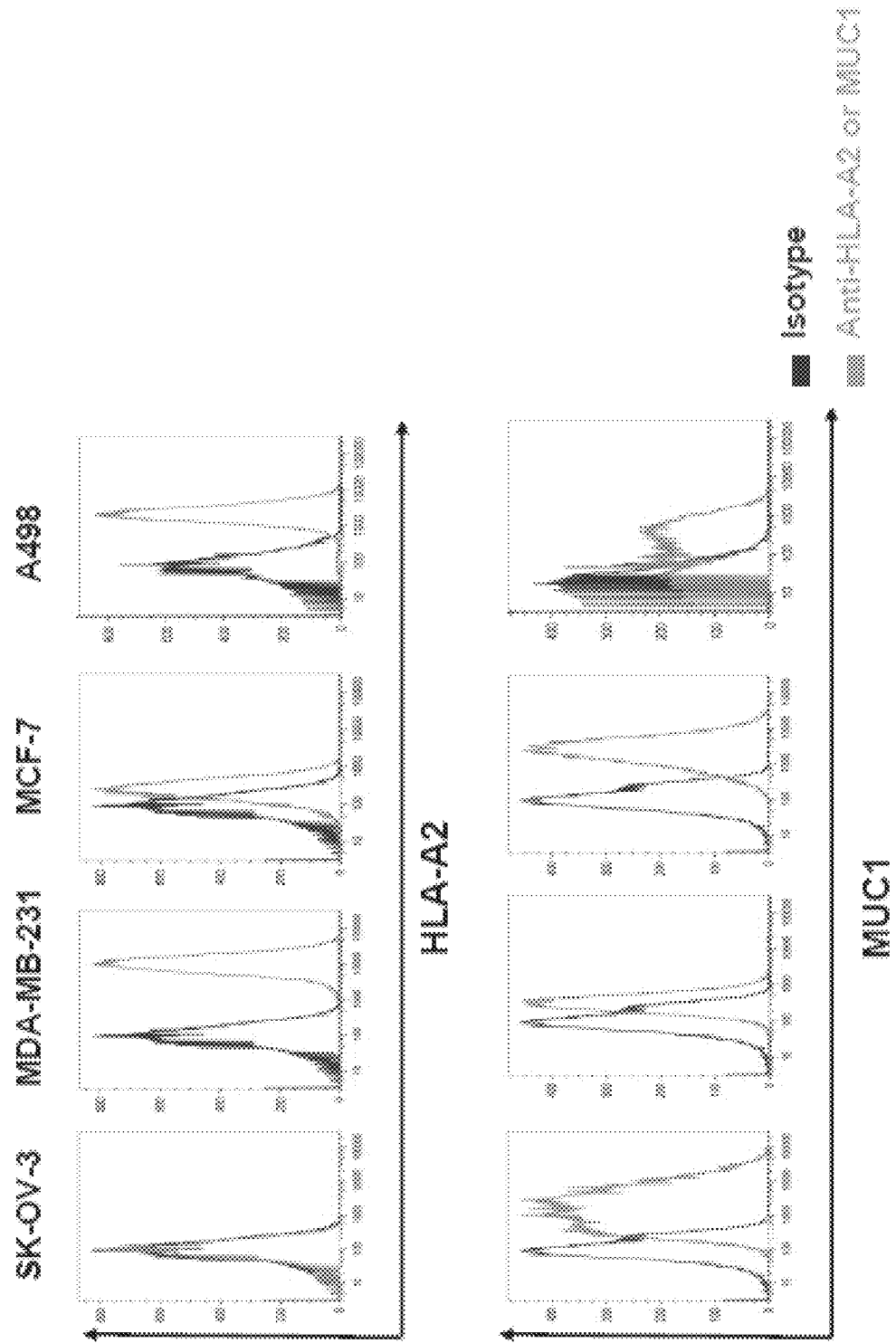

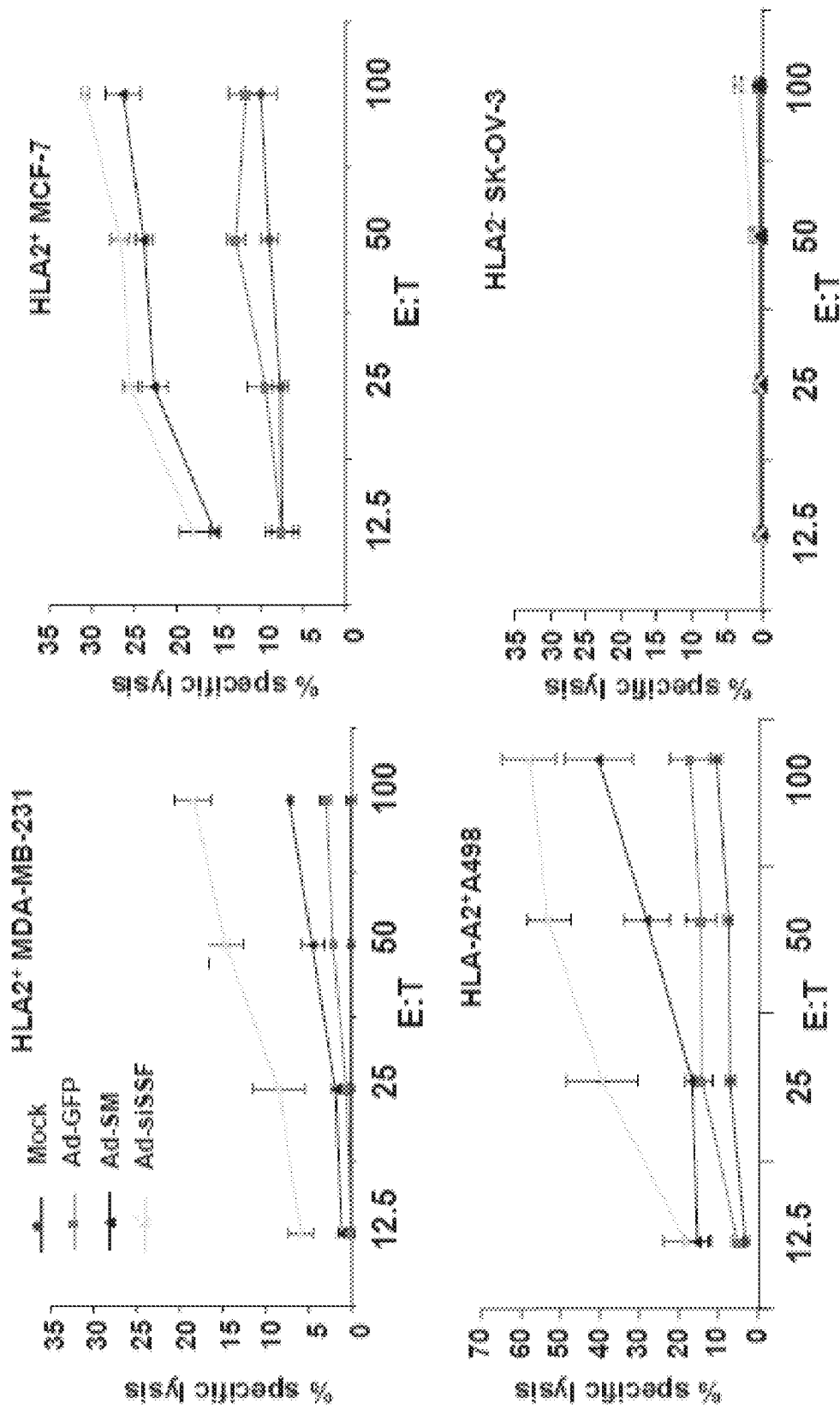

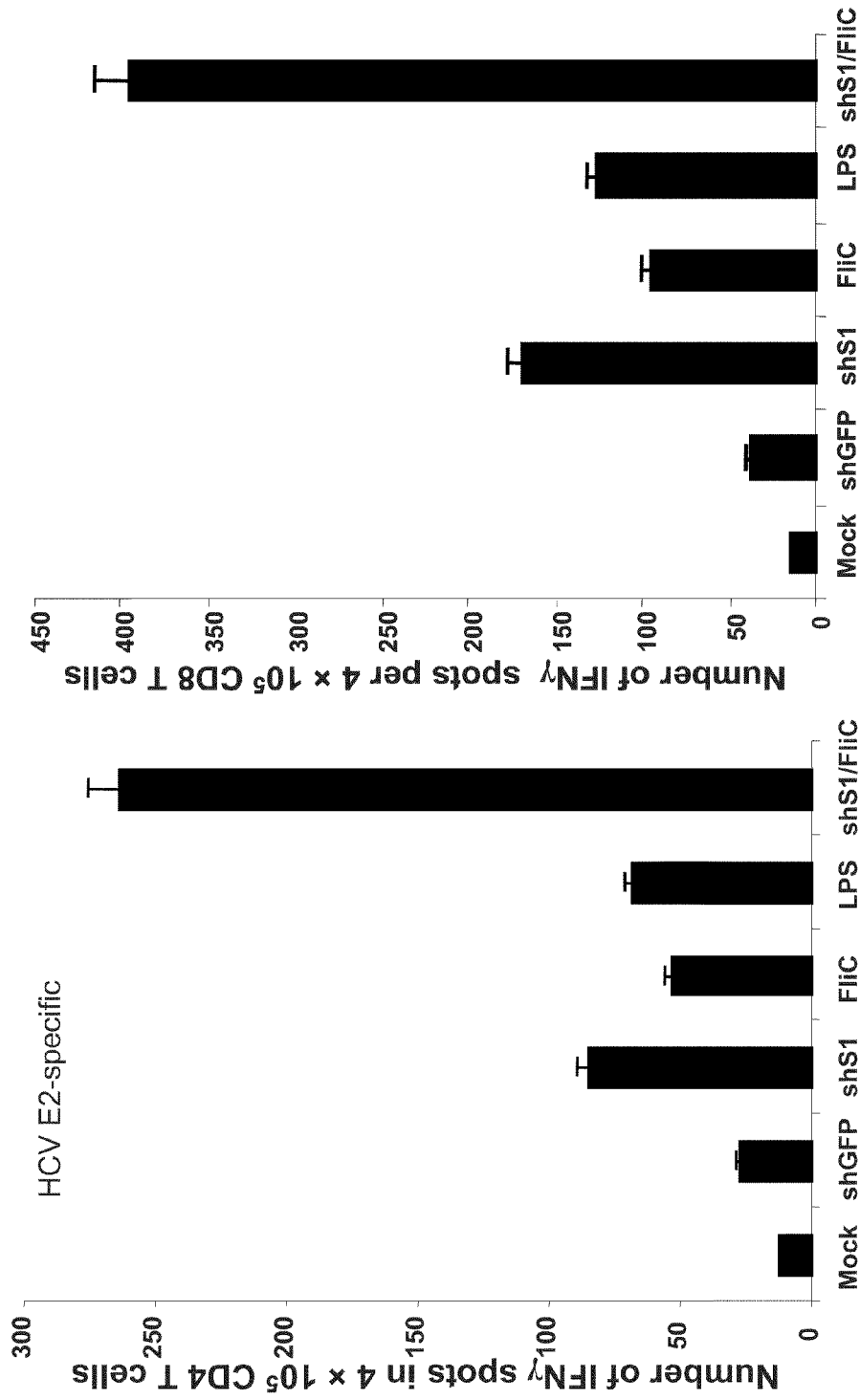

SEQUENCE LISTING

<160> NUMBER OF SEQ ID NOS: 178

<210> SEQ ID NO 1
<211> LENGTH: 162
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1
atttgcatgt cgctatgtgt tctgggaaat caccataaac gtgaaatgtc tttggatttg      60
ggaatcttat aagttctgta tgagaccaca gatccccag cacttccgca cattcttcaa     120
gagagaatgt gcggaagtgc gtgttttgg aaagcttatc ga                        162

<210> SEQ ID NO 2
<211> LENGTH: 576
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgaaggacc accgcatctc tacattcaag aactggccct tcttggaggg ctgcgcctgc      60
gccccggagc ggatggccga ggctggcttc atccactgcc ccactgagaa cgagccagac     120
ttggcccagt gtttcttctg tttcaaggag ctggaaggct gggagccgga tgacgacccc     180
atagaggaac ataaaaagca ttcatccggt tgcgctttcc tttctgtcaa gaagcagttt     240
gaagaattaa ccctcggtga attttgaaa ctggacagag aaagagccaa gaacaaaatt     300
gcaaaggaaa ccaacaataa gaagaaagaa tttgaggaaa ctgcaaagaa agtgcgccgt     360
gccatcgagc agctggctgc catggataag cttggtgtca cctcggcccc ggacaccagg     420
ccggccccgg gctccaccgc cccccagcc cacggtgtca cctcggcccc ggacaccagg     480
ccggccccgg gctccacctc cccccagcc cacggtgtca cctcggcccc ggacaccagg     540
ccggccccgg gctccaccgc cccccagcc cactaa                               576

<210> SEQ ID NO 3
<211> LENGTH: 1557
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 3
atgctcctgg ctgttttgta ctgcctgctg tggagtttcc agacctccgc tggccatttc      60
cctagaatgg cacaagtcat taatacaaac agcctgtcgc tgttgaccca gaataacctg     120
aacaaatccc agtccgctct gggcaccgct atcgagcgtc tgtcttccgg tctgcgtatc     180
aacagcgcga agacgatgc ggcaggtcag gcgattgcta accgttttac cgcgaacatc     240
aaaggtctga ctcaggcttc ccgtaacgct aacgacggta tctccattgc gcagaccact     300
gaaggcgcgc tgaacgaaat caacaacaac ctgcagcgtg tgcgtgaact ggcggttcag     360
tctgctaaca gcaccaactc ccagtctgac ctcgactcca tccaggctga aatcacccag     420
cgcctgaacg aaatcgaccg tgtatccggc cagactcagt tcaacggcgt gaaagtcctg     480
gcgcaggaca acaccctgac catccaggtt ggtgccaacg acggtgaaac tatcgatatc     540

```
gatctgaagc agatcaactc tcagaccctg ggtctggata cgctgaatgt gcaacaaaaa      600
tataaggtca gcgatacggc tgcaactgtt acaggatatg ccgatactac gattgcttta      660
gacaatagta cttttaaagc ctcggctact ggtcttggtg gtactgacca gaaaattgat      720
ggcgatttaa aatttgatga tacgactgga aaatattacg ccaaagttac cgttacgggg      780
ggaactggta agatggcta ttatgaagtt tccgttgata agacgaacgg tgaggtgact       840
cttgctggcg gtgcgacttc cccgcttaca ggtggactac ctgcgacagc aactgaggat      900
gtgaaaaatg tacaagttgc aaatgctgat ttgacagagg ctaaagccgc attgacagca      960
gcaggtgtta ccggcacagc atctgttgtt aagatgtctt atactgataa taacggtaaa     1020
actattgatg gtggtttagc agttaaggta ggcgatgatt actattctgc aactcaaaat     1080
aaagatggtt ccataagtat taatactacg aaatacactg cagatgacgg tacatccaaa     1140
actgcactaa acaaactggg tggcgcagac ggcaaaaccg aagttgtttc tattggtggt     1200
aaaacttacg ctgcaagtaa agccgaaggt cacaacttta aagcacagcc tgatctggcg     1260
gaagcggctg ctacaaccac cgaaaacccg ctgcagaaaa ttgatgctgc tttggcacag     1320
gttgacacgt tacgttctga cctgggtgcg gtacagaacc gtttcaactc cgctattacc     1380
aacctgggca caccgtaaa caacctgact tctgcccgta gccgtatcga agattccgac      1440
tacgcgaccg aagtttccaa catgtctcgc gcgcagattc tgcagcaggc cggtacctcc     1500
gttctggcgc aggcgaacca ggttccgcaa aacgtcctct ctttactgcg ttaagcg        1557

<210> SEQ ID NO 4
<211> LENGTH: 3736
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 4
atttgcatgt cgctatgtgt tctgggaaat caccataaac gtgaaatgtc tttggatttg       60
ggaatcttat aagttctgta tgagaccaca gatcccccac gcacttccgc acattcttca      120
agagagaatg tgcggaagtg cgtgtttttg gaaagcttat cgatcatagc ccatatatgg      180
agttccgcgt tacataactt acggtaaatg gcccgcctgg ctgaccgccc aacgaccccc      240
gcccattgac gtcaataatg acgtatgttc ccatagtaac gccaataggg actttccatt      300
gacgtcaatg ggtggagtat ttacggtaaa ctgcccactt ggcagtacat caagtgtatc      360
atatgccaag tacgccccct attgacgtca atgacggtaa atggcccgcc tggcattatg      420
cccagtacat gaccttatgg gactttccta cttggcagta catctacgta ttagtcatcg      480
ctattaccat ggtgatgcgg ttttggcagt acatcaatgg gcgtggatag cggtttgact      540
cacggggatt tccaagtctc cacccccattg acgtcaatgg gagtttgttt tggcaccaaa     600
atcaacggga ctttccaaaa tgtcgtaaca actccgcccc attgacgcaa atgggcggta      660
ggcgtgtacg gtgggaggtc tatataagca gagctggttt agtgaaccgt cagatccgct      720
aggtcgacat gaaggaccac cgcatctcta cattcaagaa ctggcccttc ttggagggct      780
gcgcctgcgc cccggagcgg atggccgagg ctggcttcat ccactgcccc actgagaacg      840
agccagactt ggcccagtgt ttcttctgtt tcaaggagct ggaaggctgg gagccggatg      900
acgaccccat agaggaacat aaaaagcatt catccggttg cgctttcctt tctgtcaaga     960
agcagtttga agaattaacc ctcggtgaat ttttgaaact ggacagagaa agagccaaga    1020
```

```
acaaaattgc aaaggaaacc aacaataaga agaaagaatt tgaggaaact gcaaagaaag    1080
tgcgccgtgc catcgagcag ctggctgcca tggataagct tggtgtcacc tcggccccgg    1140
acaccaggcc ggccccgggc tccaccgccc cccagccca cggtgtcacc tcggccccgg     1200
acaccaggcc ggccccgggc tccacctccc cccagccca cggtgtcacc tcggccccgg     1260
acaccaggcc ggccccgggc tccaccgccc cccagccca ctaaggcggc cgctaaattc     1320
cggcccctct ccctcccccc ccctaacgt tactggccga agccgcttgg aataaggccg     1380
gtgtgcgttt gtctatatgt tattttccac catattgccg tcttttggca atgtgagggc    1440
ccggaaacct ggccctgtct tcttgacgag cattcctagg ggtctttccc ctctcgccaa    1500
aggaatgcaa ggtctgttga atgtcgtgaa ggaagcagtt cctctggaag cttcttgaag    1560
acaaacaacg tctgtagcga ccctttgcag gcagcggaac ccccccactg gcgacaggtg    1620
cctctgcggc caaaagccac gtgtataaga tacacctgca aaggcggcac aaccccagtg    1680
ccacgttgtg agttggatag ttgtggaaag agtcaaatgg ctctcctcaa gcgtattcaa    1740 caagggggctg aaggatgccc agaaggtacc ccattgtatg ggatctgatc tggggcctcg   1800
gtgcacatgc tttacatgtg tttagtcgag gttaaaaaaa cgtctaggcc ccccgaacca    1860
cggggacgtg gttttccttt gaaaaacacg atgataatat ggccacactc gagatgctcc    1920
tggctgtttt gtactgcctg ctgtggagtt tccagacctc cgctggccat ttccctagaa    1980
tggcacaagt cattaataca aacagcctgt cgctgttgac ccagaataac ctgaacaaat    2040
cccagtccgc tctgggcacc gctatcgagc gtctgtcttc cggtctgcgt atcaacagcg    2100
cgaaagacga tgcggcaggt caggcgattg ctaaccgttt taccgcgaac atcaaaggtc    2160
tgactcaggc ttcccgtaac gctaacgacg gtatctccat tgcgcagacc actgaaggcg    2220
cgctgaacga aatcaacaac aacctgcagc gtgtgcgtga actggcggtt cagtctgcta    2280
acagcaccaa ctcccagtct gacctcgact ccatccaggc tgaaatcacc cagcgcctga    2340
acgaaatcga ccgtgtatcc ggccagactc agttcaacgg cgtgaaagtc ctggcgcagg    2400
acaacaccct gaccatccag gttggtgcca cgacggtga aactatcgat atcgatctga    2460
agcagatcaa ctctcagacc ctgggtctgg atacgctgaa tgtgcaacaa aaatataagg    2520
tcagcgatac ggctgcaact gttacaggat atgccgatac tacgattgct ttagacaata    2580 gtactttaa agcctcggct actggtcttg gtggtactga ccagaaaatt gatggcgatt     2640
taaaatttga tgatacgact ggaaaatatt acgccaaagt taccgttacg gggggaactg    2700
gtaaagatgg ctattatgaa gtttccgttg ataagacgaa cggtgaggtg actcttgctg    2760
gcggtgcgac ttccccgctt acaggtggac tacctgcgac agcaactgag gatgtgaaaa    2820
atgtacaagt tgcaaatgct gatttgacag aggctaaagc cgcattgaca gcagcaggtg    2880
ttaccggcac agcatctgtt gttaagatgt cttatactga taataacggt aaaactattg    2940
atggtggttt agcagttaag gtaggcgatg attactattc tgcaactcaa aataaagatg    3000
gttccataag tattaatact acgaaataca ctgcagatga cggtacatcc aaaactgcac    3060
taaacaaact gggtggcgca gacggcaaaa ccgaagttgt ttctattggt ggtaaaactt    3120
acgctgcaag taaagccgaa ggtcacaact ttaaagcaca gcctgatctg gcggaagcgg    3180
ctgctacaac caccgaaaac ccgctgcaga aaattgatgc tgctttggca caggttgaca    3240
cgttacgttc tgacctgggt gcggtacaga accgtttcaa ctccgctatt accaacctgg    3300
gcaacaccgt aaacaacctg acttctgccc gtagccgtat cgaagattcc gactacgcga    3360
ccgaagtttc caacatgtct cgcgcgcaga ttctgcagca ggccggtacc tccgttctgg    3420
```

-continued

```
cgcaggcgaa ccaggttccg caaaacgtcc tctctttact gcgttaagcg gccgctctag    3480
ataagatatc cgatccaccg gatctagata actgatcata atcagccata ccacatttgt    3540
agaggtttta cttgctttaa aaaacctccc acacctcccc ctgaacctga aacataaaat    3600
gaatgcaatt gttgttgtta acttgtttat tgcagcttat aatggttaca aataaagcaa    3660
tagcatcaca aatttcacaa ataaagcatt tttttcactg cattctagtt gtggtccaac    3720
tcatcaatgt atctta                                                   3736
```

<210> SEQ ID NO 5
<211> LENGTH: 19
<212> TYPE: DNA
<213> ORGANISM: Homo sapiens

<400> SEQUENCE: 5
cacgcacttc cgcacattc                          19

<210> SEQ ID NO 6
<211> LENGTH: 19
<212> TYPE: DNA
<213> ORGANISM: Homo sapiens

<400> SEQUENCE: 6
ttccgttcgc acgccgatt                          19

<210> SEQ ID NO 7
<211> LENGTH: 19
<212> TYPE: DNA
<213> ORGANISM: Homo sapiens

<400> SEQUENCE: 7
gagcttcgac tgcctcttc                          19

<210> SEQ ID NO 8
<211> LENGTH: 19
<212> TYPE: DNA
<213> ORGANISM: Homo sapiens

<400> SEQUENCE: 8
ccaccagtcc tcaaataaa                          19

<210> SEQ ID NO 9
<211> LENGTH: 19
<212> TYPE: DNA
<213> ORGANISM: Homo sapiens

<400> SEQUENCE: 9
tgattgacct aaccataga                          19

<210> SEQ ID NO 10
<211> LENGTH: 19
<212> TYPE: DNA
<213> ORGANISM: Homo sapiens

<400> SEQUENCE: 10
gacacaagct acattaata                          19

<210> SEQ ID NO 11
<211> LENGTH: 19
<212> TYPE: DNA
<213> ORGANISM: Homo sapiens

<400> SEQUENCE: 11
tgacgcaact ctttacatt                                                          19

<210> SEQ ID NO 12
<211> LENGTH: 19
<212> TYPE: DNA
<213> ORGANISM: Homo sapiens

<400> SEQUENCE: 12
ccagccgacc aattaatat                                                          19

<210> SEQ ID NO 13
<211> LENGTH: 19
<212> TYPE: DNA
<213> ORGANISM: Homo sapiens

<400> SEQUENCE: 13
ttacgactta caaggatta                                                          19

<210> SEQ ID NO 14
<211> LENGTH: 19
<212> TYPE: DNA
<213> ORGANISM: Homo sapiens

<400> SEQUENCE: 14
agaaggtcga agttattga                                                          19

<210> SEQ ID NO 15
<211> LENGTH: 19
<212> TYPE: DNA
<213> ORGANISM: Homo sapiens

<400> SEQUENCE: 15
attactcctt gtctgtgta                                                          19

<210> SEQ ID NO 16
<211> LENGTH: 19
<212> TYPE: DNA
<213> ORGANISM: Homo sapiens

<400> SEQUENCE: 16
agattgtgat gagatccaa                                                          19

<210> SEQ ID NO 17
<211> LENGTH: 19
<212> TYPE: DNA
<213> ORGANISM: Homo sapiens

<400> SEQUENCE: 17
tttgaggaag cgcacttta                                                          19

<210> SEQ ID NO 18
<211> LENGTH: 19
<212> TYPE: DNA
<213> ORGANISM: Homo sapiens

<400> SEQUENCE: 18
agccgacatc caaggttta                                                          19

<210> SEQ ID NO 19
<211> LENGTH: 19
<212> TYPE: DNA
<213> ORGANISM: Homo sapiens

<400> SEQUENCE: 19
cgacatccaa ggtttagat                                           19

<210> SEQ ID NO 20
<211> LENGTH: 19
<212> TYPE: DNA
<213> ORGANISM: Homo sapiens

<400> SEQUENCE: 20
ccagagcact aattaaaga                                           19

<210> SEQ ID NO 21
<211> LENGTH: 19
<212> TYPE: DNA
<213> ORGANISM: Homo sapiens

<400> SEQUENCE: 21
ccatgttatt acagagatt                                           19

<210> SEQ ID NO 22
<211> LENGTH: 19
<212> TYPE: DNA
<213> ORGANISM: Homo sapiens

<400> SEQUENCE: 22
gctattccgc cttcattaa                                           19

<210> SEQ ID NO 23
<211> LENGTH: 19
<212> TYPE: DNA
<213> ORGANISM: Homo sapiens

<400> SEQUENCE: 23
tattccgcct tcattaaca                                           19

<210> SEQ ID NO 24
<211> LENGTH: 19
<212> TYPE: DNA
<213> ORGANISM: Homo sapiens

<400> SEQUENCE: 24
ccaccatacg ccaatatca                                           19

<210> SEQ ID NO 25
<211> LENGTH: 19
<212> TYPE: DNA
<213> ORGANISM: Homo sapiens

<400> SEQUENCE: 25
gcgctgcatt tattgaaga                                           19

<210> SEQ ID NO 26
<211> LENGTH: 19
<212> TYPE: DNA
<213> ORGANISM: Homo sapiens

<400> SEQUENCE: 26
agaatctgtt actcagaca                                           19

<210> SEQ ID NO 27
<211> LENGTH: 19
<212> TYPE: DNA
<213> ORGANISM: Homo sapiens

<400> SEQUENCE: 27

```
tcactcacct catgtacct                                              19
```

<210> SEQ ID NO 28
<211> LENGTH: 19
<212> TYPE: DNA
<213> ORGANISM: Homo sapiens

<400> SEQUENCE: 28

```
tctgtccgct ggtgaagat                                              19
```

<210> SEQ ID NO 29
<211> LENGTH: 19
<212> TYPE: DNA
<213> ORGANISM: Homo sapiens

<400> SEQUENCE: 29

```
tcgcattgac gccaagaca                                              19
```

<210> SEQ ID NO 30
<211> LENGTH: 18
<212> TYPE: DNA
<213> ORGANISM: Homo sapiens

<400> SEQUENCE: 30

```
gctctacgga agtactta                                               18
```

<210> SEQ ID NO 31
<211> LENGTH: 19
<212> TYPE: DNA
<213> ORGANISM: Homo sapiens

<400> SEQUENCE: 31

```
ctacggaaag tacttaaac                                              19
```

<210> SEQ ID NO 32
<211> LENGTH: 19
<212> TYPE: DNA
<213> ORGANISM: Homo sapiens

<400> SEQUENCE: 32

```
caaacagcat ccagataga                                              19
```

<210> SEQ ID NO 33
<211> LENGTH: 19
<212> TYPE: DNA
<213> ORGANISM: Homo sapiens

<400> SEQUENCE: 33

```
tgatgttcca gacaataat                                              19
```

<210> SEQ ID NO 34
<211> LENGTH: 19
<212> TYPE: DNA
<213> ORGANISM: Homo sapiens

<400> SEQUENCE: 34

```
taaatgcgcc tgtgactta                                              19
```

<210> SEQ ID NO 35
<211> LENGTH: 19
<212> TYPE: DNA
<213> ORGANISM: Homo sapiens

<400> SEQUENCE: 35

-continued

| tcacaacacc tcaaacata | 19 |

<210> SEQ ID NO 36
<211> LENGTH: 19
<212> TYPE: DNA
<213> ORGANISM: Homo sapiens

<400> SEQUENCE: 36

| tcagaagtat tacgcagaa | 19 |

<210> SEQ ID NO 37
<211> LENGTH: 19
<212> TYPE: DNA
<213> ORGANISM: Homo sapiens

<400> SEQUENCE: 37

| gacaaccggt cgaaagaaa | 19 |

<210> SEQ ID NO 38
<211> LENGTH: 19
<212> TYPE: DNA
<213> ORGANISM: Homo sapiens

<400> SEQUENCE: 38

| agacacacgc aactttaaa | 19 |

<210> SEQ ID NO 39
<211> LENGTH: 19
<212> TYPE: DNA
<213> ORGANISM: Homo sapiens

<400> SEQUENCE: 39

| cagacacacg caactttaa | 19 |

<210> SEQ ID NO 40
<211> LENGTH: 19
<212> TYPE: DNA
<213> ORGANISM: Homo sapiens

<400> SEQUENCE: 40

| acacacgcaa ctttaaatt | 19 |

<210> SEQ ID NO 41
<211> LENGTH: 19
<212> TYPE: DNA
<213> ORGANISM: Homo sapiens

<400> SEQUENCE: 41

| acgaatgctt tcagttcaa | 19 |

<210> SEQ ID NO 42
<211> LENGTH: 19
<212> TYPE: DNA
<213> ORGANISM: Homo sapiens

<400> SEQUENCE: 42

| atactcggaa ctggaatga | 19 |

<210> SEQ ID NO 43
<211> LENGTH: 19
<212> TYPE: DNA
<213> ORGANISM: Homo sapiens

<400> SEQUENCE: 43

```
gaagcttgtg gcgctgaaa                                              19

<210> SEQ ID NO 44
<211> LENGTH: 21
<212> TYPE: DNA
<213> ORGANISM: Homo sapiens

<400> SEQUENCE: 44
aaagccggct gcgtgtattt t                                           21

<210> SEQ ID NO 45
<211> LENGTH: 21
<212> TYPE: DNA
<213> ORGANISM: Homo sapiens

<400> SEQUENCE: 45
aaagggagct ctagtccttt t                                           21

<210> SEQ ID NO 46
<211> LENGTH: 21
<212> TYPE: DNA
<213> ORGANISM: Homo sapiens

<400> SEQUENCE: 46
aagggagctc tagtccttttt t                                          21

<210> SEQ ID NO 47
<211> LENGTH: 21
<212> TYPE: DNA
<213> ORGANISM: Homo sapiens

<400> SEQUENCE: 47
aagccctcat cgacagaaac a                                           21

<210> SEQ ID NO 48
<211> LENGTH: 21
<212> TYPE: DNA
<213> ORGANISM: Homo sapiens

<400> SEQUENCE: 48
aaacgaacgg tgacggcaat t                                           21

<210> SEQ ID NO 49
<211> LENGTH: 21
<212> TYPE: DNA
<213> ORGANISM: Homo sapiens

<400> SEQUENCE: 49
aaacagacac acgcaacttt a                                           21

<210> SEQ ID NO 50
<211> LENGTH: 21
<212> TYPE: DNA
<213> ORGANISM: Homo sapiens

<400> SEQUENCE: 50
aacagacaca cgcaaccttta a                                          21

<210> SEQ ID NO 51
<211> LENGTH: 21
<212> TYPE: DNA
<213> ORGANISM: Homo sapiens

<400> SEQUENCE: 51
```

```
aatgtgcagc acaacggatt t                                              21

<210> SEQ ID NO 52
<211> LENGTH: 21
<212> TYPE: DNA
<213> ORGANISM: Homo sapiens

<400> SEQUENCE: 52
aaaagccggc tgcgtgtatt t                                              21

<210> SEQ ID NO 53
<211> LENGTH: 21
<212> TYPE: DNA
<213> ORGANISM: Homo sapiens

<400> SEQUENCE: 53
aaactcaacc agctgccttt t                                              21

<210> SEQ ID NO 54
<211> LENGTH: 21
<212> TYPE: DNA
<213> ORGANISM: Homo sapiens
<220> FEATURE:
<221> NAME/KEY: modified_base
<222> LOCATION: (18)..(18)
<223> OTHER INFORMATION: inosine
<220> FEATURE:
<221> NAME/KEY: modified_base
<222> LOCATION: (20)..(20)
<223> OTHER INFORMATION: inosine

<400> SEQUENCE: 54
aactcaacca gctgcctntn t                                              21

<210> SEQ ID NO 55
<211> LENGTH: 21
<212> TYPE: DNA
<213> ORGANISM: Homo sapiens

<400> SEQUENCE: 55
aagtccttcc tcaggctttg t                                              21

<210> SEQ ID NO 56
<211> LENGTH: 21
<212> TYPE: DNA
<213> ORGANISM: Homo sapiens

<400> SEQUENCE: 56
aaagccagaa gaaactcaac t                                              21

<210> SEQ ID NO 57
<211> LENGTH: 21
<212> TYPE: DNA
<213> ORGANISM: Homo sapiens

<400> SEQUENCE: 57
aatccgagct gttccacttg t                                              21

<210> SEQ ID NO 58
<211> LENGTH: 21
<212> TYPE: DNA
<213> ORGANISM: Homo sapiens

<400> SEQUENCE: 58
aaggctggga ccatggcaca a                                              21
```

```
<210> SEQ ID NO 59
<211> LENGTH: 21
<212> TYPE: DNA
<213> ORGANISM: Homo sapiens

<400> SEQUENCE: 59
aatgccgcaa agttggatga a                                              21

<210> SEQ ID NO 60
<211> LENGTH: 21
<212> TYPE: DNA
<213> ORGANISM: Homo sapiens

<400> SEQUENCE: 60
aaggccacaa tacctttta a                                               21

<210> SEQ ID NO 61
<211> LENGTH: 21
<212> TYPE: DNA
<213> ORGANISM: Homo sapiens

<400> SEQUENCE: 61
aaaaccttca actgaggact t                                              21

<210> SEQ ID NO 62
<211> LENGTH: 21
<212> TYPE: DNA
<213> ORGANISM: Homo sapiens

<400> SEQUENCE: 62
aaagacaggg tgttccaatg a                                              21

<210> SEQ ID NO 63
<211> LENGTH: 21
<212> TYPE: DNA
<213> ORGANISM: Homo sapiens

<400> SEQUENCE: 63
aagacagggt gttccaatga a                                              21

<210> SEQ ID NO 64
<211> LENGTH: 21
<212> TYPE: DNA
<213> ORGANISM: Homo sapiens

<400> SEQUENCE: 64
aatggaggaa gaagatgtga t                                              21

<210> SEQ ID NO 65
<211> LENGTH: 21
<212> TYPE: DNA
<213> ORGANISM: Homo sapiens

<400> SEQUENCE: 65
aagatggctt cactgaagaa a                                              21

<210> SEQ ID NO 66
<211> LENGTH: 21
<212> TYPE: DNA
<213> ORGANISM: Homo sapiens

<400> SEQUENCE: 66
aactccaaag atggcttcac t                                              21
```

```
<210> SEQ ID NO 67
<211> LENGTH: 21
<212> TYPE: DNA
<213> ORGANISM: Homo sapiens

<400> SEQUENCE: 67
aagtgccttc tgaatcaagg a                                              21

<210> SEQ ID NO 68
<211> LENGTH: 21
<212> TYPE: DNA
<213> ORGANISM: Homo sapiens

<400> SEQUENCE: 68
aaaagggaac ctgcttcttt a                                              21

<210> SEQ ID NO 69
<211> LENGTH: 21
<212> TYPE: DNA
<213> ORGANISM: Homo sapiens

<400> SEQUENCE: 69
aaagcccaag gaaggagtca a                                              21

<210> SEQ ID NO 70
<211> LENGTH: 21
<212> TYPE: DNA
<213> ORGANISM: Homo sapiens

<400> SEQUENCE: 70
aaggagtcaa gactgagaac a                                              21

<210> SEQ ID NO 71
<211> LENGTH: 21
<212> TYPE: DNA
<213> ORGANISM: Homo sapiens

<400> SEQUENCE: 71
aagaggcata caccacttag t                                              21

<210> SEQ ID NO 72
<211> LENGTH: 21
<212> TYPE: DNA
<213> ORGANISM: Homo sapiens

<400> SEQUENCE: 72
aacgacaggg attgtcaatg a                                              21

<210> SEQ ID NO 73
<211> LENGTH: 21
<212> TYPE: DNA
<213> ORGANISM: Homo sapiens

<400> SEQUENCE: 73
aagggaacct gcttctttac t                                              21

<210> SEQ ID NO 74
<211> LENGTH: 21
<212> TYPE: DNA
<213> ORGANISM: Homo sapiens

<400> SEQUENCE: 74
aagactgaga acaacgatca t                                              21
```

```
<210> SEQ ID NO 75
<211> LENGTH: 21
<212> TYPE: DNA
<213> ORGANISM: Homo sapiens

<400> SEQUENCE: 75
aacagacaca cctgcacagt t                                        21

<210> SEQ ID NO 76
<211> LENGTH: 21
<212> TYPE: DNA
<213> ORGANISM: Homo sapiens

<400> SEQUENCE: 76
aatccttgca taccttgttc a                                        21

<210> SEQ ID NO 77
<211> LENGTH: 21
<212> TYPE: DNA
<213> ORGANISM: Homo sapiens

<400> SEQUENCE: 77
aagtcaagcg tcttgttgtt t                                        21

<210> SEQ ID NO 78
<211> LENGTH: 21
<212> TYPE: DNA
<213> ORGANISM: Homo sapiens

<400> SEQUENCE: 78
aacagcagac gggaggtgtc t                                        21

<210> SEQ ID NO 79
<211> LENGTH: 21
<212> TYPE: DNA
<213> ORGANISM: Homo sapiens

<400> SEQUENCE: 79
aacctgcttc tttactccag a                                        21

<210> SEQ ID NO 80
<211> LENGTH: 21
<212> TYPE: DNA
<213> ORGANISM: Homo sapiens

<400> SEQUENCE: 80
aactgcaatt tggttccacc a                                        21

<210> SEQ ID NO 81
<211> LENGTH: 19
<212> TYPE: DNA
<213> ORGANISM: Homo sapiens

<400> SEQUENCE: 81
acaccatcga cgtgttcca                                           19

<210> SEQ ID NO 82
<211> LENGTH: 21
<212> TYPE: DNA
<213> ORGANISM: Homo sapiens

<400> SEQUENCE: 82
aaggattggc acaaccaaaa t                                        21
```

```
<210> SEQ ID NO 83
<211> LENGTH: 21
<212> TYPE: DNA
<213> ORGANISM: Homo sapiens

<400> SEQUENCE: 83
aattgggcca atcagaattg t                                              21

<210> SEQ ID NO 84
<211> LENGTH: 21
<212> TYPE: DNA
<213> ORGANISM: Homo sapiens

<400> SEQUENCE: 84
aaccgagtct tttggtaatt t                                              21

<210> SEQ ID NO 85
<211> LENGTH: 21
<212> TYPE: DNA
<213> ORGANISM: Homo sapiens

<400> SEQUENCE: 85
aatggtgttg tggcctcaga t                                              21

<210> SEQ ID NO 86
<211> LENGTH: 21
<212> TYPE: DNA
<213> ORGANISM: Homo sapiens

<400> SEQUENCE: 86
aaggtgtctg cggaaactcg a                                              21

<210> SEQ ID NO 87
<211> LENGTH: 21
<212> TYPE: DNA
<213> ORGANISM: Homo sapiens

<400> SEQUENCE: 87
aagggaaaat actggaatgc t                                              21

<210> SEQ ID NO 88
<211> LENGTH: 21
<212> TYPE: DNA
<213> ORGANISM: Homo sapiens

<400> SEQUENCE: 88
aagcagatca gattccgatt t                                              21

<210> SEQ ID NO 89
<211> LENGTH: 21
<212> TYPE: DNA
<213> ORGANISM: Homo sapiens

<400> SEQUENCE: 89
aaaagggaac ctgcttcttt a                                              21

<210> SEQ ID NO 90
<211> LENGTH: 21
<212> TYPE: DNA
<213> ORGANISM: Homo sapiens

<400> SEQUENCE: 90
aaagcccaca gaagaagtca a                                              21
```

```
<210> SEQ ID NO 91
<211> LENGTH: 21
<212> TYPE: DNA
<213> ORGANISM: Homo sapiens

<400> SEQUENCE: 91
aagaggcaga caccacttag t                                              21

<210> SEQ ID NO 92
<211> LENGTH: 21
<212> TYPE: DNA
<213> ORGANISM: Homo sapiens

<400> SEQUENCE: 92
aagggaacct gcttctttac t                                              21

<210> SEQ ID NO 93
<211> LENGTH: 21
<212> TYPE: DNA
<213> ORGANISM: Homo sapiens

<400> SEQUENCE: 93
aagtggagac aggatgggaa a                                              21

<210> SEQ ID NO 94
<211> LENGTH: 21
<212> TYPE: DNA
<213> ORGANISM: Homo sapiens

<400> SEQUENCE: 94
aacgaaaagc ccacagaaga a                                              21

<210> SEQ ID NO 95
<211> LENGTH: 21
<212> TYPE: DNA
<213> ORGANISM: Homo sapiens

<400> SEQUENCE: 95
aagaagtcaa gactgagaac a                                              21

<210> SEQ ID NO 96
<211> LENGTH: 21
<212> TYPE: DNA
<213> ORGANISM: Homo sapiens

<400> SEQUENCE: 96
aagtcaagac tgagaacaac a                                              21

<210> SEQ ID NO 97
<211> LENGTH: 21
<212> TYPE: DNA
<213> ORGANISM: Homo sapiens

<400> SEQUENCE: 97
aacagacaaa cctgcacagt t                                              21

<210> SEQ ID NO 98
<211> LENGTH: 21
<212> TYPE: DNA
<213> ORGANISM: Homo sapiens

<400> SEQUENCE: 98
aaaccaaaca gccaatggta t                                              21
```

```
<210> SEQ ID NO 99
<211> LENGTH: 21
<212> TYPE: DNA
<213> ORGANISM: Homo sapiens

<400> SEQUENCE: 99
aaggtggcgg gacaggatgg t                                              21

<210> SEQ ID NO 100
<211> LENGTH: 21
<212> TYPE: DNA
<213> ORGANISM: Homo sapiens

<400> SEQUENCE: 100
aacagcctac gggaggtgtc t                                              21

<210> SEQ ID NO 101
<211> LENGTH: 21
<212> TYPE: DNA
<213> ORGANISM: Homo sapiens

<400> SEQUENCE: 101
aacctgcttc tttactccag a                                              21

<210> SEQ ID NO 102
<211> LENGTH: 21
<212> TYPE: DNA
<213> ORGANISM: Homo sapiens

<400> SEQUENCE: 102
aacgctgttc tttaaagacc a                                              21

<210> SEQ ID NO 103
<211> LENGTH: 21
<212> TYPE: DNA
<213> ORGANISM: Homo sapiens

<400> SEQUENCE: 103
aactgcaatt tggttccacc a                                              21

<210> SEQ ID NO 104
<211> LENGTH: 19
<212> TYPE: DNA
<213> ORGANISM: Homo sapiens

<400> SEQUENCE: 104
actccaagat ggcaagctg                                                 19

<210> SEQ ID NO 105
<211> LENGTH: 19
<212> TYPE: DNA
<213> ORGANISM: Homo sapiens

<400> SEQUENCE: 105
tggcaagctg cagctatgt                                                 19

<210> SEQ ID NO 106
<211> LENGTH: 21
<212> TYPE: DNA
<213> ORGANISM: Homo sapiens

<400> SEQUENCE: 106
aaggagaaaa tggacagtct a                                              21
```

```
<210> SEQ ID NO 107
<211> LENGTH: 21
<212> TYPE: DNA
<213> ORGANISM: Homo sapiens

<400> SEQUENCE: 107
aaaggcatca ctatggactt t                                     21

<210> SEQ ID NO 108
<211> LENGTH: 21
<212> TYPE: DNA
<213> ORGANISM: Homo sapiens

<400> SEQUENCE: 108
aagatggcaa gctgcagcta t                                     21

<210> SEQ ID NO 109
<211> LENGTH: 21
<212> TYPE: DNA
<213> ORGANISM: Homo sapiens

<400> SEQUENCE: 109
aaactggcct gcaaaaccat a                                     21

<210> SEQ ID NO 110
<211> LENGTH: 21
<212> TYPE: DNA
<213> ORGANISM: Homo sapiens

<400> SEQUENCE: 110
aagctgcagc tatgtggctc a                                     21

<210> SEQ ID NO 111
<211> LENGTH: 21
<212> TYPE: DNA
<213> ORGANISM: Homo sapiens

<400> SEQUENCE: 111
aaagcgagac aggcccgtgg a                                     21

<210> SEQ ID NO 112
<211> LENGTH: 19
<212> TYPE: DNA
<213> ORGANISM: Homo sapiens

<400> SEQUENCE: 112
gacgagatgg acaataaga                                        19

<210> SEQ ID NO 113
<211> LENGTH: 19
<212> TYPE: DNA
<213> ORGANISM: Homo sapiens

<400> SEQUENCE: 113
tgagcaagat ccagacgct                                        19

<210> SEQ ID NO 114
<211> LENGTH: 19
<212> TYPE: DNA
<213> ORGANISM: Homo sapiens

<400> SEQUENCE: 114
agcgacgaga tggacaata                                        19
```

```
<210> SEQ ID NO 115
<211> LENGTH: 19
<212> TYPE: DNA
<213> ORGANISM: Homo sapiens

<400> SEQUENCE: 115
acgagatgga caataagat                                                19

<210> SEQ ID NO 116
<211> LENGTH: 19
<212> TYPE: DNA
<213> ORGANISM: Homo sapiens

<400> SEQUENCE: 116
gagcgacgag atggacaat                                                19

<210> SEQ ID NO 117
<211> LENGTH: 19
<212> TYPE: DNA
<213> ORGANISM: Homo sapiens

<400> SEQUENCE: 117
cgagatggac aataagatg                                                19

<210> SEQ ID NO 118
<211> LENGTH: 19
<212> TYPE: DNA
<213> ORGANISM: Homo sapiens

<400> SEQUENCE: 118
cagcaagaag tcgagcgaa                                                19

<210> SEQ ID NO 119
<211> LENGTH: 19
<212> TYPE: DNA
<213> ORGANISM: Homo sapiens

<400> SEQUENCE: 119
aagtcgagcg aagatggca                                                19

<210> SEQ ID NO 120
<211> LENGTH: 19
<212> TYPE: DNA
<213> ORGANISM: Homo sapiens

<400> SEQUENCE: 120
agcaagaagt cgagcgaag                                                19

<210> SEQ ID NO 121
<211> LENGTH: 19
<212> TYPE: DNA
<213> ORGANISM: Homo sapiens

<400> SEQUENCE: 121
aagaagtcga gcgaagatg                                                19

<210> SEQ ID NO 122
<211> LENGTH: 21
<212> TYPE: DNA
<213> ORGANISM: Homo sapiens

<400> SEQUENCE: 122
aagggcactc ccagccctct t                                             21
```

```
<210> SEQ ID NO 123
<211> LENGTH: 21
<212> TYPE: DNA
<213> ORGANISM: Homo sapiens

<400> SEQUENCE: 123
aagctggccg ccaggtacat a                                              21

<210> SEQ ID NO 124
<211> LENGTH: 21
<212> TYPE: DNA
<213> ORGANISM: Homo sapiens

<400> SEQUENCE: 124
aactggacca aggctctcag a                                              21

<210> SEQ ID NO 125
<211> LENGTH: 19
<212> TYPE: DNA
<213> ORGANISM: Homo sapiens

<400> SEQUENCE: 125
agcctggact tcgatgaga                                                 19

<210> SEQ ID NO 126
<211> LENGTH: 19
<212> TYPE: DNA
<213> ORGANISM: Homo sapiens

<400> SEQUENCE: 126
actcgtatgc cacgctcat                                                 19

<210> SEQ ID NO 127
<211> LENGTH: 19
<212> TYPE: DNA
<213> ORGANISM: Homo sapiens

<400> SEQUENCE: 127
tcgtatgcca cgctcatct                                                 19

<210> SEQ ID NO 128
<211> LENGTH: 19
<212> TYPE: DNA
<213> ORGANISM: Homo sapiens

<400> SEQUENCE: 128
tctacaagtg gatcacgga                                                 19

<210> SEQ ID NO 129
<211> LENGTH: 19
<212> TYPE: DNA
<213> ORGANISM: Homo sapiens

<400> SEQUENCE: 129
tggatcacgg acaacttct                                                 19

<210> SEQ ID NO 130
<211> LENGTH: 19
<212> TYPE: DNA
<213> ORGANISM: Homo sapiens

<400> SEQUENCE: 130
ggatcacgga caacttctg                                                 19
```

```
<210> SEQ ID NO 131
<211> LENGTH: 19
<212> TYPE: DNA
<213> ORGANISM: Homo sapiens

<400> SEQUENCE: 131
tactcgtatg ccacgctca                                              19

<210> SEQ ID NO 132
<211> LENGTH: 21
<212> TYPE: DNA
<213> ORGANISM: Homo sapiens

<400> SEQUENCE: 132
aacgagggcc caggaccaga a                                           21

<210> SEQ ID NO 133
<211> LENGTH: 21
<212> TYPE: DNA
<213> ORGANISM: Homo sapiens

<400> SEQUENCE: 133
aaccggctaa aggaccctgc a                                           21

<210> SEQ ID NO 134
<211> LENGTH: 21
<212> TYPE: DNA
<213> ORGANISM: Homo sapiens

<400> SEQUENCE: 134
aagcccgact tgaggctgag a                                           21

<210> SEQ ID NO 135
<211> LENGTH: 21
<212> TYPE: DNA
<213> ORGANISM: Homo sapiens

<400> SEQUENCE: 135
aatccgccac aacctgtctc t                                           21

<210> SEQ ID NO 136
<211> LENGTH: 21
<212> TYPE: DNA
<213> ORGANISM: Homo sapiens

<400> SEQUENCE: 136
aactgggagg gatgccgagc t                                           21

<210> SEQ ID NO 137
<211> LENGTH: 19
<212> TYPE: DNA
<213> ORGANISM: Homo sapiens

<400> SEQUENCE: 137
tcactgcata gtcgattca                                              19

<210> SEQ ID NO 138
<211> LENGTH: 19
<212> TYPE: DNA
<213> ORGANISM: Homo sapiens

<400> SEQUENCE: 138
agctcttggt ggatcatca                                              19
```

```
<210> SEQ ID NO 139
<211> LENGTH: 19
<212> TYPE: DNA
<213> ORGANISM: Homo sapiens

<400> SEQUENCE: 139
gctcttggtg gatcatcaa                                               19

<210> SEQ ID NO 140
<211> LENGTH: 19
<212> TYPE: DNA
<213> ORGANISM: Homo sapiens

<400> SEQUENCE: 140
ggacaatagc aacaagtat                                               19

<210> SEQ ID NO 141
<211> LENGTH: 19
<212> TYPE: DNA
<213> ORGANISM: Homo sapiens

<400> SEQUENCE: 141
atagcaacaa gtataccaa                                               19

<210> SEQ ID NO 142
<211> LENGTH: 19
<212> TYPE: DNA
<213> ORGANISM: Homo sapiens

<400> SEQUENCE: 142
cgaatcagct gacgacagt                                               19

<210> SEQ ID NO 143
<211> LENGTH: 19
<212> TYPE: DNA
<213> ORGANISM: Homo sapiens

<400> SEQUENCE: 143
acgtgatgct tcgcaatga                                               19

<210> SEQ ID NO 144
<211> LENGTH: 19
<212> TYPE: DNA
<213> ORGANISM: Homo sapiens

<400> SEQUENCE: 144
agaacttgct ccaccacca                                               19

<210> SEQ ID NO 145
<211> LENGTH: 19
<212> TYPE: DNA
<213> ORGANISM: Homo sapiens

<400> SEQUENCE: 145
agccgtgcct tgtcgaatt                                               19

<210> SEQ ID NO 146
<211> LENGTH: 19
<212> TYPE: DNA
<213> ORGANISM: Homo sapiens

<400> SEQUENCE: 146
gtcagccagt ctatgcaaa                                               19
```

```
<210> SEQ ID NO 147
<211> LENGTH: 21
<212> TYPE: DNA
<213> ORGANISM: Homo sapiens

<400> SEQUENCE: 147
aacccagcag agactgttaa t                                              21

<210> SEQ ID NO 148
<211> LENGTH: 21
<212> TYPE: DNA
<213> ORGANISM: Homo sapiens

<400> SEQUENCE: 148
aatgtgacat ggagtccatt a                                              21

<210> SEQ ID NO 149
<211> LENGTH: 21
<212> TYPE: DNA
<213> ORGANISM: Homo sapiens

<400> SEQUENCE: 149
aagcacagag ttggatgaag t                                              21

<210> SEQ ID NO 150
<211> LENGTH: 21
<212> TYPE: DNA
<213> ORGANISM: Homo sapiens

<400> SEQUENCE: 150
aactgccacg gctgactgat a                                              21

<210> SEQ ID NO 151
<211> LENGTH: 21
<212> TYPE: DNA
<213> ORGANISM: Homo sapiens

<400> SEQUENCE: 151
aacgtgatgc ttcgcaatga t                                              21

<210> SEQ ID NO 152
<211> LENGTH: 21
<212> TYPE: DNA
<213> ORGANISM: Homo sapiens

<400> SEQUENCE: 152
aaccagggaa gtttggtcaa t                                              21

<210> SEQ ID NO 153
<211> LENGTH: 21
<212> TYPE: DNA
<213> ORGANISM: Homo sapiens

<400> SEQUENCE: 153
aagtggacag tgataccgtt t                                              21

<210> SEQ ID NO 154
<211> LENGTH: 21
<212> TYPE: DNA
<213> ORGANISM: Homo sapiens

<400> SEQUENCE: 154
aatcccacgc cattttccta a                                              21
```

```
<210> SEQ ID NO 155
<211> LENGTH: 21
<212> TYPE: DNA
<213> ORGANISM: Homo sapiens

<400> SEQUENCE: 155
aacggctcac tctgtcccag a                                              21

<210> SEQ ID NO 156
<211> LENGTH: 21
<212> TYPE: DNA
<213> ORGANISM: Homo sapiens

<400> SEQUENCE: 156
aagggcgaca gcaacagctc t                                              21

<210> SEQ ID NO 157
<211> LENGTH: 21
<212> TYPE: DNA
<213> ORGANISM: Homo sapiens

<400> SEQUENCE: 157
aaccaactct ccttctctct t                                              21

<210> SEQ ID NO 158
<211> LENGTH: 21
<212> TYPE: DNA
<213> ORGANISM: Homo sapiens

<400> SEQUENCE: 158
aactctcctt ctctcttctt t                                              21

<210> SEQ ID NO 159
<211> LENGTH: 21
<212> TYPE: DNA
<213> ORGANISM: Homo sapiens

<400> SEQUENCE: 159
aagtctacgg gtgccagatc a                                              21

<210> SEQ ID NO 160
<211> LENGTH: 21
<212> TYPE: DNA
<213> ORGANISM: Homo sapiens

<400> SEQUENCE: 160
aagtggagct ggacccggag t                                              21

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
accttcttgg tgcgcgac                                                  18

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 162
aagccatctt cacgctgagc                                                 20

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 163
tcgccaacgg aactgcttct tcg                                             23

<210> SEQ ID NO 164
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gagtcgacat gaaggaccac cgcatct                                         27

<210> SEQ ID NO 165
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
accaagctta tccatggcag ccagctg                                         27

<210> SEQ ID NO 166
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
attaacaagc ttggtgtcac ctcggc                                          26

<210> SEQ ID NO 167
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
ttaattgcgg ccgcttagtg ggctg                                           25

<210> SEQ ID NO 168
<211> LENGTH: 96
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 168
tagtcgacct cgagatgctc ctggctgttt tgtactgcct gctgtggagt ttccagacct      60
ccgctggcca tttccctaga atggcacaag tcatta                               96

<210> SEQ ID NO 169
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
ggctctagag cggccgctta acgcagtaaa gagagg                               36

<210> SEQ ID NO 170
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
aattgcggcc gctaaattcc gcccctct                                        28

<210> SEQ ID NO 171
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
ggcctcgagt gtggccatat tatcatcg                                        28

<210> SEQ ID NO 172
<211> LENGTH: 10
<212> TYPE: PRT
<213> ORGANISM: Homo sapiens

<400> SEQUENCE: 172

Glu Leu Thr Leu Gly Glu Phe Leu Lys Leu
1               5                   10

<210> SEQ ID NO 173
<211> LENGTH: 9
<212> TYPE: PRT
<213> ORGANISM: Homo sapiens

<400> SEQUENCE: 173

Ser Thr Ala Pro Pro Ala His Gly Val
1               5

<210> SEQ ID NO 174
<211> LENGTH: 552
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Met Ala Gln Val Ile Asn Thr Asn Ser Leu Ser Leu Leu Thr Gln Asn
1               5                   10                  15
```

-continued

```
Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
    370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
```

```
                435             440              445
Ser Ala Arg Ser Arg Ile Glu Asp Ser Asp Tyr Ala Thr Glu Val Ser
    450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg Met
                485                 490                 495

Ala Arg Tyr Arg Cys Cys Arg Ser Gln Ser Arg Ser Arg Tyr Tyr Arg
            500                 505                 510

Gln Arg Gln Arg Ser Arg Arg Arg Arg Arg Ser Cys Gln Thr Arg
    515                 520                 525

Arg Arg Ala Met Arg Cys Cys Arg Pro Gly Phe Ser Ser Ile Ser Ala
    530                 535                 540

His His His His His His His
545                 550
```

```
<210> SEQ ID NO 175
<211> LENGTH: 21
<212> TYPE: DNA
<213> ORGANISM: Mus sp.

<400> SEQUENCE: 175
ctacctgagt tccttcccct t                                            21

<210> SEQ ID NO 176
<211> LENGTH: 19
<212> TYPE: DNA
<213> ORGANISM: Homo sapiens

<400> SEQUENCE: 176
cacgcacttc cgcacattc                                               19

<210> SEQ ID NO 177
<211> LENGTH: 19
<212> TYPE: DNA
<213> ORGANISM: Mus sp.

<400> SEQUENCE: 177
caaagcactt attgacaga                                               19

<210> SEQ ID NO 178
<211> LENGTH: 19
<212> TYPE: DNA
<213> ORGANISM: Homo sapiens

<400> SEQUENCE: 178
ccatgcaccg atacacact                                               19
```

DENDRITIC CELL VACCINE COMPOSITIONS AND USES OF SAME

CROSS-REFERENCE TO RELATED APPLICATIONS

This application is a U.S. national stage application of International Application No. PCT/US2008/084916, filed on Nov. 26, 2008, which claims the benefit of priority to U.S. Provisional Patent Application No. 60/991,478, filed Nov. 30, 2007, the contents of which are incorporated herein by reference in their entirety.

STATEMENT REGARDING FEDERALLY SPONSORED RESEARCH

The invention was made with United States government support awarded by the following agencies: NIH (CA90427, CA116677). The United States has certain rights in this invention.

TECHNICAL FIELD

The present technology relates generally to vaccine compositions useful in the treatment and/or prevention of disease. In particular, the present technology relates to vaccine compositions and adjuvants comprising a proinflammatory molecule and an inhibitor of a negative immune regulator.

BACKGROUND

The following description is provided to assist the understanding of the reader. None of the information provided or references cited is admitted to be prior art to the present invention.

The ability of T cells to recognize an antigen is dependent on the association of the antigen with either major histocompatibility complex (MHC) I or MHC II proteins. For example, cytotoxic T cells respond to an antigen that is presented in association with MHC-I proteins. Thus, a cytotoxic T cell that should kill a virus-infected cell will not kill that cell if the cell does not also express the appropriate MHC-I protein. Helper T cells recognize MHC-II proteins. Helper T cell activity depends, in general, on both the recognition of the antigen on antigen presenting cells and the presence on these cells of "self" MHC-II proteins. The requirement for recognition of an antigen in association with a self-MHC protein is called MHC restriction. MHC-I proteins are found on the surface of virtually all nucleated cells. MHC-II proteins are found on the surface of certain cells including macrophages, B cells, and dendritic cells of the spleen and Langerhans cells of the skin.

One step in mounting an immune response in mammals is the activation of CD4+ helper T-cells that recognize MHC-II restricted exogenous antigens. These antigens are captured and processed in the cellular endosomal pathway in antigen presenting cells, such as dendritic cells (DCs). In the endosome and lysosome, the antigen is processed into small antigenic peptides that are complexed onto the MHC-II in the Golgi compartment to form an antigen-MHC-II complex. This complex is expressed on the cell surface, which induces the activation of CD4+ T cells.

Other events in the induction of an effective immune response in a mammal involve the activation of CD8+ T-cells and B cells. CD8+ cells are activated when the desired protein is routed through the cell in such a manner so as to be presented on the cell surface as a processed protein, which is complexed with MHC-I antigens. B cells can interact with the antigen via their surface immunoglobulins (IgM and IgD) without the need for MHC proteins. However, the activation of the CD4+ T-cells stimulates all arms of the immune system. Upon activation, CD4+ T-cells (helper T cells) produce interleukins. These interleukins help activate the other arms of the immune system. For example, helper T cells produce interleukin-4 (IL-4) and interleukin-5 (IL-5), which help B cells produce antibodies; interleukin-2 (IL-2), which activates CD4+ and CD8+ T-cells; and gamma interferon, which activates macrophages. Since helper T-cells that recognize MHC-II restricted antigens play a central role in the activation and clonal expansion of cytotoxic T-cells, macrophages, natural killer cells and B cells, the initial event of activating the helper T cells in response to an antigen is important for the induction of an effective immune response directed against that antigen.

In addition to the roles that T cells play in the immune response, DCs are equally important. DCs are professional antigen-presenting cells having a key regulatory role in the maintenance of tolerance to self-antigens and in the activation of innate and adaptive immunity (Banchereau et al., 1998, *Nature* 392:245-52; Steinman et al., 2003, *Annu. Rev. Immunol.* 21:685-711). When DCs encounter pro-inflammatory stimuli such as microbial products, the maturation process of the cell is initiated by up-regulating cell surface expressed antigenic peptide-loaded MHC molecules and co-stimulatory molecules. Following maturation and homing to local lymph nodes, DCs establish contact with T cells by forming an immunological synapse, where the T cell receptor (TCR) and co-stimulatory molecules congregate in a central area surrounded by adhesion molecules (Dustin et al., 2000, *Nat. Immunol.* 1:23-9). Once activated, CD8+ T cells can autonomously proliferate for several generations and acquire cytotoxic function without further antigenic stimulation (Kaech et al., 2001, *Nat. Immunol.* 2:415-22; van Stipdonk et al., 2001, *Nat. Immunol.* 2:423-9). It has therefore been proposed that the level and duration of peptide-MHC complexes (signal 1) and co-stimulatory molecules (signal 2) provided by DCs are essential for determining the magnitude and fate of an antigen-specific T cell response (Lanzavecchia et al., 2001, *Nat. Immunol.* 2:487-92; Gett et al., 2003, *Nat. Immunol.* 4:355-60).

SUMMARY

The present invention relates to compositions and methods for stimulating an immune response in mammals. As the results shown in the Examples demonstrate, these adjuvants are capable of enhancing immune responses in a synergistic fashion. Therefore, the present invention provides a therapeutic benefit by enhancing the immunostimulatory capacity of the cell for a particular antigen. In one aspect, the present invention provides an adjuvant composition comprising polynucleotides encoding (a) an inhibitor of a negative immune regulator in a cell, wherein the negative immune regulator is selected from the group consisting of a suppressor of cytokine signaling (SOCS), a protein involved in molecular stability, and a transcription factor that induces the expression of inhibitors of NF-κB or suppresses transcription of NF-κB targeted genes; and (b) a flagellin polypeptide; wherein the polynucleotides are provided on the same or different expression vectors. In one embodiment, the flagellin polypeptide is operably linked to a secretory signal sequence.

In one embodiment, the negative immune regulator is a SOCS selected from the group consisting of: SOCS1, SOCS2, SOCS3, SOCS4, SOCS5, SOCS6, SOCS7 and a cytokine-inducible SH2-domain-containing protein (CIS). In another embodiment, the negative immune regulator is an A20 protein. In some embodiments, the inhibitor of a negative immune regulator may be an antisense RNA or a ribozyme. In a particular embodiment, the inhibitor of a negative immune regulator in a cell is a siRNA.

The expression vector may be selected from the group consisting of a plasmid DNA, a viral vector (e.g., an adenoviral vector), a bacterial vector and a mammalian vector. In one embodiment, the expression vector further comprises an integration signal sequence which facilitates integration of the isolated polynucleotides into the genome of a host cell.

In some embodiments, the composition further comprises one or more antigens or polynucleotides encoding the one or more antigens. In one embodiment, the antigen is associated with an infectious disease, including, but not limited to those caused by viruses, bacteria, fungi, and protozoans. In a particular embodiment, the antigen may be from a virus, e.g., a hepatitis B virus, a hepatitis C virus, a human immunodeficiency virus, a papillomavirus, or a herpesvirus. Specific examples of viral antigens, include, but are not limited to hepatitis B virus e antigen gene, a hepatitis B virus surface antigen gene, a hepatitis B virus core antigen gene, human immunodeficiency virus Env gp160 gene, Gag gene, Pol gene, Rev gene, Tat gene, Vif gene, Nef gene, and combinations thereof.

In one embodiment, the antigen encoded by the polynucleotide is a tumor-associated antigen. For example, the tumor associated antigen may be selected from the group consisting of: an overexpressed tumor-associated antigen, a testis-tumor antigen, a mutated tumor-associated antigen, a differentiation tumor-associated antigen tyrosinase, MART, trp, MAGE-1, MAGE-2, MAGE-3, gp100, HER-2, Ras, PSA BCR-ABL, CASP, CDK, Ras, p53, HER-2/neu, CEA, MUC, TW1, PAP, survivin, telomerase, EGFR, PSMA, PSA, PSCA, tyrosinase, MART, TRP, gp100, MART, MAGE, BAGE, GAGE, LAGE/NY-ESO, RAGE, SSX-2, CD19, CD20, and combinations thereof. In particular embodiments, the tumor-associated antigen is survivin and/or MUC1. Where the tumor-associated antigen is survivin, the polynucleotide may encode a variant survivin, e.g., a dominant negative survivin mutant. Where the tumor-associated antigen is MUC1, the polynucleotide may encode a fragment of MUC1, e.g., a fragment comprising a dominant T cell epitope.

In one embodiment, the present invention provides a vaccine composition comprising an expression vector comprising polynucleotides encoding: (a) an inhibitor of SOCS1 or A20; (b) at least one antigen, wherein each antigen has at least one epitope capable of eliciting an immune response in a mammal; and (c) a flagellin polypeptide operably linked to a secretory signal sequence. The inhibitor of SOCS1 or A20 may be a siRNA, capable of specifically interfering with the expression of SOCS1 or A20, respectively. In a particular embodiment, the polynucleotide encoding the siRNA has a sequence according to SEQ ID NO: 5.

In one embodiment, the compositions comprise polynucleotides encoding antigens corresponding to the tumor-associated antigens survivin and MUC1. In a particular embodiment, the antigens are expressed as a fusion protein, such as the fusion protein encoded by the polynucleotide of SEQ ID NO: 2. In one embodiment, the one or more antigens are associated with a pathogen. For example, the antigens may be encoded as a fusion of HCV E1 and E2 proteins comprising a dominant T cell epitope and B cell epitope.

In one embodiment, the compositions comprise polynucleotides encoding a flagellin polypeptide operably linked to a secretory signal sequence. For example, the flagellin polypeptide may have a sequence according to SEQ ID NO:3.

In another aspect, the present invention provides cells comprising one or more expression vectors with polynucleotides encoding: (a) a siRNA inhibitor of SOCS1 or A20; (b) a flagellin polypeptide operably linked to a secretory signal sequence, and optionally (c) one or more antigens. In some embodiments, the cells are immune cells. In particular embodiments, the immune cells are antigen presenting cells, e.g., dendritic cells.

In another aspect, the present invention provides a composition comprising: (a) an inhibitor of a negative immune regulator in a cell, wherein the negative immune regulator is selected from the group consisting of a suppressor of cytokine signaling (SOCS), a protein involved in molecular stability, and a transcription factor that induces the expression of inhibitors of NF-κB or suppresses transcription of NF-κB targeted genes; and (b) a flagellin polypeptide covalently linked to a protamine polypeptide, wherein the protamine polypeptide is capable of binding to the siRNA inhibitor. In particular embodiments, the inhibitor of a negative immune regulator is a siRNA inhibitor of SOCS1 or A20. In some embodiments, the composition further comprises one or more antigens having at least one epitope, wherein the epitope is capable of eliciting an immune response in a mammal. In a particular embodiment, the flagellin polypeptide covalently linked to a protamine polypeptide has a sequence according to SEQ ID NO: 174.

In another aspect, the present invention provides methods of generating a silenced and pulsed cell comprising contacting a cell an expression vector comprising polynucleotides encoding: (a) an inhibitor of a negative immune regulator in a cell, wherein the negative immune regulator is selected from the group consisting of a suppressor of cytokine signaling (SOCS), a protein involved in molecular stability, and a transcription factor that induces the expression of inhibitors of NF-κB or suppresses transcription of NF-κB targeted genes (e.g., SOCS1 or A20); (b) at least one antigen, wherein each antigen has at least one epitope capable of eliciting an immune response in a mammal; and (c) a flagellin polypeptide operably linked to a secretory signal sequence. In some embodiments, the cells are immune cells. In particular embodiments, the immune cells are antigen presenting cells, e.g., dendritic cells.

In another aspect, the present invention provides methods of eliciting an immune response in a mammal comprising administering to the mammal an expression vector comprising polynucleotides encoding: (a) an inhibitor of SOCS1 or A20; (b) at least one antigen, wherein each antigen has at least one epitope capable of eliciting an immune response in a mammal; and (c) a flagellin polypeptide operably linked to a secretory signal sequence. The expression vector(s) may also be contacted with APCs ex vivo prior to administration of the APCs to the mammal. The methods also provide for eliciting an immune response by administering to a mammal a composition comprising: (a) an inhibitor of a negative immune regulator in a cell, wherein the negative immune regulator is selected from the group consisting of a suppressor of cytokine signaling (SOCS), a protein involved in molecular stability, and a transcription factor that induces the expression of inhibitors of NF-κB or suppresses transcription of NF-κB targeted genes; and (b) a flagellin polypeptide covalently linked to a protamine polypeptide, wherein the protamine polypeptide is capable of binding to the siRNA inhibitor.

In another aspect, the present invention provides methods of treating cancer in a mammal comprising administering to a mammal in need thereof an antigen presenting cell comprising an expression vector, wherein the expression vector comprises polynucleotides encoding: (a) a siRNA inhibitor of SOCS1 or A20; (b) a dominant negative survivin mutant and a MUC1 fragment comprising a dominant T cell epitope; and (c) a flagellin polypeptide operably linked to a secretory signal sequence, wherein the polynucleotides are expressed by the antigen presenting cell, thereby producing an immune response against cancer cells in the mammal. The expression vectors may also be administered to the mammal directly.

BRIEF DESCRIPTION OF THE DRAWINGS

FIG. 2 is a western blot analysis of the effect of SOCS1 siRNA in transfected 293T cells. FIG. 2A is a quantitative analysis of the western blot in FIG. 2B by densitometry. Relative levels of hSOCS1 and actin in each cell lysate are presented.

FIG. 13A is a graph of flow cytometry data showing enhanced TAA-specific CTL cytolytic activity against human tumor cells. The surface expression of HLA-A2 and MUC1 on human tumor cell lines was examined by flow cytometric assays.

FIG. 14 is a series of graphs presenting the results standard $^{51}$Cr release assays, which show the cytolytic activities of HLA-A2+ T cells against various human tumor cell lines after two week in vitro sensitization by different Ad-transfected autologous DCs. The cytolytic percentages are presented from one of three repeated experiments. *P<0.05, Ad-siSSF vs. Ad-SM.

FIG. 20 is a series of charts showing the superior potency of Ad-shS1/FliC in persistently stimulating mouse and human DCs. Murine BM-DCs (FIGS. 20A-20E) and human PBMC-derived DCs (FIGS. 20E-20I) were transduced with Ad vectors at an MOI of 250 ifu or stimulated with commonly used TLR agonists (Poly I:C (1 µg/ml), CpG (1 µM), Imiquimod (10 µg/ml), or LPS (100 ng/ml)), respectively.

FIG. 23 is a series of charts showing the superior potency of Ad-shA20/FliC in stimulating antigen-specific T cell responses by DCs.

FIG. 27 is a series of charts showing enhanced levels of inflammatory cytokine production by FliC-P/siA20.

DETAILED DESCRIPTION

Figure 1:
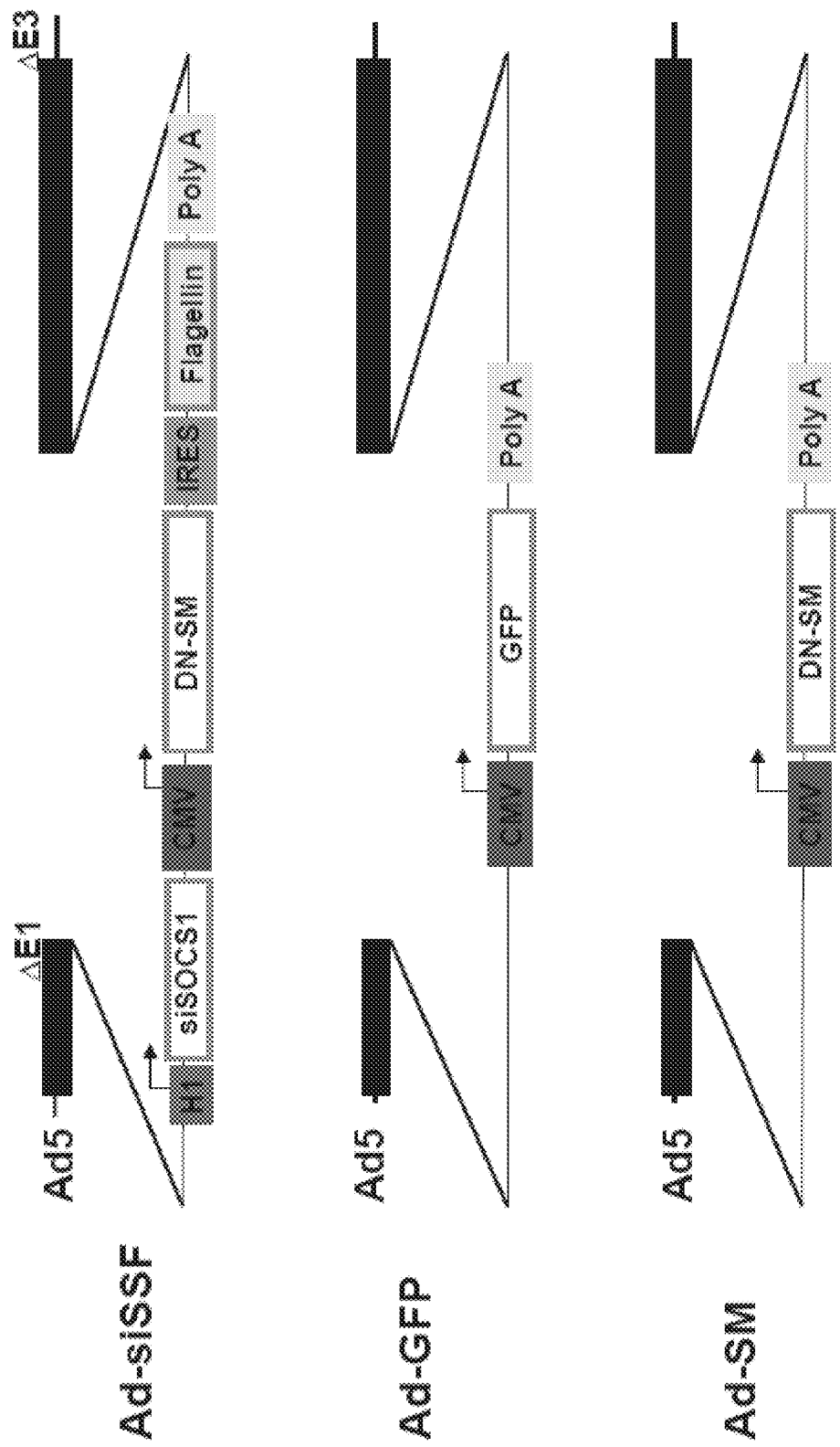
FIG. 1 is a schematic diagram of recombinant adenovirus constructs Ad-siSSF, Ad-GFP, and Ad-SM.

General. It is to be appreciated that certain aspects, modes, embodiments, variations and features of the invention are described below in various levels of detail in order to provide a substantial understanding of the present invention.

Intensive efforts have been devoted to develop Toll-like receptor (TLR) agonists as adjuvants to improve vaccine efficacy, since antigen-presenting cells (APCs), such as dendritic cells (DCs), use TLRs to sense conserved structural moieties of pathogens for the activation of proinflammatory gene cascades, and innate and adaptive immune responses. Provided herein are vaccine compositions and adjuvants that stimulate a high degree of immunopotency.

The present invention provides vaccines and therapies in which the immunopotency of an immune cell is enhanced by compositions including an inhibitor of a negative immune regulator and a proinflammatory molecule. As the results shown in the Examples demonstrate, these adjuvants are capable of enhancing immune responses in a synergistic fashion. Therefore, the present invention provides a therapeutic benefit by enhancing the immunostimulatory capacity of the cell for a particular antigen. Negative regulators of cytokine receptor and TLR signaling, such as the suppressor of cytokine signaling (SOCS) 1 and A20, negatively regulate the maturation, inflammatory cytokine production, and immunostimulatory potency of DCs, functioning as critical antigen presentation attenuators. Accordingly, a new type of vaccine adjuvant including an inhibitor of the negative immune regulator and a flagellin polypeptide is described.

In one aspect, immune cells are transfected with the compositions (adjuvants) of the present invention. In one embodiment, the immune cells are dendritic cells (DCs). While not wishing to be limited by theory, DCs are the most potent of professional antigen-presenting cells (APC) and have a unique capacity to prime adaptive immune responses against pathogens and tumor-associated antigens (TAA). DC vaccines have been tested in mouse tumor models and in clinical trials. However, DC vaccinations rarely cause tumor regression (objective clinical response) or autoimmune pathologies, suggesting that self-tolerance at the host level is still maintained in immunized patients. Likewise, pathogens associated with chronic infections such as hepatitis C virus (HCV) are refractory to the immune responses that are induced either by vaccination or natural infection of pathogens that contain TLR ligands themselves. There are many possible explanations for the general ineffectiveness of DC vaccines, including inefficient antigen loading and DC maturation, the heterogeneous nature of DC populations, tumor-mediated immunosuppression, self-tolerance of autoreactive, low avidity T cells to TAAs, and suppression by regulatory T cells.

The vaccine adjuvants of the invention have the advantage of overcoming some of the problems associated with DC vaccines. The adjuvants may comprise an inhibitor of a negative immune regulator. In one embodiment, the negative immune regulator is a suppressor of cytokine signaling 1 (SOCS1). SOCS1 is an antigen-presentation attenuator (APA) in maintaining self tolerance and limiting antitumor immunity (See U.S. Patent Application Publication Nos. 2006/0292119 and 2006/0269519, incorporated herein by reference). SOCS1, a member of the SOCS family, is an essential negative regulator of signaling by various proinflammatory cytokines, including IFN-γ, IL-2, IL-6, IL-7, IL-12, IL-15 and others, in T cells and APCs. (Kubo et al., *Nat Immunol*, 4: 1169-1176, 2003; Alexander et al., *Annu Rev Immunol*, 22: 503-529, 2004.) SOCS1 is inducibly expressed after proinflammatory stimulation in a feedback manner and acts as a pseudosubstrate to block JAK and STAT binding and as an E3 ligase to promote JAK ubiquitination for its degradation (Yoshimura et al., *Nat Rev Immunol*, 7: 454-465, 2007). In addition, SOCS1 negatively regulates TLR signaling by promoting Mal polyubiquitination and subsequent degradation (Mansell et al., *Nat Immunol*, 7: 148-155, 2006).

While inhibition of SOCS1 helps to break self-tolerance, inhibitors of SOCS1 alone are insufficient to activate DCs. The present inventors have discovered that proinflammatory stimuli, such as a flagellin polypeptide, are additionally required to initiate proinflammatory signaling cascades. Flagellin is the ligand for TLR5 and induces maturation and chemokine production of human DCs via its interaction with TLR5. Therefore, in one aspect, the present invention provides vaccine adjuvants with polynucleotides encoding an inhibitor of a negative immune regulator, and a flagellin polypeptide.

In one embodiment, the adjuvant composition includes one or more polynucleotides encoding an inhibitor of SOCS1 (e.g., a siRNA of SOCS1) and a polynucleotide encoding a flagellin polypeptide. Polynucleotide constructs encoding the SOCS1 inhibitor and the flagellin polypeptide are shown in Tables 1 and 3, respectively.

In some embodiments, the compositions further comprise an antigen. In select embodiments, the vaccine composition comprise one or more polynucleotides encoding an inhibitor of SOCS1 (e.g., a siRNA of SOCS1), a polynucleotide encoding a dominant negative (DN) survivin mutant polypeptide and a MUC1 fragment, and a polynucleotide encoding a flagellin polypeptide. Polynucleotide constructs encoding the SOCS1 inhibitor, the DN survivin mutant and MUC1 fragment, and the flagellin polypeptide are shown in Tables 1-3, respectively. In some embodiments, the DN survivin mutant and the MUC1 fragment are expressed separately or together. In one embodiment, the nucleotides encoding the DN survivin mutant comprise nucleotides 1 to 387 of SEQ ID NO: 2. In one embodiment, the nucleotides encoding a MUC1 fragment comprise nucleotide 394 to 573 of SEQ ID NO: 2. In a particular embodiment, the DN survivin mutant and MUC1 fragment are expressed as a fusion protein, e.g., by the sequence according to SEQ ID NO: 2.

TABLE 1

Sequence of H1 Promoter Construct Encoding siRNA of SOCS1

(SEQ ID NO: 1)
ATTTGCATGTCGCTATGTGTTCTGGGAAATCACCATAAACGTGAAAT

GTCTTTGGATTTGGGAATCTTATAAGTTCTGTATGAGACCACAGATC

CCCCAGCACTTCCGCACATTCTTCAAGAGAGAATGTGCGGAAGTGCG

TGTTTTTGGAAAGCTTATCGA

TABLE 2

Sequence of Polynucleotide Encoding DN Survivin Mutant and MUC1 Antigenic Fragment (SEQ ID NO: 2)
ATGAAGGACCACCGCATCTCTACATTCAAGAACTGGCCCTTCTTGGA

GGGCTGCGCCTGCGCCCCGGAGCGGATGGCCGAGGCTGGCTTCATCC

ACTGCCCCACTGAGAACGAGCCAGACTTGGCCCAGTGTTTCTTCTGT

TTCAAGGAGCTGGAAGGCTGGGAGCCGGATGACGACCCCATAGAGGA

ACATAAAAAGCATTCATCCGGTTGCGCTTTCCTTTCTGTCAAGAAGC

AGTTTGAAGAATTAACCCTCGGTGAATTTTTGAAACTGGACAGAGAA

AGAGCCAAGAACAAAATTGCAAAGGAAACCAACAATAAGAAGAAAGA

ATTTGAGGAAACTGCAAAGAAAGTGCGCCGTGCCATCGAGCAGCTGG

CTGCCATGGATAAGCTTGGTGTCACCTCGGCCCCGGACACCAGGCCG

GCCCCGGGCTCCACCGCCCCCCCAGCCCACGTGTCACCTCGGCCCC

GGACACCAGGCCGGCCCCGGGCTCCACCTCCCCCCCAGCCCACGGTG

TCACCTCGGCCCCGGACACCAGGCCGGCCCCGGGCTCCACCGCCCCC

CCAGCCCACTAA

TABLE 3

Sequence of Polynucleotide Encoding Flagellin Linked to a Secretory Signal Sequence (SEQ ID NO: 3)
ATGCTCCTGGCTGTTTTGTACTGCCTGCTGTGGAGTTTCCAGACCTC

CGCTGGCCATTTCCCTAGAATGGCACAAGTCATTAATACAAACAGCC

TGTCGCTGTTGACCCAGAATAACCTGAACAAATCCCAGTCCGCTCTG

GGCACCGCTATCGAGCGTCTGTCTTCCGGTCTGCGTATCAACAGCGC

GAAAGACGATGCGGCAGGTCAGGCGATTGCTAACCGTTTTACCGCGA

ACATCAAAGGTCTGACTCAGGCTTCCCGTAACGCTAACGACGGTATC

TCCATTGCGCAGACCACTGAAGGCGCGCTGAACGAAATCAACAACAA

TABLE 3-continued

Sequence of Polynucleotide Encoding Flagellin Linked to a Secretory Signal Sequence

CCTGCAGCGTGTGCGTGAACTGGCGGTTCAGTCTGCTAACAGCACCA

ACTCCCAGTCTGACCTCGACTCCATCCAGGCTGAAATCACCCAGCGC

CTGAACGAAATCGACCGTGTATCCGGCCAGACTCAGTTCAACGGCGT

GAAAGTCCTGGCGCAGGACAACACCCTGACCATCCAGGTTGGTGCCA

ACGACGGTGAAACTATCGATATCGATCTGAAGCAGATCAACTCTCAG

ACCCTGGGTCTGGATACGCTGAATGTGCAACAAAAATATAAGGTCAG

CGATACGGCTGCAACTGTTACAGGATATGCCGATACTACGATTGCTT

TAGACAATAGTACTTTTAAAGCCTCGGCTACTGGTCTTGGTGGTACT

GACCAGAAAATTGATGGCGATTTAAAATTTGATGATACGACTGGAAA

ATATTACGCCAAAGTTACCGTTACGGGGGGAACTGGTAAAGATGGCT

ATTATGAAGTTTCCGTTGATAAGACGAACGGTGAGGTGACTCTTGCT

GGCGGTGCGACTTCCCCGCTTACAGGTGGACTACCTGCGACAGCAAC

TGAGGATGTGAAAAATGTACAAGTTGCAAATGCTGATTTGACAGAGG

CTAAAGCCGCATTGACAGCAGCAGGTGTTACCGGCACAGCATCTGTT

GTTAAGATGTCTTATACTGATAATAACGGTAAAACTATTGATGGTGG

TTTAGCAGTTAAGGTAGGCGATGATTACTATTCTGCAACTCAAAATA

AAGATGGTTCCATAAGTATTAATACTACGAAATACACTGCAGATGAC

GGTACATCCAAAACTGCACTAAACAAACTGGGTGGCGCAGACGGCAA

AACCGAAGTTGTTTCTATTGGTGGTAAAACTTACGCTGCAAGTAAAG

CCGAAGGTCACAACTTTAAAGCACAGCCTGATCTGGCGGAAGCGGCT

GCTACAACCACCGAAAACCCGCTGCAGAAAATTGATGCTGCTTTGGC

ACAGGTTGACACGTTACGTTCTGACCTGGGTGCGGTACAGAACCGTT

TCAACTCCGCTATTACCAACCTGGGCAACACCGTAAACAACCTGACT

TCTGCCCGTAGCCGTATCGAAGATTCCGACTACGCGACCGAAGTTTC

CAACATGTCTCGCGCGCAGATTCTGCAGCAGGCCGGTACCTCCGTTC

TGGCGCAGGCGAACCAGGTTCCGCAAAACGTCCTCTCTTTACTGCGT

TAAGCG

In an exemplary embodiment, the present invention provides the vaccine composition wherein a SOCS1 siRNA, a DN survivin/MUC1 fusion protein, and a flagellin polypeptide are provided in a single construct. The sequence of this construct is shown in Table 4. In select embodiments, this construct may be inserted into an adenoviral vector (illustrated in FIG. 1).

TABLE 4

Nucleotide Sequence of Ad-siSSF Expression Construct (SEQ ID NO: 4)

```
   1 ATTTGCATGT CGCTATGTGT TCTGGGAAAT CACCATAAAC GTGAAATGTC
  51 TTTGGATTTG GGAATCTTAT AAGTTCTGTA TGAGACCACA GATCCCCCAC
 101 GCACTTCCGC ACATTCTTCA AGAGAGAATG TGCGGAAGTG CGTGTTTTTG
 151 GAAAGCTTAT CGATCATAGC CCATATATGG AGTTCCGCGT TACATAACTT
 201 ACGGTAAATG GCCCGCCTGG CTGACCGCCC AACGACCCCC GCCCATTGAC
 251 GTCAATAATG ACGTATGTTC CCATAGTAAC GCCAATAGGG ACTTTCCATT
 301 GACGTCAATG GGTGGAGTAT TTACGGTAAA CTGCCCACTT GGCAGTACAT
 351 CAAGTGTATC ATATGCCAAG TACGCCCCCT ATTGACGTCA ATGACGGTAA
 401 ATGGCCCGCC TGGCATTATG CCCAGTACAT GACCTTATGG GACTTTCCTA
 451 CTTGGCAGTA CATCTACGTA TTAGTCATCG CTATTACCAT GGTGATGCGG
 501 TTTTTGCAGT ACATCAATGG GCGTGGATAG CGGTTTGACT CACGGGGATT
 551 TCCAAGTCTC CACCCCATTG ACGTCAATGG GAGTTTGTTT TGGCACCAAA
 601 ATCAACGGGA CTTTCCAAAA TGTCGTAACA ACTCCGCCCC ATTGACGCAA
 651 ATGGGCGGTA GGCGTGTACG GTGGGAGGTC TATATAAGCA GAGCTGGTTT
 701 AGTGAACCGT CAGATCCGCT AGGTCGACAT GAAGGACCAC CGCATCTCTA
 751 CATTCAAGAA CTGGCCCTTC TTGGAGGGCT GCGCCTGCGC CCCGGAGCGG
 801 ATGGCCGAGG CTGGCTTCAT CCACTGCCCC ACTGAGAACG AGCCAGACTT
 851 GGCCCAGTGT TTCTTCTGTT TCAAGGAGCT GGAAGGCTGG GAGCCGGATG
 901 ACGACCCCAT AGAGGAACAT AAAAAGCATT CATCCGGTTG CGCTTTCCTT
 951 TCTGTCAAGA AGCAGTTTGA AGAATTAACC CTCGGTGAAT TTTTGAAACT
1001 GGACAGAGAA AGAGCCAAGA ACAAAATTGC AAAGGAAACC AACAATAAGA
1051 AGAAAGAATT TGAGGAAACT GCAAAGAAAG TGCGCCGTGC CATCGAGCAG
1101 CTGGCTGCCA TGGATAAGCT TGGTGTCACC TCGGCCCCGG ACACCAGGCC
1151 GGCCCCGGGC TCCACCGCCC CCCCAGCCCA CGGTGTCACC TCGGCCCCGG
1201 ACACCAGGCC GGCCCCGGGC TCCACCTCCC CCCCAGCCCA CGGTGTCACC
1251 TCGGCCCCGG ACACCAGGCC GGCCCCGGGC TCCACCGCCC CCCAGCCCA
1301 CTAAGGCGGC CGCTAAATTC CGGCCCCTCT CCCTCCCCCC CCCCTAACGT
1351 TACTGGCCGA AGCCGCTTGG AATAAGGCCG GTGTGCGTTT GTCTATATGT
1401 TATTTTCCAC CATATTGCCG TCTTTTGGCA ATGTGAGGGC CCGGAAACCT
1451 GGCCCTGTCT TCTTGACGAG CATTCCTAGG GGTCTTTCCC CTCTCGCCAA
1501 AGGAATGCAA GGTCTGTTGA ATGTCGTGAA GGAAGCAGTT CCTCTGGAAG
1551 CTTCTTGAAG ACAAACAACG TCTGTAGCGA CCCTTTGCAG GCAGCGGAAC
1601 CCCCCACCTG GCGACAGGTG CCTCTGCGGC CAAAAGCCAC GTGTATAAGA
1651 TACACCTGCA AAGGCGGCAC AACCCCAGTG CCACGTTGTG AGTTGGATAG
1701 TTGTGGAAAG AGTCAAATGG CTCTCCTCAA GCGTATTCAA CAAGGGGCTG
1751 AAGGATGCCC AGAAGGTACC CCATTGTATG GGATCTGATC TGGGGCCTCG
1801 GTGCACATGC TTTACATGTG TTTAGTCGAG GTTAAAAAAA CGTCTAGGCC
1851 CCCCGAACCA CGGGGACGTG GTTTTCCTTT GAAAACACG ATGATAATAT
```

TABLE 4-continued

Nucleotide Sequence of Ad-siSSF Expression Construct

```
1901 GGCCACACTC GAGATGCTCC TGGCTGTTTT GTACTGCCTG CTGTGGAGTT
1951 TCCAGACCTC CGCTGGCCAT TTCCCTAGAA TGGCACAAGT CATTAATACA
2001 AACAGCCTGT CGCTGTTGAC CCAGAATAAC CTGAACAAAT CCCAGTCCGC
2051 TCTGGGCACC GCTATCGAGC GTCTGTCTTC CGGTCTGCGT ATCAACAGCG
2101 CGAAAGACGA TGCGGCAGGT CAGGCGATTG CTAACCGTTT TACCGCGAAC
2151 ATCAAAGGTC TGACTCAGGC TTCCCGTAAC GCTAACGACG GTATCTCCAT
2201 TGCGCAGACC ACTGAAGGCG CGCTGAACGA AATCAACAAC AACCTGCAGC
2251 GTGTGCGTGA ACTGGCGGTT CAGTCTGCTA ACAGCACCAA CTCCCAGTCT
2301 GACCTCGACT CCATCCAGGC TGAAATCACC CAGCGCCTGA ACGAAATCGA
2351 CCGTGTATCC GGCCAGACTC AGTTCAACGG CGTGAAAGTC CTGGCGCAGG
2401 ACAACACCCT GACCATCCAG GTTGGTGCCA ACGACGGTGA AACTATCGAT
2451 ATCGATCTGA AGCAGATCAA CTCTCAGACC CTGGGTCTGG ATACGCTGAA
2501 TGTGCAACAA AAATATAAGG TCAGCGATAC GGCTGCAACT GTTACAGGAT
2551 ATGCCGATAC TACGATTGCT TTAGACAATA GTACTTTTAA AGCCTCGGCT
2601 ACTGGTCTTG GTGGTACTGA CCAGAAAATT GATGGCGATT TAAAATTTGA
2651 TGATACGACT GGAAAATATT ACGCCAAAGT TACCGTTACG GGGGGAACTG
2701 GTAAAGATGG CTATTATGAA GTTTCCGTTG ATAAGACGAA CGGTGAGGTG
2751 ACTCTTGCTG GCGGTGCGAC TTCCCCGCTT ACAGGTGGAC TACCTGCGAC
2801 AGCAACTGAG GATGTGAAAA ATGTACAAGT TGCAAATGCT GATTTGACAG
2851 AGGCTAAAGC CGCATTGACA GCAGCAGGTG TTACCGGCAC AGCATCTGTT
2901 GTTAAGATGT CTTATACTGA TAATAACGGT AAAACTATTG ATGGTGGTTT
2951 AGCAGTTAAG GTAGGCGATG ATTACTATTC TGCAACTCAA AATAAAGATG
3001 GTTCCATAAG TATTAATACT ACGAAATACA CTGCAGATGA CGGTACATCC
3051 AAAACTGCAC TAAACAAACT GGGTGGCGCA GACGGCAAAA CCGAAGTTGT
3101 TTCTATTGGT GGTAAAACTT ACGCTGCAAG TAAAGCCGAA GGTCACAACT
3151 TTAAAGCACA GCCTGATCTG GCGGAAGCGG CTGCTACAAC CACCGAAAAC
3201 CCGCTGCAGA AAATTGATGC TGCTTTGGCA CAGGTTGACA CGTTACGTTC
3251 TGACCTGGGT GCGGTACAGA ACCGTTTCAA CTCCGCTATT ACCAACCTGG
3301 GCAACACCGT AAACAACCTG ACTTCTGCCC GTAGCCGTAT CGAAGATTCC
3351 GACTACGCGA CCGAAGTTTC CAACATGTCT CGCGCGCAGA TTCTGCAGCA
3401 GGCCGGTACC TCCGTTCTGG CGCAGGCGAA CCAGGTTCCG CAAAACGTCC
3451 TCTCTTTACT GCGTTAAGCG GCCGCTCTAG ATAAGATATC CGATCCACCG
3501 GATCTAGATA ACTGATCATA ATCAGCCATA CCACATTTGT AGAGGTTTTA
3551 CTTGCTTTAA AAAACCTCCC ACACCTCCCC CTGAACCTGA AACATAAAAT
3601 GAATGCAATT GTTGTTGTTA ACTTGTTTAT TGCAGCTTAT AATGGTTACA
3651 AATAAAGCAA TAGCATCACA AATTTCACAA ATAAAGCATT TTTTTCACTG
3701 CATTCTAGTT GTGGTCCAAC TCATCAATGT ATCTTA
```

In practicing the present invention, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively.

The definitions of certain terms as used in this specification are provided below. Unless defined otherwise, all technical and scientific terms used herein generally have the same meaning as commonly understood by one of ordinary skill in the art to which this invention belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well known and commonly employed in the art. All references cited herein are incorporated herein by reference in their entireties and for all purposes to the same extent as if each individual publication, patent, or patent application was specifically and individually incorporated by reference in its entirety for all purposes.

As used herein, the "administration" of a vaccine, agent or drug to a subject or cell includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another. It is also to be appreciated that various modes of treatment or prevention of medical conditions as described are intended to mean "substantial", which includes total but also less than total treatment or prevention, and wherein some biologically or medically relevant result is achieved.

The term "antibody" as used herein, refers to an immunoglobulin molecule, which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies may exist in a variety of forms including, for example, polyclonal antibodies, monoclonal antibodies, Fv, Fab and F(ab)$_2$, as well as single chain antibodies and humanized antibodies.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen". Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to produce polypeptides which elicit the desired immune response. For example, in one embodiment, polynucleotides encoding antigens corresponding to a DN survivin mutant and a MUC1 fragment are combined to elicit an immune response against both antigens simultaneously. Moreover, a skilled artisan will understand that an antigen need not be encoded by a "gene" at all. It is readily apparent that an antigen can be synthesized or can be derived from a biological sample.

An "antigen presenting cell" (APC) is a cell that is capable of activating T cells, and includes, but is not limited to, monocytes/macrophages, B cells and dendritic cells (DCs).

The term "dendritic cell" or "DC" refers to any member of a diverse population of morphologically similar cell types found in lymphoid or non-lymphoid tissues. These cells are characterized by their distinctive morphology, high levels of surface MHC-class II expression. DCs can be isolated from a number of tissue sources. DCs have a high capacity for sensitizing MHC-restricted T cells and are very effective at presenting antigens to T cells in situ. The antigens may be self-antigens that are expressed during T cell development and tolerance, and foreign antigens that are present during normal immune processes.

As used herein, an "activated DC" is a DC that has been pulsed with an antigen and is capable of activating an immune cell.

The term "mature DC" as used herein, is defined as a dendritic cell that expresses high levels of MHC class II, CD80 (B7.1) and CD86 (B7.2) molecules. In contrast, immature dendritic cells express low levels of MHC class II, CD80 (B7.1) and CD86 (B7.2) molecules but have a great capacity to take up an antigen.

"Antigen-loaded APC" or an "antigen-pulsed APC" includes an APC, which has been exposed to an antigen and activated by the antigen. For example, an APC may become Ag-loaded in vitro, e.g., during culture in the presence of an antigen. The APC may also be loaded in vivo by exposure to an antigen.

An "antigen-loaded APC" is traditionally prepared in one of two ways: (1) small peptide fragments, known as antigenic peptides, are "pulsed" directly onto the outside of the APCs; or (2) the APC is incubated with whole proteins or protein particles which are then ingested by the APC. In another embodiment, the APC may be transfected with the antigen or a polynucleotide encoding the antigen. These proteins are digested into small peptide fragments by the APC and are eventually transported to and presented on the APC surface. In addition, the antigen-loaded APC can also be generated by introducing a polynucleotide encoding an antigen into the cell.

As used herein, the term a "silenced APC" or a "silenced DC" refers to an APC or a DC, respectively, which has been exposed to an inhibitor of a negative immune regulator (otherwise known as inhibiting the negative immune regulator), whereby the negative immune regulator is associated with regulating the immune response. The silenced APC has enhanced immunopotency when compared to an otherwise identical APC that has not been treated with an inhibitor of a negative immune regulator.

"Antisense" refers particularly to the nucleic acid sequence of the non-coding strand of a double stranded DNA molecule encoding a polypeptide, or to a sequence which is substantially homologous to the non-coding strand. As defined herein, an antisense sequence is complementary to the sequence of a double stranded DNA molecule encoding a polypeptide. It is not necessary that the antisense sequence be complementary solely to the coding portion of the coding strand of the DNA molecule. The antisense sequence may be complementary to regulatory sequences specified on the coding strand of a DNA molecule encoding a polypeptide, which regulatory sequences control expression of the coding sequences.

As used herein, the term "autologous" is meant to refer to any material derived from the same individual to which it is later to be re-introduced into the individual.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

A "cytokine signaling regulator" or "regulator of cytokine signaling" or "regulator of cytokine signal transduction" refers to a protein that is capable of negatively regulating a cytokine signaling transduction pathway in a cell. Regulators of cytokine signal transduction including but are not limited to, suppressors of cytokine signal transduction (SOCS1-SOCS7, cytokine-inducible SH2-domain-containing protein (CIS)), SH2-containing phosphates (SHP), and protein inhibitors of activated STATs (PIAS).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "epitope" as used herein is defined as a small chemical molecule on an antigen that can elicit an immune response, including B and/or T cell responses. An antigen can have one or more epitopes. Most antigens have many epitopes; i.e., they are multivalent. In general, an epitope is roughly five amino acids and/or sugars in size. One skilled in the art understands that generally the overall three-dimensional structure, rather than the specific linear sequence of the molecule, is the main criterion of antigenic specificity and therefore distinguishes one epitope from another.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, expression vectors may contain nucleic acid sequences that serve other functions as well.

As used herein, "fusion protein" means a non-naturally occurring protein product, wherein the domains of the fusion protein are derived from one or more other proteins or artificially derived sequences. For example, each domain can be derived from a different naturally occurring protein sequence, or mutant/variant thereof, that possesses the desired properties. In one embodiment of the present invention, two or more antigenic polypeptides are encoded by a single polynucleotide to produce a fusion protein capable of eliciting an immune response to multiple antigens.

The term "helper T cell" as used herein is defined as an effector T cell whose primary function is to promote the activation and functions of other B and T lymphocytes and or macrophages. Most helper T cells are CD4 T-cells.

The term "heterologous" as used herein is defined as DNA or RNA sequences or proteins that are derived from the different species.

"Homologous" as used herein, refers to the subunit sequence similarity between two polymeric molecules, e.g., two nucleic acid molecules or two polypeptide molecules. When a subunit position in both of the two molecules is occupied by the same monomeric subunit. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. Alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Lipman, *PNAS USA* 85:2444, 1988, by computerized implementations of the algorithms GAP, BESTFIT, FASTA, and TFASTA, or by manual alignment and visual inspection. Other algorithms for determining homology or identity include, for example, in addition to a BLAST program (Basic Local Alignment Search Tool at the National Center for Biotechnology Information). As used herein, "homology" is used synonymously with "identity."

As used herein, "immunogen" refers to a substance that is able to stimulate or induce a humoral antibody and/or cell-mediated immune response in a mammal.

The term "immunoglobulin" or "Ig", as used herein is defined as a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, "a negative immune regulator" or "a negative regulator" or "a negative regulator of the immune response" refers to a protein that is capable of negatively regulating an immune signaling transduction pathway in a cell. Typically, the negative immune regulator negatively regulates a proinflammatory signal transduction pathway. Negative immune regulators disclosed herein include, but are not limited to sTLR, RP105, SIGIRR, ST2, NOD2, MyD88s, IRAK (IRAKM, IRAK1, IRAK2), IRF-4, FLN29, TWEAK, TRIAD3A, CYLD, Cbl, A20, SUMO (SUMO1, SUMO2, SUMO3, and SUMO4), I-κB proteins, MKPs, Foxj1, Foxo3a, TWIST (Twist 1, Twist 2), Roquin, Dok (Dok-1, Dok-2), PI3K, prostaglandin, TRAIL-R, arrestin, TOLLIP, SOCS (SOCS1, SOCS2, SOCS3, SOCS4, SOCS5, SOCS6, SOCS7, and CIS), PIAS (PIAS1, PIAS3, PIASx and PIASy), SHP (SHP-1 and SHP-2), or combinations thereof. Negative immune regulators can belong to different protein families including, but not limited to an inhibitory homolog of a protein involved in signal transduction (e.g., soluble decoy TLRs, inhibitory TIR homologs, inhibitory signaling molecule isoforms, inhibitory cytokine homologs, and the like), a protein involved in molecular stability, an inhibitory component of a signaling molecule complex, a protein involved in the regulation of signaling molecule phosphorylation, a transcription factor that suppresses transcription of NF-κB targeted genes, a protein involved in the regulation of RNA translation and stability, a cytokine signaling regulator, and the like. In one aspect, inhibiting one or more negative immune regulators in an immune cell serves to enhance immunopotency of the cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

The term "major histocompatibility complex", or "MHC", as used herein is defined as a specific cluster of genes, many of which encode evolutionarily related cell surface proteins involved in antigen presentation, which are among the most important determinants of histocompatibility. Class I MHC, or MHC-I, function mainly in antigen presentation to CD8 T lymphocytes. Class II MHC, or MHC-II, function mainly in antigen presentation to CD4 T lymphocytes.

The term "polynucleotide" as used herein is defined as a chain of nucleotides. Furthermore, nucleic acids are polymers of nucleotides. Thus, nucleic acids and polynucleotides as used herein are interchangeable.

The term "polypeptide" as used herein is defined as a chain of amino acid residues, usually having a defined sequence. As used herein the term polypeptide is mutually inclusive of the terms "peptide" and "protein".

"Proliferation" is used herein to refer to the reproduction or multiplication of similar forms of entities, for example proliferation of a cell. That is, proliferation encompasses production of a greater number of cells, and can be measured by, among other things, simply counting the numbers of cells, measuring incorporation of $^3$H-thymidine into the cell, and the like.

The term "promoter" as used herein is defined as a DNA sequence recognized by the synthetic machinery of the cell, or introduced synthetic machinery, required to initiate the specific transcription of a polynucleotide sequence. A "constitutive" promoter is a nucleotide sequence which, when operably linked with a polynucleotide which encodes or specifies a gene product, causes the gene product to be produced in a cell under most or all physiological conditions of the cell. An "inducible" promoter is a nucleotide sequence which, when operably linked with a polynucleotide which encodes or specifies a gene product, causes the gene product to be produced in a cell substantially only when an inducer which corresponds to the promoter is present in the cell. A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

The term "self-antigen" as used herein is defined as an antigen that is expressed by a host cell or tissue. Self-antigens may be tumor antigens, but in certain embodiments, are expressed in both normal and tumor cells. A skilled artisan would readily understand that a self-antigen may be overexpressed in a cell.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cells that have been separated from the cells with which they are naturally associated in their natural state. In some embodiments, the cells are cultured in vitro. In other embodiments, the cells are not cultured in vitro.

As used herein, the term "substitution" is one of mutations that is generally used in the art. Substitution variants have at least one amino acid residue in a polypeptide molecule replaced by a different residue. "Conservative substitutions" typically provide similar biological activity as the unmodified polypeptide sequence from which the conservatively modified variant was derived. Conservative substitutions typically include the substitution of one amino acid for another with similar characteristics. Conservative substitution tables providing functionally similar amino acids are well known in the art. For example, the following six groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic (Cationic): Arginine (R), Lysine (K), Histidine (H); Acidic (Anionic): Aspartic acid (D), Glutamic acid (E); Amide: Asparagine (N), Glutamine (Q).

The term "T-cell" as used herein is defined as a thymus-derived cell that participates in a variety of cell-mediated immune reactions.

The term "B-cell" as used herein is defined as a cell derived from the bone marrow and/or spleen. B cells can develop into plasma cells which produce antibodies.

As used herein, a "therapeutically effective amount" is the amount of a therapeutic composition sufficient to provide a beneficial effect to a mammal to which the composition is administered.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

As used herein, the terms "treating" or "treatment" or "alleviation" refers to both therapeutic treatment and prophylactic or preventative measures, wherein the object is to prevent or slow down (lessen) the targeted pathologic condition or disorder. For example, for cancer, reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues.

The phrase "under transcriptional control" or "operatively linked" as used herein means that the promoter is in the correct location and orientation in relation to a polynucleotide to control the initiation of transcription by RNA polymerase and expression of the polynucleotide.

The term "vaccine" as used herein is defined as a material used to provoke an immune response after administration of the material to a mammal.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Vaccine and Adjuvant Compositions

In one aspect, the present invention provides vaccine compositions for the activation of DCs, in which the vaccine composition is an inhibitor of a negative immune regulator, a prominflammatory molecule, such as flaggellin, and optionally an antigen. In one embodiment, the components of the vaccine or adjuvant are produced by polynucleotide expression vectors. In one embodiment, the inhibitor of a negative immune regulator is a siRNA for SOCS1 or A20. This section of the detailed description will describe the general components of vaccine compositions and how those components may be assembled.

Negative Immune Regulators

General. Negative immune regulators can belong to different protein families including, but not limited to inhibitory homologs of a protein involved in signal transduction (e.g., soluble decoy TLRs, inhibitory TIR homologs, inhibitory signaling molecule isoforms, inhibitory cytokine homologs, and the like), a protein involved in molecular stability, an inhibitory component of a signaling molecule complex, a protein involved in the regulation of signaling molecule phosphorylation, a transcription factor that suppresses transcription of NF-κB targeted genes, a protein involved in the regulation of RNA translation and stability, a cytokine signaling regulator, and the like. Examples of negative immune regulators include, but are not limited to sTLR, RP105, SIGIRR, ST2, NOD2, MyD88s, IRAK (IRAKM, IRAK1, IRAK2), IRF-4, FLN29, TWEAK, TRIAD3A, CYLD, Cbl, A20, SUMO (SUMO1, SUMO2, SUMO3, and SUMO4), I-κB proteins, MKPs, Foxj1, Foxo3a, TWIST (Twist 1, Twist 2), Roquin, Dok (Dok-1, Dok-2), PI3K, prostaglandin, TRAIL-R, arrestin, TOLLIP, SOCS (SOCS1, SOCS2, SOCS3, SOCS4, SOCS5, SOCS6, SOCS7, and CIS), PIAS (PIAS1, PIAS3, PIASx and PIASy), SHP (SHP-1 and SHP-2), and the like.

A negative immune regulator in an immune cell serves to "silence" control points in the immune cell, thereby enhancing immunopotency in the cell. In one aspect, inhibition of an inhibitory homolog of a protein involved in signal transduction (e.g., soluble decoy TLRs, inhibitory TIR homologs, inhibitory signaling molecule isoforms, inhibitory cytokine homologs, and the like), a protein involved in molecular stability, an inhibitory component of a signaling molecule complex, a protein involved in the regulation of signaling molecule phosphorylation, a transcription factor that suppresses transcription of NF-κB targeted genes, a protein involved in the regulation of RNA translation and stability, a cytokine signaling regulator, or any combinations thereof provides a therapeutic benefit to a mammal when used in the vaccine compositions of the present invention.

The polynucleotide and polypeptide sequences for various negative immune regulators may be found at computerized databases known to those of ordinary skill in the art. One such database is the National Center for Biotechnology Information's Genbank and GenPept databases. The nucleic acid sequences for these known genes may be amplified, combined with the sequences disclosed herein (e.g., ligated) and/or expressed using the techniques disclosed herein or by any technique that would be know to those of ordinary skill in the art (e.g., Sambrook et al., 2001). Though a nucleic acid may be expressed in an in vitro expression system, in some embodiments the nucleic acid comprises a vector for in vivo replication and/or expression.

Regulators of Cytokine Signaling. In one aspect, the negative immune regulator is a regulator of cytokine signaling including, but not limited to, suppressors of cytokine signal transduction (SOCS), SH2-containing phosphates (SHP), and protein inhibitors of activated STATs (PIAS).

Inducible inhibitors of cytokine signaling are the suppressor of cytokine signaling (SOCS) proteins, of which there are eight family members: SOCS1-SOCS7 and the cytokine-inducible SH2-domain-containing protein (CIS). SOCS proteins recognize cytokine receptors or the associated JAKs and attenuate signal transduction both by direct interference with signaling and by targeting the receptor complex for ubiquitin-mediated proteasomal degradation. SHP proteins, including but not limited to (SHP-1 and SHP-2), are constitutively expressed and can attenuate cytokine signal transduction by dephosphorylating signaling intermediates such as Janus kinase (JAK) and its receptor. Members of the protein inhibitors of activated STATs (PIAS) family, including but not limited to PIAS1, PIAS3, PIASx and PIASy, are also constitutively expressed and attenuate signal transduction by repressing STAT activity. The process of sumoylation has been implicated in PIAS-mediated repression of STAT activity.

Inhibitory Homolog of a Protein Involved in Signal Transduction. An effective immune response is attributed to activation of DCs in response to a pathogenic infection. This activation includes signaling through pathogen-recognition receptors, such as TLRs. Members of the TLRs signal in a similar manner due to the presence of a conserved, cytosolic Toll/interleukin-1 receptor (TIR) domain, which activates common signaling pathways, particularly those leading to the activation of NF-κB and stress-activated protein kinases. NF-κB activation catalyzes immune responses by secreting proinflammatory cytokines such as TNF, IFN, interleukin 1 (IL-1), IL-6, and IL-12 and by expressing costimulatory molecules such as CD80, CD86, and CD40.

A frequently used strategy for regulating an immune response based on TLR signaling in a cell is to competitively inhibit key signaling molecules by their non-functional homolog or isoforms that do not have stimulatory activity at the extracellular portion of the TLR. Proteins in this family of negative immune regulators include, but are not limited to soluble decoy TLRs (sTLR). sTLR suppress the interaction of TLRs with pathogenic products (e.g., microbial products). For example, soluble decoy TLR2 competes with TLR2 for the interaction with corresponding microbial ligands. In another instance, soluble decoy TLR4 interacts with MD2 and inhibits the formation of the MD2-TLR4 complex, thereby blocking LPS-mediated signaling by TLR4.

Based on the present disclosure, one skilled in the art would appreciate that the invention includes compositions and methods for inhibiting a negative immune regulator, where the negative immune regulator is a non-functional homolog of a signaling molecule. Preferably, the non-functional homolog of a signaling molecule is a soluble decoy TLR Inhibiting a non-functional homolog of a signaling molecule (or otherwise inhibiting a sTLR) serves to inhibit the inhibitory effects of the non-functional homolog on the signaling molecule.

In addition to inhibiting soluble decoy TLRs, another strategy of enhancing TLR signaling is to inhibit proteins that contain a non-functional TIR homolog or isoforms at the cytoplasmic region of the TLR. These proteins are members of the family of proteins that share a membrane-bound non-functional TIR homolog that contains a TIR domain having no stimulatory activity (otherwise known as a non-functional receptor). Such proteins include, but are not limited, to SIGIRR (single immunoglobulin IL-1R-related molecule), ST2, and RP105.

Without wishing to be bound by any particular theory, these proteins suppress TLR signaling by inhibiting or sequestering a TLR from binding to its corresponding signaling molecule. For example, SIGIRR attenuates TLR4 signaling by competing with TLR4 to interact with signaling molecules. Thus, the invention includes compositions and methods of inhibiting a negative immune regulator, where the negative immune regulator is a membrane-bound non-functional TIR homolog, to enhance TLR signaling in an immune cell. This strategy provides support for the general concept of inhibiting a negative immune regulator to enhance the immunopotency of an immune cell.

TLR signaling can also be regulated by NOD2. NOD2 is a member of the nucleotide-binding oligomerization domain family that can recognize the bacterial product muramyl dipeptide (MDP). NOD2 is a negative regulator of TLR2 signaling. Based on the present disclosure presented herein, inhibiting NOD2 in an immune cell suppresses the inhibitory effect of NOD2 on TLR signaling in the cell. Accordingly, inhibiting NOD2 in an immune enhances immunopotency of the cell.

Another strategy of regulating TLR signaling is to regulate cytoplasmic signaling proteins, such as MyD88 and IRAK. Negative immune regulators that inhibit cytoplasmic signaling molecules are considered to be non-functional isoforms (or otherwise known as signaling molecule isoforms) of key signaling molecules in TLR signaling. An example of a negative immune regulator that is considered to be a non-functional isoform is an alternatively spliced short variant of MyD88 which lacks the intermediary domain. This splice variant of MyD88, which is denoted as MyD88s, has been found to suppress TLR signaling. For example, MyD88s inhibits LPS-induced NF-κB activation. It is believed that MyD88s inhibits LPS-induced NF-κB activation due to its inability to bind to IRAK4 and promote IRAK1 phosphorylation. Based on the disclosure presented herein, inhibiting a negative immune regulator, where the negative immune regulator is a non-functional isoform (e.g., MyD88s) in a cell provides a means to enhance TLR signaling in a cell and thereby enhancing immunopotency of the cell.

Another example of a protein belonging to the family of inhibitory homologs of a protein involved in signal transduction is IRAK. The IRAK family of kinases comprises four members: IRAK1, IRAK2, IRAK4 and IRAKM. Moreover, IRAKM lacks kinase activity and functions as a global negative immune regulator of TLR signaling in a cell. Therefore, inhibiting a negative immune regulator, where the negative immune regulator is a non-functional isoform such as IRAKM, provides support for the general concept of inhibiting a negative immune regulator in an immune cell to enhance immunopotency of the cell.

Other negative immune regulators of TLR signaling include, but are not limited to members of the IFN regulatory factor (IRF) family of transcription factors, FLN29 (a novel interferon- and LPS-inducible gene), and TWEAK. Accordingly, inhibiting any one or more of these negative immune regulators can prevent the inhibitory effects of each negative immune regulator on the immune response. Therefore, inhibiting any one or more of these negative immune regulators provides a means to enhance TLR signaling in a cell and thereby enhancing immunopotency of the cell.

Regulators of Molecular Stability. One family of negative immune regulators employs a strategy of regulating signaling molecule stability. This strategy is associated with regulating the stability of key signaling molecules by ubiquitanition/deubiquitanition, and to increase the stability of inhibitory components of signaling molecule complexes by sumoylation and other mechanisms. Many of these negative immune regulators, such as TRIAD3A, Cyld, Cbl, A20, and SUMO, are ubiquitin-modifying enzymes, which modify target TLRs and signaling molecules, and promote their degradation to attenuate TLR signal transduction. In some instances, these negative immune regulators can also attenuate TNFR signal transduction. Therefore, based on the disclosure presented herein, one skilled in the art would appreciate that inhibiting one of more of these negative immune regulators in an immune cell enhances TLR and/or TNFR signaling in the cell. A result of enhancing TLR and/or TNFR signaling in a cell is the increased immunopotency of the cell.

Other negative immune regulators involved in regulating molecular stability include the arrestin family. Based on the present disclosure, one skilled in the art would appreciate that inhibiting an arrestin family member in an immune cell suppresses the inhibitory effects of an arrestin family member on the activation of NF-κB Inhibiting an arrestin family member therefore enhances the immunopotency of the cell.

Inhibitory Components of Signaling Molecule Complexes. Negative immune regulators that are members of the family of inhibitory components of signaling molecule complexes include the I-κB proteins. I-κB proteins, which include I-κBα, I-κBβ and I-κBε, sequester NF-κB proteins in the cytoplasm and thereby inhibit NF-κB from its normal function. I-κB proteins retain NF-κB in the cytoplasm by masking nuclear-localization sequences (NLSs) on NF-κB subunits.

An important event in the activation of NF-κB is the phosphorylation of I-κBs by I-κB kinase (IKK) complex. The IKK complex is a converging point for the activation of NF-κB by various stimuli, including TLR ligands and TNF. The IKK complex contains two catalytic subunits, IKKα and IKKβ, and controls the activation of NF-κB transcription factors. IKKβ mediates NF-κB activation in response to pro-inflammatory cytokines and microbial products. A negative regulatory role for IKKα in controlling NF-κB activation has been observed. IKKα contributes to suppression of NF-κB activity by accelerating both the degradation of the NF-κB subunits RelA and c-Rel, and the removal of RelA and c-Rel from pro-inflammatory gene promoters.

Based on the disclosure presented herein, proteins that negatively regulate NF-κB or otherwise prevent activation of NF-κB are candidates for targeted inhibition using the methods disclosed herein to enhance immunopotency of a cell. One skilled in the art would appreciate that inhibiting I-κB proteins, IKKα, IKKβ or any combinations can suppress the inhibitory effects of these proteins on NF-κB activation.

Regulation of Signaling Molecule Phosphorylation. The MAPK signaling pathways are associated with activation of an immune response. MAPK pathways are subject to feedback inhibition by MAPK phosphatases (MKPs), because the phosphatases are induced after activation of the MAPK pathway. Based on the disclosure presented herein, inhibiting a MKP (e.g., MKP5 and MKP6) serves to suppress the inhibitory effects of the MKP on its corresponding MAPK pathway. MKP5 and MKP6 have been shown to negatively regulate T cell activation by inhibiting the activity of their respective MAPK targets.

Based on the disclosure presented herein, one skilled in the art would appreciate that inhibiting a MKP (e.g., MKP5 and MKP6) can suppress the inhibitory effects of the phosphatase on the MAPK signaling pathway Inhibiting a MKP in an immune cell can enhance the immunopotency of the cell.

Regulators of Target Gene Transcription. Another strategy to regulate an immune response is to suppress the transcription of NF-κB targeted genes or to enhance the transcription of negative components in signaling molecule complexes. Such a strategy encompasses inhibiting negative immune regulators including, but not limited to Twist-1, Twist-2, Foxj1, and Foxo3a. The disclosure presented herein demonstrates that inhibiting the levels of at least one of these proteins can enhance immunopotency of the cell.

Foxo3a and Foxj1 are members of the forkhead transcription factor family, which are actively involved in the negative regulation of NF-κB. Twist is another negative immune regulator of NF-κB. Twist binds to E boxes in cytokine promoters and inhibits the activity of NF-κB bound to neighboring-κB sites.

Methods of Inhibiting a Negative Immune Regulator:

The present invention includes inhibiting a negative immune regulator in a cell to enhance immunopotency of the cell. Preferably, the invention includes inhibiting one or more negative immune regulator selected from the group consisting of A20, SUMO (SUMO1, SUMO2, SUMO3, and SUMO4), Foxj1, Foxo3a, TWIST (Twist 1, Twist 2), SOCS (SOCS1, SOCS2, SOCS3, SOCS4, SOCS5, SOCS6, SOCS7, and CIS), PIAS (PIAS1, PIAS3, PIASx and PIASy), SHP (SHP-1 and SHP-2), and the like.

In one embodiment, the composition comprising an inhibitor of the negative immune regulator is selected from the group consisting of a small interfering RNA (siRNA), a microRNA, an antisense nucleic acid, a ribozyme, an expression vector encoding a transdominant negative mutant, an intracellular antibody, a peptide and a small molecule.

One skilled in the art will appreciate, based on the disclosure provided herein, that one way to decrease the mRNA and/or protein levels of a negative immune regulator, such as a cytokine signaling regulator in a cell is by reducing or inhibiting expression of the nucleic acid encoding the regulator. Thus, the protein level of the negative immune regulator in a cell can also be decreased using a molecule or compound that inhibits or reduces gene expression such as, for example, an antisense molecule or a ribozyme.

Antisense Nucleic Acids. In one embodiment, the modulating sequence is an antisense nucleic acid sequence which is expressed by a vector. The antisense expressing vector is used to transfect a mammalian cell or the mammal itself, thereby causing reduced endogenous expression of the desired negative immune regulator. Antisense molecules and their use for inhibiting gene expression are well known in the art (see, e.g., Cohen, 1989, In: *Oligodeoxyribonucleotides, Antisense Inhibitors of Gene Expression*, CRC Press). Antisense nucleic acids are DNA or RNA molecules that are complementary to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, *Anal. Biochem.* 172:289). Such antisense molecules may be provided to the cell via genetic expression using DNA encoding the antisense molecule as taught by U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Ribozymes. Ribozymes and their use for inhibiting gene expression are also well known in the art (see, e.g., Cech et al., 1992, *J. Biol. Chem.* 267:17479-17482; Hampel et al., 1989, *Biochemistry* 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, *J. Amer. Med. Assn.* 260:3030). A major advantage of this approach is the fact that ribozymes are sequence-specific.

There are two basic types of ribozymes, namely, tetrahymena-type (Hasselhoff, 1988, *Nature* 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful for inhibiting the expression of a negative immune regulator may be designed by incorporating target sequences into the basic ribozyme structure which are complementary to the mRNA sequence of the desired negative immune regulator. Ribozymes targeting the desired negative immune regulator may be synthesized using commercially available reagents (Applied Biosystems, Inc., Foster City, Calif.) or they may be genetically expressed from DNA encoding them.

Small Interfering RNA (siRNA). A "small interfering RNA" or "short interfering RNA" or "siRNA" or "short hairpin RNA" or "shRNA" is a RNA duplex of nucleotides that is targeted to a nucleic acid sequence of interest. As used herein, the term "siRNA" encompasses all forms of siRNA including, but not limited to (i) a double stranded RNA polynucleotide, (ii) a single stranded polynucleotide, and (iii) a polynucleotide of either (i) or (ii) wherein such a polynucleotide, has one, two, three, four or more nucleotide alterations or substitutions therein.

A siRNA in the form of a double stranded polynucleotide comprises about 18 base pairs, about 19 base pairs, about 20 base pairs, about 21 base pairs, about 22 base pairs, about 23 base pairs, about 24 base pairs, about 25 base pairs, about 26 base pairs, about 27 base pairs, about 28 base pairs, about 29 base pairs or about 30 base pairs in length. The double stranded siRNA capable of interfering with the expression and/or the activity of a negative immune regulator.

A single stranded siRNA comprises a portion of an RNA polynucleotide sequence that is targeted to a gene or polynucleotide of interest. A single stranded siRNA comprises a polynucleotide of about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides or about 30 nucleotides in length. The single stranded siRNA is capable of interfering with expression and/or activity of a target polynucleotide such as A20, SUMO (SUMO1, SUMO2, SUMO3, and SUMO4), Foxj1, Foxo3a, TWIST (Twist 1, Twist 2), SOCS (SOCS1, SOCS2, SOCS3, SOCS4, SOCS5, SOCS6, SOCS7, and CIS), PIAS (PIAS1, PIAS3, PIASx and PIASy), SHP (SHP-1 and SHP-2), and the like. The single strand siRNA is also capable of annealing to a complementary sequence to result in a dsRNA that is capable of interfering with the expression and/or the activity of a negative immunoregulator.

In yet another aspect, the siRNA comprises a polynucleotide comprising either a double stranded or a single stranded polynucleotide, wherein the siRNA has one, two, three, four or more nucleotide alterations or substitutions therein.

A siRNA polynucleotide is an RNA nucleic acid molecule that interferes with RNA activity that is generally considered to occur via a post-transcriptional gene silencing mechanism. A siRNA polynucleotide preferably comprises a double-stranded RNA (dsRNA) but is not intended to be so limited and may comprise a single-stranded RNA (see, e.g., Martinez et al., 2002 *Cell* 110:563-74). The siRNA polynucleotide may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynucleotide or the like, typically in 5' to 3' phosphodiester linkage). Accordingly, it will be appreciated that certain exemplary sequences disclosed herein as DNA sequences capable of directing the transcription of the siRNA polynucleotides are also intended to describe the corresponding RNA sequences and their complements, given the well established principles of complementary nucleotide base-pairing.

A siRNA may be transcribed using DNA as a template (genomic DNA, cDNA, or synthetic DNA) that contains a promoter for an RNA polymerase promoter. For example, the promoter can be the U6 promoter or the H1 RNA polymerase III promoter.

Alternatively, the siRNA may be a synthetically derived RNA molecule. In certain embodiments, the siRNA polynucleotide may have blunt ends. In certain other embodiments, at least one strand of the siRNA polynucleotide has at least one, and preferably two nucleotides that "overhang" (i.e., that do not base pair with a complementary base in the opposing strand) at the 3' end of either strand of the siRNA polynucleotide. In a preferred embodiment of the invention, each strand of the siRNA polynucleotide duplex has a two-nucleotide overhang at the 3' end. The two-nucleotide overhang is preferably a thymidine dinucleotide (TT) but may also comprise other bases, for example, a TC dinucleotide or a TG dinucleotide, or any other dinucleotide. The overhang dinucleotide may also be complementary to the two nucleotides at the 5' end of the sequence of the polynucleotide that is targeted for interference. For a discussion of 3' ends of siRNA polynucleotides see, e.g., WO 01/75164.

Preferred siRNA polynucleotides comprise double-stranded polynucleotides of about 18-30 nucleotide base pairs, preferably about 18, about 19, about 20, about 21, about 22, about 23, about 24, about 25, about 26, or about 27 base pairs, and in other preferred embodiments about 19, about 20, about 21, about 22 or about 23 base pairs, or about 27 base pairs, whereby the use of "about" indicates that in certain embodiments and under certain conditions the processive cleavage steps that may give rise to functional siRNA polynucleotides that are capable of interfering with expression of a selected polypeptide may not be absolutely efficient. Hence, siRNA polynucleotides, may include one or more siRNA polynucleotide molecules that may differ (e.g., by nucleotide insertion or deletion) in length by one, two, three, four or more base pairs as a consequence of the variability in processing, in biosynthesis, or in artificial synthesis of the siRNA. The siRNA polynucleotide of the present invention may also comprise a polynucleotide sequence that exhibits variability by differing (e.g., by nucleotide substitution, including transition or transversion) at one, two, three or four nucleotides from a particular sequence. These differences can occur at any of the nucleotide positions of a particular siRNA polynucleotide sequence, depending on the length of the molecule, whether situated in a sense or in an antisense strand of the double-stranded polynucleotide. The nucleotide difference may be found on one strand of a double-stranded polynucleotide, where the complementary nucleotide with which the substitute nucleotide would typically form hydrogen bond base pairing, may not necessarily be correspondingly substituted. In preferred embodiments, the siRNA polynucleotides are homogeneous with respect to a specific nucleotide sequence.

Polynucleotides that comprise the siRNA polynucleotides of the present invention may in certain embodiments be derived from a single-stranded polynucleotide that comprises a single-stranded oligonucleotide fragment (e.g., of about 18-30 nucleotides) and its reverse complement, typically separated by a spacer sequence. According to certain such embodiments, cleavage of the spacer provides the single-stranded oligonucleotide fragment and its reverse complement, such that they may anneal to form, optionally with additional processing steps that may result in addition or removal of one, two, three or more nucleotides from the 3' end and/or the 5' end of either or both strands, the double-stranded siRNA polynucleotide of the present invention. In certain embodiments, the spacer is of a length that permits the fragment and its reverse complement to anneal and form a double-stranded structure (e.g., like a hairpin polynucleotide) prior to cleavage of the spacer, and optionally, subsequent processing steps that may result in addition or removal of one, two, three, four, or more nucleotides from the 3' end and/or the 5' end of either or both strands. A spacer sequence may therefore be any polynucleotide sequence as provided herein that is situated between two complementary polynucleotide sequence regions which, when annealed into a double-stranded nucleic acid, result in a siRNA polynucleotide. Preferably, the spacer sequence comprises at least 4 nucleotides. In certain embodiments, the spacer may comprise 5, 6, 7, 8, 9, 10, 11, 12, 13, 14, 15, 16, 17, 18, 19, 20, 21-25, 26-30, 31-40, 41-50, 51-70, 71-90, 91-110, 111-150, 151-200 or more nucleotides. Examples of siRNA polynucleotides derived from a single nucleotide strand comprising two complementary nucleotide sequences separated by a spacer have been described (e.g., Brummelkamp et al., 2002 *Science* 296:550; Paddison et al., 2002 *Genes Develop.* 16:948; Paul et al., 2002 *Nat. Biotechnol.* 20:505-508; Grabarek et al., 2003 *BioTechniques* 34:734-44).

Polynucleotide variants may contain one or more substitutions, additions, deletions, and/or insertions such that the activity of the siRNA polynucleotide is not substantially diminished. The effect of any such alterations in nucleotide content on the activity of the siRNA polynucleotide may generally be assessed as described elsewhere herein. Variants preferably exhibit at least about 75%, 78%, 80%, 85%, 87%, 88% or 89% identity and more preferably at least about 90%, 92%, 95%, 96%, or 97% identity to a portion of a polynucleotide sequence that encodes a native A20, SUMO (SUMO1, SUMO2, SUMO3, and SUMO4), Foxj1, Foxo3a, TWIST (Twist 1, Twist 2), SOCS (SOCS1, SOCS2, SOCS3, SOCS4, SOCS5, SOCS6, SOCS7, and CIS), PIAS (PIAS1, PIAS3, PIASx and PIASy), SHP (SHP-1 and SHP-2), and the like. The percent identity may be readily determined by comparing sequences of the polynucleotides to the corresponding portion of the target polynucleotide, using any method including using computer algorithms well known to those having ordinary skill in the art. These include the Align or the BLAST algorithm (Altschul, 1991 *J. Mol. Biol.* 219:555-565; Henikoff and Henikoff, 1992, *PNAS* 89:10915-10919).

Certain siRNA polynucleotide variants can be substantially homologous to a portion of a polynucleotide encoding a target polypeptide. Single-stranded polynucleotides derived from these polynucleotide variants are capable of hybridizing under moderately stringent conditions to a naturally occurring DNA or RNA sequence encoding the target polypeptide. A siRNA polynucleotide that detectably hybridizes to the polynucleotide sequence encoding the target polypeptide under moderately stringent conditions may have a nucleotide sequence that includes at least 10 consecutive nucleotides, more preferably 11, 12, 13, 14, 15, 16, 17, 18, 19, 20, 21, 22, 23, 24, 25, 26, 27, 28, 29 or 30 consecutive nucleotides that are complementary to a particular target polynucleotide. In certain preferred embodiments, such a siRNA sequence (or its complement) will be unique to a single particular polynucleotide encoding the target polypeptide for which interference with expression is desired. In certain other embodiments, the sequence (or its complement) may be shared by two or more related polynucleotides encoding the target polypeptide for which interference with polypeptide expression is desired.

Suitable moderate stringent conditions include, for example, pre-washing the polynucleotide in a solution of 5×SSC, 0.5% SDS, 1.0 mM EDTA (pH 8.0); hybridizing the polynucleotide at 50° C. to 70° C., 5×SSC for 1 to 16 h (i.e., overnight); followed by washing the polynucleotide once or twice at 22° C. to 65° C. for 20 to 40 min with one or more each of 2×, 0.5× and 0.2×SSC containing 0.05% to 0.1% SDS. For additional stringency, hybridization conditions may include an additional wash in 0.1×SSC and 0.1% SDS at 50° C. to 60° C. for 15 to 40 min. Those of ordinary skill in the art will understand that, variations in stringency of hybridization conditions may be achieved by altering the time, temperature, and/or concentration of the solutions used for the pre-hybridization, hybridization, and wash steps. Suitable conditions may also depend in part on the particular nucleotide sequences of the probe used, and of the blotted, proband nucleic acid sample. Accordingly, it will be appreciated that suitably stringent conditions can be readily selected, without undue experimentation, when a desired selectivity of the polynucleotide is identified, based on its ability to hybridize to one or more certain proband sequences while not hybridizing to certain other proband sequences.

Sequence specific siRNA polynucleotides of the present invention may be designed using one or more of several criteria. For example, to design a siRNA polynucleotide that has about 21 consecutive nucleotides identical to a sequence encoding a polypeptide of interest, the open reading frame of the polynucleotide sequence may be scanned for about 21-base sequences length that have one or more of the following characteristics: (1) an A+T/G+C ratio of approximately 1:1 but no greater than 2:1 or 1:2; (2) an AA dinucleotide or a CA dinucleotide at the 5' end; (3) an internal hairpin loop melting temperature less than 55° C.; (4) a homodimer melting temperature of less than 37° C. (melting temperature calculations as described in (3) and (4) can be determined using computer software known to those skilled in the art); (5) a sequence of at least 16 consecutive nucleotides not identified as being present in any other known polynucleotide sequence. Alternatively, a siRNA polynucleotide sequence may be designed and chosen using a computer software available commercially from various vendors, e.g., OligoEngine™ (Seattle, Wash.); Dharmacon, Inc. (Lafayette, Colo.); Ambion Inc. (Austin, Tex.); and QIAGEN, Inc. (Valencia, Calif.)). See also Elbashir et al., 2000 *Genes & Development* 15:188-200; Elbashir et al., 2001 *Nature* 411:494-98. The siRNA polynucleotide may then be tested for the ability to interfere with the expression of the target polypeptide according to methods known in the art and described elsewhere in herein. The determination of the effectiveness of a siRNA polynucleotide includes not only consideration of its ability to interfere with the expression of the target polypeptide, but also whether the siRNA polynucleotide is toxic to the host cell. For example, a desirable siRNA would exhibit an RNA interference activity and would also not exhibit an unwanted biological consequence. An example of an unwanted biological consequence is apoptosis of a cell for which cell death is not a desired as a result of the introduction of the siRNA into the host cell.

Based on the present disclosure, it should be appreciated that the siRNAs may effect silencing of the target polypeptide expression to different degrees. The siRNAs thus must first be tested for their effectiveness. Selection of siRNAs are made therefrom based on the ability of a given siRNA to interfere with or modulate the expression of the target polypeptide. Accordingly, identification of specific siRNA polynucleotide sequences that are capable of interfering with expression of a desired target polypeptide requires production and testing of each siRNA. The methods for testing each siRNA and selection of suitable siRNAs for use in the present invention are described further in the Examples. Since not all siRNAs that interfere with protein expression will have a physiologically important effect, the present disclosure also sets forth various physiologically relevant assays for determining whether the levels of interference with target protein expression using the siRNAs of the invention have clinically relevant significance.

One skilled in the art will readily appreciate that as a result of the degeneracy of the genetic code, many different nucleotide sequences may encode the same polypeptide. That is, an amino acid may be encoded by one of several different codons, and a person skilled in the art can readily determine that while one particular nucleotide sequence may differ from another, the polynucleotides may in fact encode polypeptides with identical amino acid sequences. As such, polynucleotides that vary due to differences in codon usage are specifically contemplated by the present invention.

A number of specific siRNA polynucleotide sequences useful for interfering with target polypeptide expression are presented herein. siRNA polynucleotides may generally be prepared by any method known in the art, including, for example, solid phase chemical synthesis. Modifications in a polynucleotide sequence may also be introduced using standard mutagenesis techniques, such as oligonucleotide-directed site-specific mutagenesis. Further, siRNAs may be chemically modified or conjugated with other molecules to improve their stability and/or delivery properties. Included as one aspect of the invention are siRNAs as described herein, wherein one or more ribose sugars has been removed therefrom.

Alternatively, siRNA polynucleotide molecules may be generated by in vitro or in vivo transcription of suitable DNA sequences (e.g., polynucleotide sequences encoding a target polypeptide, or a desired portion thereof), provided that the DNA is incorporated into a vector with a suitable RNA polymerase promoter (such as for example, T7, U6, H1, or SP6 although other promoters may be equally useful). In addition, a siRNA polynucleotide may be administered to a mammal, as may be a DNA sequence (e.g., a recombinant nucleic acid construct as provided herein) that supports transcription (and optionally appropriate processing steps) such that a desired siRNA is generated in vivo.

In one embodiment, a siRNA polynucleotide, wherein the siRNA polynucleotide is capable of interfering with expression of a target polypeptide can be used to generate a silenced cell. Any siRNA polynucleotide that, when expressed in or contacted with a cell, results in a significant decrease in the expression of the target polypeptide is included in the invention. Preferably the decrease is greater than about 10%, more preferably greater than about 20%, more preferably greater than about 30%, more preferably greater than about 40%, about 50%, about 60%, about 70%, about 75%, about 80%, about 85%, about 90%, about 95% or about 98% relative to the expression level of the target polypeptide detected in the absence of the siRNA. Preferably, the presence of the siRNA polynucleotide in a cell does not result in or cause any undesired toxic effects, for example, apoptosis or death of a cell in which apoptosis is not a desired effect of RNA interference.

In another embodiment, the siRNA polynucleotide that, when expressed in or contacted with a cell, results in a significant decrease in the expression of the target polypeptide. Preferably the decrease is about 10% to 20%, more preferably about 20% to 30%, more preferably about 30% to 40%, more preferably about 40% to 50%, more preferably about 50% to 60%, more preferably about 60% to 70%, more preferably about 70% to 80%, more preferably about 80% to 90%, more preferably about 90% to 95%, more preferably about 95% to 98% relative to the expression level of the target polypeptide detected in the absence of the siRNA. Preferably, the presence of the siRNA polynucleotide in a cell does not result in or cause any undesired toxic effects.

In yet another embodiment, the siRNA polynucleotide that, when expressed in or contacted with a cell, results in a significant decrease in the expression of the target polypeptide. Preferably the decrease is about 10% or more, more preferably about 20% or more, more preferably about 30% or more, more preferably about 40% or more, more preferably about 50% or more, more preferably about 60% or more, more preferably about 70% or more, more preferably about 80% or more, more preferably about 90% or more, more preferably about 95% or more, more preferably about 98% or more relative to the expression level of the target polypeptide detected in the absence of the siRNA. Preferably, the presence of the siRNA polynucleotide in a cell does not result in or cause any undesired toxic effects.

As such, the invention comprises a siRNA polynucleotide, such as siRNAs as exemplified in SEQ ID NOS:5-160 in Table 6. SEQ ID NOs:5-7 are sequences of huma siRNA candidates for SOCS1. SEQ ID NOs:8-13, 14-19, 20-25, 26-31, and 32-37 are sequences of huma siRNA candidate sequences for PIAS1, PIAS3, PIASx, PIASy and SHP-1. Examples of targeted sequences for A20, SUMO1, SUMO2, SUMO3, SUMO4, Twist-1, Twist-2, Foxj1, and Foxo3a are exemplified in SEQ ID NOs:38-59, 60-67, 68-80, 81-87, 88-103, 104-111, 112-124, 125-136, and 137-160, respectively.

TABLE 5

| Name | SEQ ID NO | Sequence (5' to 3') |
|---|---|---|
| human SOCS1-siRNA1 | SEQ ID NO: 5 | CACGCACTTCCGCACATTC |
| human SOCS1-siRNA2 | SEQ ID NO: 6 | TTCCGTTCGCACGCCGATT |
| human SOCS1-siRNA3 | SEQ ID NO: 7 | GAGCTTCGACTGCCTCTTC |
| human PIAS1-siRNA1 | SEQ ID NO: 8 | CCACCAGTCCTCAAATAAA |
| human PIAS1-siRNA2 | SEQ ID NO: 9 | TGATTGACCTAACCATAGA |
| human PIAS1-siRNA3 | SEQ ID NO: 10 | GACACAAGCTACATTAATA |
| human PIAS1-siRNA4 | SEQ ID NO: 11 | TGACGCAACTCTTTACATT |
| human PIAS1-siRNA5 | SEQ ID NO: 12 | CCAGCCGACCAATTAATAT |
| human PIAS1-siRNA6 | SEQ ID NO: 13 | TTACGACTTACAAGGATTA |
| human PIAS3-siRNA1 | SEQ ID NO: 14 | AGAAGGTCGAAGTTATTGA |
| human PIAS3-siRNA2 | SEQ ID NO: 15 | ATTACTCCTTGTCTGTGTA |
| human PIAS3-siRNA3 | SEQ ID NO: 16 | AGATTGTGATGAGATCCAA |
| human PIAS3-siRNA4 | SEQ ID NO: 17 | TTTGAGGAAGCGCACTTTA |
| human PIAS3-siRNA5 | SEQ ID NO: 18 | AGCCGACATCCAAGGTTTA |
| human PIAS3-siRNA6 | SEQ ID NO: 19 | CGACATCCAAGGTTTAGAT |
| human PIASx-siRNA1 | SEQ ID NO: 20 | CCAGAGCACTAATTAAAGA |
| human PIASx-siRNA2 | SEQ ID NO: 21 | CCATGTTATTACAGAGATT |
| human PIASx-siRNA3 | SEQ ID NO: 22 | GCTATTCCGCCTTCATTAA |
| human PIASx-siRNA4 | SEQ ID NO: 23 | TATTCCGCCTTCATTAACA |
| human PIASx-siRNA5 | SEQ ID NO: 24 | CCACCATACGCCAATATCA |
| human PIASx-siRNA6 | SEQ ID NO: 25 | GCGCTGCATTTATTGAAGA |
| human PIASy-siRNA1 | SEQ ID NO: 26 | AGAATCTGTTACTCAGACA |
| human PIASy-siRNA2 | SEQ ID NO: 27 | TCACTCACCTCATGTACCT |
| human PIASy-siRNA3 | SEQ ID NO: 28 | TCTGTCCGCTGGTGAAGAT |
| human PIASy-siRNA4 | SEQ ID NO: 29 | TCGCATTGACGCCAAGACA |

TABLE 5-continued

| Name | SEQ ID NO | Sequence (5' to 3') |
|---|---|---|
| human PIASy-siRNA5 | SEQ ID NO: 30 | GCTCTACGGAAGTACTTA |
| human PIASy-siRNA6 | SEQ ID NO: 31 | CTACGGAAAGTACTTAAAC |
| human SHP-1-siRNA1 | SEQ ID NO: 32 | CAAACAGCATCCAGATAGA |
| human SHP-1-siRNA2 | SEQ ID NO: 33 | TGATGTTCCAGACAATAAT |
| human SHP-1-siRNA3 | SEQ ID NO: 34 | TAAATGCGCCTGTGACTTA |
| human SHP-1-siRNA4 | SEQ ID NO: 35 | TCACAACACCTCAAACATA |
| human SHP-1-siRNA5 | SEQ ID NO: 36 | TCAGAAGTATTACGCAGAA |
| human SHP-1-siRNA6 | SEQ ID NO: 37 | GACAACCGGTCGAAAGAAA |
| human A20-siRNA1 | SEQ ID NO: 38 | AGACACACGCAACTTTAAA |
| human A20-siRNA2 | SEQ ID NO: 39 | CAGACACACGCAACTTTAA |
| human A20-siRNA3 | SEQ ID NO: 40 | ACACACGCAACTTTAAATT |
| human A20-siRNA4 | SEQ ID NO: 41 | ACGAATGCTTTCAGTTCAA |
| human A20-siRNA5 | SEQ ID NO: 42 | ATACTCGGAACTGGAATGA |
| human A20-siRNA6 | SEQ ID NO: 43 | GAAGCTTGTGGCGCTGAAA |
| human A20-siRNA7 | SEQ ID NO: 44 | AAAGCCGGCTGCGTGTATTTT |
| human A20-siRNA8 | SEQ ID NO: 45 | AAAGGGAGCTCTAGTCCTTTT |
| human A20-siRNA9 | SEQ ID NO: 46 | AAGGGAGCTCTAGTCCTTTTT |
| human A20-siRNA10 | SEQ ID NO: 47 | AAGCCCTCATCGACAGAAACA |
| human A20-siRNA11 | SEQ ID NO: 48 | AAACGAACGGTGACGGCAATT |
| human A20-siRNA12 | SEQ ID NO: 49 | AAACAGACACGCAACTTTA |
| human A20-siRNA13 | SEQ ID NO: 50 | AACAGACACGCAACTTTAA |
| human A20-siRNA14 | SEQ ID NO: 51 | AATGTGCAGCACAACGGATTT |
| human A20-siRNA15 | SEQ ID NO: 52 | AAAAGCCGGCTGCGTGTATTT |
| human A20-siRNA16 | SEQ ID NO: 53 | AAACTCAACCAGCTGCCTTTT |
| human A20-siRNA17 | SEQ ID NO: 54 | AAACTCAACCAGCTGCCTTIT |

TABLE 5-continued siRNA Sequences

| Name | SEQ ID NO | Sequence (5' to 3') |
|---|---|---|
| human A20-siRNA18 | SEQ ID NO: 55 | AAGTCCTTCCTCAGGCTTTGT |
| human A20-siRNA19 | SEQ ID NO: 56 | AAAGCCAGAAGAAACTCAACT |
| human A20-siRNA20 | SEQ ID NO: 57 | AATCCGAGCTGTTCCACTTGT |
| human A20-siRNA21 | SEQ ID NO: 58 | AAGGCTGGGACCATGGCACAA |
| human A20-siRNA22 | SEQ ID NO: 59 | AATGCCGCAAAGTTGGATGAA |
| human SUMO1-siRNA1 | SEQ ID NO: 60 | AAGGCCACAATACCTTTTAA |
| human SUMO1-siRNA2 | SEQ ID NO: 61 | AAAACCTTCAACTGAGGACTT |
| human SUMO1-siRNA3 | SEQ ID NO: 62 | AAAGACAGGGTGTTCCAATGA |
| human SUMO1-siRNA4 | SEQ ID NO: 63 | AAGACAGGGTGTTCCAATGAA |
| human SUMO1-siRNA5 | SEQ ID NO: 64 | AATGGAGGAAGAAGATGTGAT |
| human SUMO1-siRNA6 | SEQ ID NO: 65 | AAGATGGCTTCACTGAAGAAA |
| human SUMO1-siRNA7 | SEQ ID NO: 66 | AACTCCAAAGATGGCTTCACT |
| human SUMO1-siRNA8 | SEQ ID NO: 67 | AAGTGCCTTCTGAATCAAGGA |
| human SUMO2-siRNA1 | SEQ ID NO: 68 | AAAAGGGAACCTGCTTCTTTA |
| human SUMO2-siRNA2 | SEQ ID NO: 69 | AAAGCCCAAGGAAGGAGTCAA |
| human SUMO2-siRNA3 | SEQ ID NO: 70 | AAGGAGTCAAGACTGAGAACA |
| human SUMO2-siRNA4 | SEQ ID NO: 71 | AAGAGGCATACACCACTTAGT |
| human SUMO2-siRNA5 | SEQ ID NO: 72 | AACGACAGGGATTGTCAATGA |
| human SUMO2-siRNA6 | SEQ ID NO: 73 | AAGGGAACCTGCTTCTTTACT |
| human SUMO2-siRNA7 | SEQ ID NO: 74 | AAGACTGAGAACAACGATCAT |
| human SUMO2-siRNA8 | SEQ ID NO: 75 | AACAGACACCTGCACAGTT |
| human SUMO2-siRNA9 | SEQ ID NO: 76 | AATCCTTGCATACCTTGTTCA |
| human SUMO2-siRNA10 | SEQ ID NO: 77 | AAGTCAAGCGTCTTGTTGTTT |
| human SUMO2-siRNA11 | SEQ ID NO: 78 | AACAGCAGACGGGAGGTGTCT |
| human SUMO2-siRNA12 | SEQ ID NO: 79 | AACCTGCTTCTTTACTCCAGA |
| human SUMO2-siRNA13 | SEQ ID NO: 80 | AACTGCAATTTGGTTCCACCA |
| human SUMO3-siRNA1 | SEQ ID NO: 81 | ACACCATCGACGTGTTCCA |
| human SUMO3-siRNA2 | SEQ ID NO: 82 | AAGGATTGGCACAACCAAAAT |
| human SUMO3-siRNA3 | SEQ ID NO: 83 | AATTGGGCCAATCAGAATTGT |
| human SUMO3-siRNA4 | SEQ ID NO: 84 | AACCGAGTCTTTTGGTAATTT |
| human SUMO3-siRNA5 | SEQ ID NO: 85 | AATGGTGTTGTGGCCTCAGAT |
| human SUMO3-siRNA6 | SEQ ID NO: 86 | AAGGTGTCTGCGGAAACTCGA |
| human SUMO3-siRNA7 | SEQ ID NO: 87 | AAGGGAAAATACTGGAATGCT |
| human SUMO4-siRNA1 | SEQ ID NO: 88 | AAGCAGATCAGATTCCGATTT |
| human SUMO4-siRNA2 | SEQ ID NO: 89 | AAAAGGGAACCTGCTTCTTTA |
| human SUMO4-siRNA3 | SEQ ID NO: 90 | AAAGCCCACAGAAGAAGTCAA |
| human SUMO4-siRNA4 | SEQ ID NO: 91 | AAGAGGCAGACACCACTTAGT |
| human SUMO4-siRNA5 | SEQ ID NO: 92 | AAGGGAACCTGCTTCTTTACT |
| human SUMO4-siRNA6 | SEQ ID NO: 93 | AAGTGGAGACAGGATGGGAAA |
| human SUMO4-siRNA7 | SEQ ID NO: 94 | AACGAAAAGCCCACAGAAGAA |
| human SUMO4-siRNA8 | SEQ ID NO: 95 | AAGAAGTCAAGACTGAGAACA |
| human SUMO4-siRNA9 | SEQ ID NO: 96 | AAGTCAAGACTGAGAACAACA |
| human SUMO4-siRNA10 | SEQ ID NO: 97 | AACAGACAAACCTGCACAGTT |
| human SUMO4-siRNA11 | SEQ ID NO: 98 | AAACCAAACAGCCAATGGTAT |
| human SUMO4-siRNA12 | SEQ ID NO: 99 | AAGGTGGCGGGACAGGATGGT |
| human SUMO4-siRNA13 | SEQ ID NO: 100 | AACAGCCTACGGGAGGTGTCT |
| human SUMO4-siRNA14 | SEQ ID NO: 101 | AACCTGCTTCTTTACTCCAGA |
| human SUMO4-siRNA15 | SEQ ID NO: 102 | AACGCTGTTCTTTAAAGACCA |
| human SUMO4-siRNA16 | SEQ ID NO: 103 | AACTGCAATTTGGTTCCACCA |
| human TWIST1-siRNA1 | SEQ ID NO: 104 | ACTCCAAGATGGCAAGCTG |

TABLE 5-continued siRNA Sequences

| Name | SEQ ID NO | Sequence (5' to 3') |
|---|---|---|
| human TWIST1-siRNA2 | SEQ ID NO: 105 | TGGCAAGCTGCAGCTATGT |
| human TWIST1-siRNA3 | SEQ ID NO: 106 | AAGGAGAAAATGGACAGTCTA |
| human TWIST1-siRNA4 | SEQ ID NO: 107 | AAAGGCATCACTATGGACTTT |
| human TWIST1-siRNA5 | SEQ ID NO: 108 | AAGATGGCAAGCTGCAGCTAT |
| human TWIST1-siRNA6 | SEQ ID NO: 109 | AAACTGGCCTGCAAAACCATA |
| human TWIST1-siRNA7 | SEQ ID NO: 110 | AAGCTGCAGCTATGTGGCTCA |
| human TWIST1-siRNA8 | SEQ ID NO: 111 | AAAGCGAGACAGGCCCGTGGA |
| human TWIST2-siRNA1 | SEQ ID NO: 112 | GACGAGATGGACAATAAGA |
| human TWIST2-siRNA2 | SEQ ID NO: 113 | TGAGCAAGATCCAGACGCT |
| human TWIST2-siRNA3 | SEQ ID NO: 114 | AGCGACGAGATGGACAATA |
| human TWIST2-siRNA4 | SEQ ID NO: 115 | ACGAGATGGACAATAAGAT |
| human TWIST2-siRNA5 | SEQ ID NO: 116 | GAGCGACGAGATGGACAAT |
| human TWIST2-siRNA6 | SEQ ID NO: 117 | CGAGATGGACAATAAGATG |
| human TWIST2-siRNA7 | SEQ ID NO: 118 | CAGCAAGAAGTCGAGCGAA |
| human TWIST2-siRNA8 | SEQ ID NO: 119 | AAGTCGAGCGAAGATGGCA |
| human TWIST2-siRNA9 | SEQ ID NO: 120 | AGCAAGAAGTCGAGCGAAG |
| human TWIST2-siRNA10 | SEQ ID NO: 121 | AAGAAGTCGAGCGAAGATG |
| human TWIST2-siRNA11 | SEQ ID NO: 122 | AAGGGCACTCCCAGCCCTCTT |
| human TWIST2-siRNA12 | SEQ ID NO: 123 | AAGCTGGCCGCCAGGTACATA |
| human TWIST2-siRNA13 | SEQ ID NO: 124 | AACTGGACCAAGGCTCTCAGA |
| human FOXJ1-siRNA1 | SEQ ID NO: 125 | AGCCTGGACTTCGATGAGA |
| human FOXJ1-siRNA2 | SEQ ID NO: 126 | ACTCGTATGCCACGCTCAT |
| human FOXJ1-siRNA3 | SEQ ID NO: 127 | TCGTATGCCACGCTCATCT |
| human FOXJ1-siRNA4 | SEQ ID NO: 128 | TCTACAAGTGGATCACGGA |
| human FOXJ1-siRNA5 | SEQ ID NO: 129 | TGGATCACGGACAACTTCT |
| human FOXJ1-siRNA6 | SEQ ID NO: 130 | GGATCACGGACAACTTCTG |
| human FOXJ1-siRNA7 | SEQ ID NO: 131 | TACTCGTATGCCACGCTCA |
| human FOXJ1-siRNA8 | SEQ ID NO: 132 | AACGAGGGCCCAGGACCAGAA |
| human FOXJ1-siRNA9 | SEQ ID NO: 133 | AACCGGCTAAAGGACCCTGCA |
| human FOXJ1-siRNA10 | SEQ ID NO: 134 | AAGCCCGACTTGAGGCTGAGA |
| human FOXJ1-siRNA11 | SEQ ID NO: 135 | AATCCGCCACAACCTGTCTCT |
| human FOXJ1-siRNA12 | SEQ ID NO: 136 | AACTGGGAGGGATGCCGAGCT |
| human FOX3A-siRNA1 | SEQ ID NO: 137 | TCACTGCATAGTCGATTCA |
| human FOX3A-siRNA2 | SEQ ID NO: 138 | AGCTCTTGGTGGATCATCA |
| human FOX3A-siRNA3 | SEQ ID NO: 139 | GCTCTTGGTGGATCATCAA |
| human FOX3A-siRNA4 | SEQ ID NO: 140 | GGACAATAGCAACAAGTAT |
| human FOX3A-siRNA5 | SEQ ID NO: 141 | ATAGCAACAAGTATACCAA |
| human FOX3A-siRNA6 | SEQ ID NO: 142 | CGAATCAGCTGACGACAGT |
| human FOX3A-siRNA7 | SEQ ID NO: 143 | ACGTGATGCTTCGCAATGA |
| human FOX3A-siRNA8 | SEQ ID NO: 144 | AGAACTTGCTCCACCACCA |
| human FOX3A-siRNA9 | SEQ ID NO: 145 | AGCCGTGCCTTGTCGAATT |
| human FOX3A-siRNA10 | SEQ ID NO: 146 | GTCAGCCAGTCTATGCAAA |
| human FOX3A-siRNA11 | SEQ ID NO: 147 | AACCCAGCAGAGACTGTTAAT |
| human FOX3A-siRNA12 | SEQ ID NO: 148 | AATGTGACATGGAGTCCATTA |
| human FOX3A-siRNA13 | SEQ ID NO: 149 | AAGCACAGAGTTGGATGAAGT |
| human FOX3A-siRNA14 | SEQ ID NO: 150 | AACTGCCACGGCTGACTGATA |
| human FOX3A-siRNA15 | SEQ ID NO: 151 | AACGTGATGCTTCGCAATGAT |
| human FOX3A-siRNA16 | SEQ ID NO: 152 | AACCAGGGAAGTTTGGTCAAT |
| human FOX3A-siRNA17 | SEQ ID NO: 153 | AAGTGGACAGTGATACCGTTT |
| human FOX3A-siRNA18 | SEQ ID NO: 154 | AATCCCACGCCATTTTCCTAA |

TABLE 5-continued siRNA Sequences

| Name | SEQ ID NO | Sequence (5' to 3') |
|---|---|---|
| human FOX3A-siRNA19 | SEQ ID NO: 155 | AACGGCTCACTCTGTCCCAGA |
| human FOX3A-siRNA20 | SEQ ID NO: 156 | AAGGGCGACAGCAACAGCTCT |
| human FOX3A-siRNA21 | SEQ ID NO: 157 | AACCAACTCTCCTTCTCTCTT |
| human FOX3A-siRNA22 | SEQ ID NO: 158 | AACTCTCCTTCTCTCTTCTTT |
| human FOX3A-siRNA23 | SEQ ID NO: 159 | AAGTCTACGGGTGCCAGATCA |
| human FOX3A-siRNA24 | SEQ ID NO: 160 | AAGTGGAGCTGGACCCGGAGT |

Following the generation of the siRNA polynucleotide of the present invention, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987 *Tetrahedron Lett.* 28:3539-3542; Stec et al., 1985 *Tetrahedron Lett.* 26:2191-2194; Moody et al., 1989 *Nucleic Acids Res.* 12:4769-4782; Eckstein, 1989 *Trends Biol. Sci.* 14:97-100; Stein, In: *Oligodeoxynucleotides. Antisense Inhibitors of Gene Expression*, Cohen, ed., Macmillan Press, London, pp. 97-117 (1989)).

Any polynucleotide of the invention may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl- methyl-, thio- and other modified forms of adenine, cytidine, guanine, thymine, and uridine.

Antigens Useful in the Compositions of the Present Invention

The present invention includes various methods for pulsing APCs including, but not limited to, loading APCs with whole antigen in the form of a protein, cDNA or mRNA. However, the invention should not be construed to be limited to the specific form of the antigen used for pulsing the APC. Rather, the invention encompasses other methods known in the art for generating an antigen loaded APC. The APC may be transfected with mRNA encoding a defined antigen. mRNA corresponding to a gene product whose sequence is known can be rapidly generated in vitro using appropriate primers and reverse transcriptase-polymerase chain reaction (RT-PCR) coupled with transcription reactions. Transfection of an APC with an mRNA provides an advantage over other antigen-loading techniques for generating a pulsed APC. For example, the ability to amplify RNA from a microscopic amount of tissue, i.e., tumor tissue, extends the use of the APC for vaccination to a large number of patients.

The antigen may be derived from a virus, a fungus, or a bacterium. The antigen may be a self-antigen or an antigen associated with a disease selected from the group consisting of an infectious disease, a cancer, an autoimmune disease. Furthermore, multiple antigens may be provided simultaneously, either separately or as a fusion protein.

For an antigenic composition to be useful as a vaccine, the antigenic composition must induce an immune response to the antigen in a cell, tissue or mammal (e.g., a human). In particular embodiments the antigenic composition comprises or encodes all or part of any antigen described herein, or an immunologically functional equivalent thereof. In certain embodiments, the antigenic composition is conjugated to or comprises an HLA anchor motif amino acids.

In one embodiment, the antigenic composition may be a fusion protein of two or more antigens. The fusion protein may be encoded by an expression vector, which is introduced into cells, or may be contacted with cells directly. When the fusion protein is encoded by an expression vector, the polynucleotide segments encoding each antigen are operably linked so that translation of the mRNA produces the fusion protein. Optionally, with a sequence encoding a spacer separates the two segments. In a specific embodiment, the antigenic composition comprises a dominant negative survivin mutant and a MUC1 fragment joined together in a fusion protein.

It is understood that an antigenic composition of the present invention may be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding a peptide or polypeptide comprising an antigen of the present invention in an in vitro translation system or in a living cell. In addition, an antigenic composition can comprise a cellular component isolated from a biological sample. Preferably the antigenic composition isolated and extensively dialyzed to remove one or more undesired small molecular weight molecules and/or lyophilized for more ready formulation into a desired vehicle. It is further understood that additional amino acids, mutations, chemical modification and such like, if any, that are made in a vaccine component will preferably not substantially interfere with the antibody recognition of the epitopic sequence.

A peptide or polypeptide corresponding to one or more antigenic determinants of the present invention should generally be at least five or six amino acid residues in length, and may contain up to about 10, about 15, about 20, about 25, about 30, about 35, about 40, about 45 or about 50 residues or so. A peptide sequence may be synthesized by methods known to those of ordinary skill in the art, such as, for example, peptide synthesis using automated peptide synthesis machines, such as those available from Applied Biosystems, Inc., Foster City, Calif. (Foster City, Calif.).

Longer peptides or polypeptides also may be prepared, e.g., by recombinant means. In certain embodiments, a nucleic acid encoding an antigenic composition and/or a component described herein may be used, for example, to produce an antigenic composition in vitro or in vivo for the various compositions and methods of the present invention. For example, in certain embodiments, a nucleic acid encoding an antigen is comprised in, for example, a vector in a recombinant cell. The nucleic acid may be expressed to produce a peptide or polypeptide comprising an antigenic sequence. The peptide or polypeptide may be secreted from the cell, or comprised as part of or within the cell.

In certain embodiments, an immune response may be promoted by transfecting or inoculating a mammal with a nucleic acid encoding an antigen. One or more cells comprised within a target mammal then expresses the sequences encoded by the nucleic acid after administration of the nucleic acid to the mammal. A vaccine may also be in the form, for example, of a nucleic acid (e.g., a cDNA or an RNA) encoding all or part of the peptide or polypeptide sequence of an antigen. Expression in vivo by the nucleic acid may be, for example, by a plasmid type vector, a viral vector, or a viral/plasmid construct vector.

In preferred aspects, the nucleic acid comprises a coding region that encodes all or part of the sequences encoding an appropriate antigen, or an immunologically functional equivalent thereof. Of course, the nucleic acid may comprise and/or encode additional sequences, including but not limited to those comprising one or more immunomodulators or adjuvants.

Tumor-Associated Antigens. In the context of the present invention, "tumor antigen" or "hyperporoliferative disorder antigen" or "antigen associated with a hyperproliferative disorder" refer to antigens that are common to specific hyperproliferative disorders. In certain aspects, the tumor-associated antigens of the present invention are derived from, cancers including but not limited to primary or metastatic melanoma, thymoma, lymphoma, sarcoma, lung cancer, gastric cancer, liver cancer, non-Hodgkin's lymphoma, Hodgkin's lymphoma, leukemia, uterine cancer, cervical cancer, bladder cancer, kidney cancer and adenocarcinomas such as breast cancer, prostate cancer, ovarian cancer, pancreatic cancer, and the like.

In one embodiment, the tumor antigen of the present invention comprises one or more antigenic cancer epitopes immunologically recognized by tumor infiltrating lymphocytes (TIL) derived from a cancer tumor of a mammal. Increasing numbers of TAAs have been identified for tumor vaccination. An ideal TAA should be highly expressed in tumor cells, but not normal cells, and should be obligatory for the survival of tumor cells. Survivin, a member of the inhibitory apoptotic protein (IAP) gene family, has been found to be highly expressed in the majority of human cancers, including tumors of the lung, colon, pancreas, prostate, breast, stomach and others, but largely undetectable in most normal tissues. In an analysis of human transcriptomes of human normal and cancer tissues, survivin was identified as the fourth highest differential expression gene in common human cancer tissues compared to normal tissues. Moreover, MHC-restricted epitopes in survivin were identified and several clinical trials demonstrated the immunogenicity of survivin to induce anti-tumor immune responses in mice and cancer patients.

It is also generally believed that targeting multiple TAAs would be more effective than targeting one TAA for tumor vaccines. In one embodiment, MUC1 may be selected as the second immunogen for a DC vaccine, for use in combination with survivin. MUC1 is a highly glycosylated, transmembrane protein with an extracellular tandem repeat domain (TRD) normally expressed on the apical surface of ductal epithelia. The TRD is comprised of a variable number (20-100) of repeats of a 20 amino acid sequence. MUC1 is broadly overexpressed in various epithelial malignancies including lung, prostate, gastric, and colorectal carcinomas in abnormal, hypoglycosylated forms, which expose T cell epitopes. MUC1 is expressed on the surface of tumor cells, which can be recognized by antibodies for antibody-mediated tumor destruction. Thus, a vaccine composition of the present invention targeting the two TAAs survivin and MUC1 could be broadly used for the treatment of various types of human cancer including, but not limited to, lung, prostate, gastric, pancreatic, breast, and colorectal cancers.

Other embodiments of the present invention may use other TAAs. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD 19, CD20, idiotype) have been used as targets for passive immunotherapy with monoclonal antibodies with limited success.

The tumor antigen and the antigenic cancer epitopes thereof may be purified and isolated from natural sources such as from primary clinical isolates, cell lines and the like. The cancer peptides and their antigenic epitopes may also be obtained by chemical synthesis or by recombinant DNA techniques known in the arts.

Microbial Antigens. Microbial antigens may be viral, bacterial, or fungal in origin. Examples of infectious virus include: Retroviridae (e.g., human immunodeficiency viruses, such as HIV-1 (also referred to as HTLV-III, LAV or -HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviruses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia, Mycobacteria* sps (e.g., *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacte-*

*rium nucleatum, Streptobacillus moniliformis, Treponema Treponema pertenue, Leptospira,* and *Actinomyces israelii.*

Examples of infectious fungi include: *Cryptococcus neoformans, Histoplasma capsulatum, Coccidioides immitis, Blastomyces dermatitidis, Chlamydia trachomatis, Candida albicans.* Other infectious organisms (i.e., protists) including: *Plasmodium falciparum* and *Toxoplasma gondii.*

Proinflammatory Molecules of the Present Invention

The vaccine compositions of the present invention further comprise polynucleotides encoding a proinflammatory molecule. Proinflammatory molecules such as a Toll-like receptor (TLR) agonist or a cytokine stimulate proinflammatory signal transduction cascades. In one embodiment, polynucleotides encoding TLR ligands or proinflammatory cytokines are provided. While not wishing to be limited by theory, DCs use pattern-recognition receptors (PRR) such as TLRs to recognize conserved microbial structures such as lipopolysaccharide (LPS), flagellin, unmethylated bacterial DNA (CpG), and RNA. TLR signaling promotes DC maturation by activating NF-κB and MAP kinases, which then mediates the up-regulation of hundreds of proinflammatory genes, including MHC molecules and costimulatory molecules, and a large number of proinflammatory cytokines, resulting in the induction of innate and adaptive immunity Mature DCs then migrate to draining lymph nodes, where the cells establish contact with T-cells by forming an immunological synapse for T cell activation.

There are a variety of immune stimuli such as proinflammatory cytokines, chemokines, and TLR agonists available for the combinational use with an inhibitor of a negative immune regulator. In one embodiment, the proinflammatory molecule is a TLR agonist, such as flagellin. Flagellin, which is a TLR5 ligand, is the structural protein subunit of the bacterial flagellum and has potent immunomodulatory effects by causing activation of NF-κB. In addition, because TLR5 signaling requires its surface interaction with flagellin, the flagellin gene may be operably linked to a signal leader sequence for the secretion and subsequent binding to surface TLR5 on DCs in an auto- and para-crine manner in order to maximize its stimulatory activity. In other embodiments, cytokines may be used. Cytokines are involved in the regulation of activation, proliferation, and differentiation of immune cells.

Preparation of Vaccine Compositions of the Present Invention

In some aspects, the invention provides for the expression of nucleic acids, including an inhibitor of a negative immune regulator, one or more antigens, and a proinflammatory molecule. In each case, these may be provided as isolated nucleic acids operably linked to a nucleic acid comprising a promoter/regulatory sequence such that the nucleic acid is capable of directing expression of the protein or RNA molecule encoded by the nucleic acid. Thus, the invention encompasses expression vectors and methods for the introduction of exogenous DNA into cells with concomitant expression of the exogenous DNA in the cells such as those described, for example, in Sambrook et al. (2001, *Molecular Cloning: A Laboratory Manual*, Cold Spring Harbor Laboratory, New York), and in Ausubel et al. (1997, *Current Protocols in Molecular Biology*, John Wiley & Sons, New York).

In one embodiment, the invention includes a vector comprising a siRNA polynucleotide. Preferably, the siRNA polynucleotide is capable of inhibiting the expression of a target polypeptide, wherein the target polypeptide is selected from the group consisting of A20, SUMO (SUMO1, SUMO2, SUMO3, and SUMO4), Foxj1, Foxo3a, TWIST (Twist 1, Twist 2), SOCS (SOCS1, SOCS2, SOCS3, SOCS4, SOCS5, SOCS6, SOCS7, and CIS), PIAS (PIAS1, PIAS3, PIASx and PIASy), SHP (SHP-1 and SHP-2), or any combinations thereof. The incorporation of a desired polynucleotide into a vector and the choice of vectors is well-known in the art as described in, for example, Sambrook et al., supra, and Ausubel et al., supra.

The polynucleotides of the present invention can be cloned into a number of types of vectors. However, the present invention should not be construed to be limited to any particular vector. Instead, the present invention should be construed to encompass a wide plethora of vectors which are readily available and/or well-known in the art. For example, a polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

For expression of the polynucleotides of the invention, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2001). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In order to assess the expression of the polynucleotides of the invention, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 *FEBS Lett.* 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Uses of the Vaccine and Adjuvant Compositions

Generation of a Silenced and Activated Immune Cell

In one embodiment, the present invention provides a cell-based system for expressing an inhibitor of a negative immune regulator into a cell, a proinflammatory molecule, and optionally, an antigen. The cell-based system comprises a cell and a one or more expression vectors for expressing the inhibitor, the proinflammatory molecule, and the antigen. A cell comprising an inhibitor is said to be "silenced" and possesses a heightened immunopotency as compared to an otherwise identical cell not so silenced with the inhibitor.

This invention includes a cell comprising an inhibitor of a negative immune regulator. In one aspect, the inhibitor is capable of inhibiting at least one of the following: A20, SUMO (SUMO1, SUMO2, SUMO3, and SUMO4), Foxj1, Foxo3a, TWIST (Twist 1, Twist 2), SOCS (SOCS1, SOCS2, SOCS3, SOCS4, SOCS5, SOCS6, SOCS7, and CIS), PIAS (PIAS1, PIAS3, PIASx and PIASy), SHP (SHP-1 and SHP-2), and the like. In one aspect, the cell can be transfected with a vector comprising a polynucleotide encoding an inhibitor. The polynucleotide need not be integrated into the cell. In another aspect, the cell need not be transfected with a vector at all, but rather, the cell is exposed to an inhibitor that is not expressed from a vector. An example of such an inhibitor is a chemically synthesized siRNA.

The invention further includes a cell that has been exposed or otherwise "pulsed" with an antigen and activated by the antigen. For example, an APC may become Ag-loaded in vitro, e.g., by culture ex vivo in the presence of an antigen, or in vivo by exposure to an antigen.

A skilled artisan would also readily understand that an APC can be "pulsed" in a manner that exposes the APC to an antigen for a time sufficient to promote presentation of that antigen on the surface of the APC. For example, an APC can be exposed to an antigen in a form small peptide fragments, known as antigenic peptides, are "pulsed" directly onto the outside of the APCs (Mehta-Damani et al., 1994); or APCs can be incubated with whole proteins or protein particles which are then ingested by the APCs. These whole proteins are digested into small peptide fragments by the APC and eventually carried to and presented on the APC surface (Cohen et al., 1994). Antigen in peptide form may be exposed to the cell by standard "pulsing" techniques described herein.

In a further embodiment of the invention, the APC may be transfected with a vector which allows for the expression of a specific protein by the APC. The protein which is expressed by the APC may then be processed and presented on the cell surface on an MHC receptor. The transfected APC may then be used as an immunogenic composition to produce an immune response to the protein encoded by the vector.

Without wishing to be bound by any particular theory, the antigen in the form of a foreign or an autoantigen is processed by the APC of the invention in order to retain the immunogenic form of the antigen. The immunogenic form of the antigen implies processing of the antigen through fragmentation to produce a form of the antigen that can be recognized by and stimulate immune cells, for example T cells. Preferably, such a foreign or an autoantigen is a protein which is processed into a peptide by the APC. The relevant peptide which is produced by the APC may be extracted and purified for use as an immunogenic composition. Peptides processed by the APC may also be used to induce tolerance to the proteins processed by the APC.

It is believed that autoimmune diseases result from an immune response being directed against "self-proteins," otherwise known as autoantigens, i.e., autoantigens that are present or endogenous in an individual. In an autoimmune response, these "self-proteins" are presented to T cells which cause the T cells to become "self-reactive." According to the method of the invention, APCs are pulsed with an antigen to produce the relevant "self-peptide." The relevant self-peptide is different for each individual because MHC products are highly polymorphic and each individual MHC molecule might bind different peptide fragments. The "self-peptide" and an agonist of inhibitors of cytokine signaling can then be used to design competing peptides or to induce tolerance to the self protein in the individual in need of treatment.

The antigen-activated APC, otherwise known as a "pulsed APC" of the invention, is produced by exposure of the APC to an antigen either in vitro or in vivo. In the case where the APC is pulsed in vitro, the APC is plated on a culture dish and exposed to an antigen in a sufficient amount and for a sufficient period of time to allow the antigen to bind to the APC. The amount and time necessary to achieve binding of the antigen to the APC may be determined by using methods known in the art or otherwise disclosed herein. Other methods known to those of skill in the art, for example immunoassays or binding assays, may be used to detect the presence of antigen on the APC following exposure to the antigen.

In the context of an expression vector, the vector can be readily introduced into a host cell, e.g., mammalian, bacterial, yeast or insect cell by any method in the art. For example, the expression vector can be transferred into a host cell by physical, chemical or biological means. It is readily understood that the introduction of the expression vector comprising the polynucleotide of the invention yields a silenced cell with respect to a negative immune regulator.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, *Molecular Cloning: A Laboratory Manual*, Cold Spring Harbor Laboratory, New York), and in Ausubel et al. (1997, *Current Protocols in Molecular Biology*, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To generate a silenced and activated cell, any DNA vector or delivery vehicle can be utilized to transfer the desired polynucleotide to an immune cell in vitro or in vivo. In the case where a non-viral delivery system is utilized, a preferred delivery vehicle is a liposome. The above-mentioned delivery systems and protocols therefore can be found in *Gene Targeting Protocols*, 2ed., pp 1-35 (2002) and *Gene Transfer and Expression Protocols*, Vol. 7, Murray ed., pp 81-89 (1991).

The use of lipid formulations is contemplated for the introduction of the polynucleotides encoding the inhibitor of the negative immune regulatory, the proinflammatory molecule, and/or the antigen into host cells (in vitro, ex vivo or in vivo). In a specific embodiment of the invention, the polynucleotide may be associated with a lipid. The polynucleotide associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid, lipid/polynucleotide or lipid/expression vector associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes.

Phospholipids may be used for preparing the liposomes according to the present invention and may carry a net positive, negative, or neutral charge. Diacetyl phosphate can be employed to confer a negative charge on the liposomes, and stearylamine can be used to confer a positive charge on the liposomes. The liposomes can be made of one or more phospholipids.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Lipids suitable for use according to the present invention can be obtained from commercial sources. For example, dimyristyl phosphatidylcholine ("DMPC") may be obtained from Sigma (St. Louis, Mo.), dicetyl phosphate ("DCP") may be obtained from K & K Laboratories (Plainview, N.Y.); cholesterol ("Chol") may be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

Cellular Vaccines

In one embodiment, a cell may be isolated from a culture, tissue, organ or organism, transfected, and administered to a mammal as a cellular vaccine. Thus, the present invention contemplates a "cellular vaccine." Of course, the cell may also express one or more additional vaccine components, such as immunomodulators or adjuvants. The vaccine may comprise all or part of the cell. In a suitable embodiment, the cellular vaccine of the present invention comprises a human APC and in a more preferred embodiment, the APC is a DC.

The cellular vaccine can comprise an APC that has been silenced according to the present invention to enhance its immunopotency. Immunopotency may be further enhanced by transfecting the cell with a polynucleotide encoding a proinflammatory molecule (e.g., a TLR agonist). The silenced APC can then be transfected with a nucleic acid encoding an antigen to generate an antigen-loaded cell. Based on the present disclosure, the silenced APC can be pulsed by any method using any type of antigen to load the antigen. In addition, an APC can be pulsed by any method prior to, concurrently with or following silencing of the APC.

As disclosed elsewhere herein, a cell can be pulsed with an antigen using various methods. An antigen of the present invention contains at least one epitope, wherein said epitope is capable of eliciting an immune response in a mammal. In one embodiment, the antigen is expressed by an expression vector. In another embodiment, the antigen is an isolated polypeptide. Preferably, the antigen is associated with a disease selected from the group consisting of an infectious disease, a cancer and an autoimmune disease. A number of preferred antigens useful for pulsing the cells of the invention are disclosed elsewhere herein. The antigen can be in the form of at least one or more of the following: a tumor lysate, a protein, a peptide, an mRNA, a DNA, expressed from a vector, a liposome and the like.

The APC that has been silenced with an inhibitor of a negative immune regulator possesses a heightened immunopotency and therefore elicits an enhanced immune response, i.e., an enhanced ability to present antigen and activate an immune response thereto. An APC that has been silenced and pulsed according to the present invention is able to stimulate effector T cells and elicit an improved immune response to the antigen thereto compared to an otherwise identical APC that has not been silenced.

Therapeutic Compositions and Methods

The present invention includes a composition useful for enhancing immunopotency of an immune cell such as an APC. The response to an antigen presented by an APC maybe measured by monitoring the induction of a cytolytic T-cell response, a helper T-cell response, and/or antibody response to the antigen using methods well known in the art.

The present invention includes a method of enhancing the immune response in a mammal comprising the steps of contacting one or more cells with an antigenic composition. Based on the present disclosure, a cell can be silenced by exposure to an inhibitor of a negative immune regulator and activated by the expression of a polynucleotide encoding a proinflammatory molecule, whereby the exposure to the inhibitor and proinflammatory molecule enhances the immunopotency of the cell. The cell can be silenced using methods disclosed herein prior to, concurrently with or following exposure of the cell with an antigenic composition to otherwise pulse the cell.

The enhanced immune response may be an active or a passive immune response. The response may be part of an adoptive immunotherapy approach in which APCs, such as dendritic cells, B cells or moncytes/macrophages, are obtained from a mammal (e.g., a patient), then pulsed with a composition comprising an antigenic composition (prior to, concurrently with or following the exposure of the cell to an inhibitor of a negative immune regulator to otherwise silence the immune cell), and then administering the APC to a mammal in need thereof.

The composition includes any combination of at least one or more of the following: an inhibitor of a negative immune regulator, a proinflammatory molecule, an antigen, a silenced immune cell, a pulsed cell, and a silenced immune cell that is also pulsed with an antigen. The composition may be a vaccine for ex vivo immunization and/or in vivo therapy in a mammal. Preferably, the mammal is a human.

With respect to ex vivo immunization, at least one of the following occurs in vitro prior to administering the cell into a mammal: i) silencing of the cell, ii) pulsing of the cell, iii) activation of the cell by a proinflammatory molecule, and/or iv) silencing, pulsing, and activation of the cell. It should be appreciated that an immune cell (i.e., APC) of the present invention can be silenced using the methods disclosed elsewhere herein prior to, concurrently with or following treatment of the APC with an antigen to pulse the immune cell.

Ex vivo procedures are well known in the art and are discussed more fully below. Briefly, cells are isolated from a mammal (preferably a human) and silenced (i.e., transduced or transfected in vitro) with an inhibitor of a negative immune regulator or with any other form of the negative immune regulator disclosed herein (i.e., chemically synthesized siRNA). The silenced cell may be further activated using a proinflammatory molecule (e.g., a TLR agonist, such as flagellin). The silenced cell may be further pulsed with an antigenic composition. The silenced and pulsed cell can be administered to a mammalian recipient to provide a therapeutic benefit. The mammalian recipient may be a human and the cell so silenced can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942 can be applied to the cells of the present invention. Other suitable methods are known in the art, therefore the present invention is not limited to any particular method of ex vivo expansion of the cells. Briefly, ex vivo culture and expansion of DCs comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

A variety of cell selection techniques are known for identifying and separating CD34+ hematopoietic stem or progenitor cells from a population of cells. For example, monoclonal antibodies (or other specific cell binding proteins) can be used to bind to a marker protein or surface antigen protein found on stem or progenitor cells. Several such markers or cell surface antigens for hematopoietic stem cells (i.e., flt-3, CD34, My-10, and Thy-1) are known in the art.

The collected CD34+ cells are cultured with suitable cytokines. CD34+ cells then are allowed to differentiate and commit to cells of the dendritic lineage. These cells are then further purified by flow cytometry or similar means, using markers characteristic of dendritic cells, such as CD1a, HLA DR, CD80 and/or CD86. Following isolation of culturing of DCs, the cells can be modified according to the methods of the present invention. Alternatively, the progenitor cells can be modified prior to being differentiated to DC-like cells.

In addition to using a cell-based vaccine in terms of ex vivo immunization, the present invention also provides compositions and methods for in vivo immunization to elicit an immune response directed against an antigen in a patient.

With respect to in vivo immunization, the present invention provides a use of an inhibitor of a negative immune regulator as a generic means to enhance vaccine potency by disabling a critical control point in an APC. As such, a vaccine useful for in vivo immunization comprises at least an inhibitor component, wherein the inhibitor component is able to inhibit a negative immune regulator. In another aspect, the vaccine comprises an inhibitor component, a proinflammatory component, and an antigen component, wherein the antigen component is capable of eliciting an immune response in a mammal.

Regarding in vivo immunization, a cell obtained from a patient is transfected or transduced in vivo to otherwise generate a silenced cell. The cell is silenced in vivo with a vector expressing an inhibitor of cytokine regulator. Alternatively, the cell is silenced using any other form of an inhibitor of negative immune regulator disclosed herein that is not expressed by a vector (i.e., chemically synthesized siRNA). Methods of generating a silenced cell in vivo are discussed herein.

Another aspect of the vaccine includes an antigen component useful for pulsing a cell in vivo. Any antigen can be administered in combination with the inhibitor of a negative immune regulator of the invention. A cell can be pulsed using any method as discussed elsewhere herein prior to, concurrently with or following silencing of the cell with a vaccine comprising an inhibitor. It is readily appreciated that in the event that a cell is to be pulsed and silenced concurrently, the mammal can be immunized with a single vaccine comprising both an inhibitor and a antigen. Alternatively, the mammal can be immunized with two separate vaccines, one comprising an inhibitor and a second vaccine comprising an antigen.

The invention encompasses in vivo immunization for cancer and infectious diseases. In one embodiment, the disorder or disease can be treated by in vivo administration of an inhibitor of a negative immune regulatory and a proinflammatory molecule in combination with an antigen to generate an immune response against the antigen in the patient. Based on the present disclosure, administration of an inhibitor of a negative immune regulator (e.g., siRNA for A20, SUMO (SUMO1, SUMO2, SUMO3, and SUMO4), Foxj1, Foxo3a, TWIST (Twist 1, Twist 2), SOCS (SOCS1, SOCS2, SOCS3, SOCS4, SOCS5, SOCS6, SOCS7, and CIS), PIAS (PIAS1, PIAS3, PIASx and PIASy), SHP (SHP-1 and SHP-2), or any combinations thereof) in combination with an antigenic formulation enhances the potency of an otherwise identical vaccination protocol without the use of an inhibitor of a negative immune regulator. Without wishing to be bound by any particular theory, it is believed that immune response to the antigen in the patient depends upon (1) the inhibitor of a negative immune regulator and/or proinflammatory molecule administered, (2) the duration, dose and frequency of administration, (3) the general condition of the patient, and if appropriate (4) the antigenic composition administered.

In one embodiment, the mammal has a type of cancer which expresses a tumor-specific antigen. In accordance with the present invention, an immunostimulatory protein can be made which comprises a tumor-specific antigen sequence component. In such cases, the inhibitor of negative immune regulator is administered in combination with an proinflammatory molecule (e.g., a TLR agonist) to a patient in need thereof, resulting in an improved therapeutic outcome for the patient, evidenced by, e.g., a slowing or diminution of the growth of cancer cells or a solid tumor which expresses the tumor-specific antigen, or a reduction in the total number of cancer cells or total tumor burden.

In a related embodiment, the patient has been diagnosed as having a viral, bacterial, fungal or other type of infection, which is associated with the expression of a particular antigen, e.g., a viral antigen. In accordance with the present invention, a protein may be made which comprises a sequence component consisting of the antigen, e.g., an HIV-specific antigen. In such cases, an inhibitor of a negative immune regulator and a proinflammatory molecule is administered in combination with the protein antigen to the patient in need thereof, resulting in an improved therapeutic outcome for the patient as evidenced by a slowing in the growth of the causative infectious agent within the patient and/or a decrease in, or elimination of, detectable symptoms typically associated with the particular infectious disease.

In either situation, the disorder or disease can be treated by administration of an inhibitor of a negative immune regulator in combination with an antigen to a patient in need thereof. The present invention provides a means to generate a protective DC-induced immune response to the antigen in the patient.

Dosage and Formulation of Pharmaceutical Compositions

The present invention envisions treating a disease, for example, HCV infection, cancer and the like, in a mammal by the administration of the vaccine and adjuvant compositions of the present invention. Administration of the vaccines in accordance with the present invention may be continuous or intermittent, depending, for example, upon the recipient's physiological condition, whether the purpose of the administration is therapeutic or prophylactic, and other factors known to skilled practitioners. The administration of the vaccines may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

The vaccine compositions of the present invention may comprise nucleic acids. Pharmaceutical formulations, dosages and routes of administration for nucleic acids are generally disclosed, for example, in Feigner et al., 1987, PNAS 84: 7413-7417. In one embodiment, nucleic acids are administered directly to a patient, e.g., to the site of the tumor or using a combination of one or more targeting agents to target the nucleic acid to an immune cell. In another embodiment, nucleic acids are contacted with immune cells isolated from the subject, and the transfected cells are introduced into the patient.

When the vaccine of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" substance is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes. The pharmaceutical formulations of the therapeutic agents of the invention can also take the form of an aqueous or anhydrous solution or dispersion, or alternatively the form of an emulsion or suspension.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Nucleic Acid Administration to Immune Cells. One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome, aggregated protein or transporter molecule.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the gene(s) inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

Experimental Animal Models

The methods and compositions of the invention have beneficial effects on eliciting an immune response, e.g., in the treatment of cancer or pathogen infection. A number of animal models of cancer are known which can be used to select an appropriate dose or administration protocol for carrying out a method or using a composition of the invention.

Colon adenocarcinoma in rodents induced by the procarcinogen 1,2-dimethylhydrazine and its metabolite azoxymethane (AOM) is a well-characterized carcinogen-induced tumor because of its morphological similarity to human colon cancer, high reproducibility and relatively short latency period (Shamsuddin, (1986) Human Path. 17:451-453). This rodent tumor model is similar to human colon adenocarcinoma not only in its morphology (Shamsuddin & Trump, (1981) J. Natl. Cancer Inst. 66:389-401) but also in the genes that are involved in tumorigenesis (Shivapurkar et al., (1995) Cancer Lett. 96:63-70; Takahashi et al., (2000) Carcinogenesis 21:1117-1120).

In addition to chemical carcinogen-induced models of colon cancer in rodents, gene disruption of the catalytic subunits of phosphoinositide-3-OH kinase (PI3-K$\gamma$) (Sasaki et al., (2000) Nature 406:897-902) or the guanosine-binding protein G$\alpha$i2 (Rudolph et al., (1995) Nat. Genet. 10: 143-50) causes spontaneous colon cancer in rodents. These studies indicate that potential causes other than alterations in the prototypical tumor suppressor genes and oncogenes could be involved in the etiology of human colon cancer.

A number of animal models for oral squamous cell carcinoma have been developed, including rat, mouse and hamster models. A hamster cheek pouch tumor model induced by the carcinogen 7,12-dimethylbenzanthracene remains one of the most common models (Baker (1986) Malignant neoplasms of the oral cavity. In: *Otolaryngology—Head and Neck Surgery*, Cummings et al. (eds.) pp. 1281-1343. St. Louis, Mo.: C V Mosby), but exhibits a number of differences from human oral cavity tumorigenesis. A recent mouse model using the carcinogen 4-nitroquinoline 1-oxide (4-NQO) has been developed which more closely simulates many aspects of human oral cavity and esophageal carcinogenesis (Tang et al. (2004) *Clin. Cancer Res.* 10: 301-313).

An animal model for multiple myeloma has been described (Garrett et al. (1997) *Bone* 20: 515-520), which uses a murine myeloma cell line 5TGM1 that causes lesions characteristic of human myeloma when injected into mice. Such lesions include severe osteolysis and the involvement of non-bone organs including liver and kidney. Mice inoculated with cultured 5TGM1 cells predictably and reproducibly develop disease, symptoms of which include the formation of a monoclonal gammopathy and radiologic bone lesions.

A number of animal models for the study of glioma exist, including an intracerebral rat glioma model (Sandstrom et al. (2004) *Br. J. Cancer,* 91: 1174-1180), and a murine model using injection of dog-derived J3T1 glioma cells (U.S. Pat. No. 6,677,155).

Animal models for the study of non-small cell lung cancer have been previously described, for example, by xenografting human tumors by subcutaneous transplantation of LC-6 human non-small cell lung cancer into BALB/C-nu/nu mice (Tashiro et al. (1989) *Cancer Chemother. Pharmacol.* 24, 187).

An animal model for the study of stomach cancer has been described which uses AZ-521 human stomach cancer xenografts in nude mice (Fukushima et. al. (2000) *Biochem. Pharmacol.* 59, 1227-1236).

Numerous animal models of AML have been previously described, including in rats (Blatt, J et al. (1991) *Leuk. Res.* 15:391-394), and SCID mice (Vey, N. et al. (2000) *Clin. Cancer Res.,* 6:731-736).

A number of animal models used for the study of HCC have been described (Chisari et al., (1985) *Science* 230: 1157-1160; Babinet et al., (1985) *Science* 230: 1160-11; U.S. Publication No. 2004/0016011). These references disclose the generation of transgenic mouse models of HCC by incorporating the HBV virus into the genome.

Animal models with experimental metastasis pattern resembling those frequently observed in human patients (Engebraaten & Fodstad, (1999) *Int. J. Cancer.* 82:219-25), which use MA-11 and MT-1, two estrogen and progesterone receptor-negative human breast cancer cell lines. Other models for breast cancer include U.S. Publication No. 2003/0215861 (herein incorporated by reference). Alternatively, the ability of the compounds of the present invention to function as anti-breast cancer agents, either alone or in combination with other agents, can be demonstrated in vivo in carcinogen induced mammary tumors in wild type Sprague-Dawley Rats (Thompson H. J et al, *Carcinogenesis,* (1992) 13:1535-1539).

A number of animal models for ovarian cancer are known in the art. For example, Connolly et al. ((2003) *Cancer Research,* 63, 1389-1397), discloses methods of developing epithelial ovarian cancer in mice by chimeric expression of the SV40 Tag under control of the MISIIR promoter. In another example, Liu et al. (*Cancer Research* 64, 1655-1663 (2004)) have introduced human HRAS or KRAS oncogenes into immortalized human ovarian surface epithelial cells, which form subcutaneous tumors after injection into immunocompromised mice.

Numerous animal models for the study of prostate cancer are available. One murine model, using prostate cancer xenografts introduced into SCID mice, is disclosed in U.S. Pat. No. 6,756,036. Alternatively, an orthotopic mouse model of metastatic prostate cancer can be used, as disclosed in U.S. Publication No. 2004/0009508.

EXAMPLES

The present invention is further illustrated by way of the following examples, which should not be construed as limiting in any way. Example 1 describes the materials and procedures used to make and test various embodiments of the invention in Examples 2 through 7.

Example 1

Materials and Methods

Cell Culture. The human embryonic kidney cell line 293 was cultured in DMEM culture media supplemented with 10% heat-inactivated fetal bovine serum (FBS) (Invitrogen, Carlsbad, Calif.), 100 U/mL penicillin, 100 µg/mL antimycotic and 100 µg/mL streptomycin at 37° C. in a 5% $CO_2$ atmosphere. Human breast cancer cell lines, MCF-7 and MDA-MD-231, human renal cancer cell line A498 and human ovary cancer cell line SK-OV-3 (ATCC) were maintained in RPMI 1640 media with 10% FBS, 100 U/mL penicillin, 100 µg/mL antimycotic and 100 µg/mL streptomycin at 37° C.

SOCS1 Downregulation and Western Blot Analysis. To assess human SOCS1 downregulation by siRNA, a computer program (www.dharmacon.com) was used to select siRNA sequences targeting human SOCS1. Three oligonucleotides were synthesized: siRNA1 (SEQ ID NO: 5), siRNA2 (SEQ ID NO: 6), and siRNA3 (SEQ ID NO: 7). 293T cells were co-transfected with a synthetic siRNA oligonucleotide duplex or an irrelevant scrambled oligo duplex and a flag-tagged human SOCS1 expression vector (pCMVhSOCS1) using GenePorter® reagent, following the manufacturer's protocol (Genlantis, San Diego, Calif.) (Shen et al., *Nat Biotechnol,* 22: 1546-1553, 2004). Briefly, 3 µL of a solution of 20 µM oligonucleotides was added to 3 µL of GenePorter reagent and 94 µL of serum-free RPMI1650. The mixture was incubated at 25° C. for 30 min, after which 100 µL of the GenePorter/oligonucleotide mixture was added to each well of PBMC-DCs and incubated for 4 h at 37° C. After incubation, 500 µL per well of RPMI1640 supplemented with 20% FBS was added to the PBMC-DCs.

For western blot analysis, the cells were harvested 48 h after transfection and subjected to SDS-PAGE, followed by transfer to Hybond-P membrane (Amersham, Piscataway, N.J.). Primary antibodies goat anti-human survivin (R&D Systems, Minneapolis, Minn.), mouse anti-human MUC1 (SeroTec, Oxford, UK) and rabbit anti salmonella H:I antibody (Santens Serum Institute) were used to detect the expression levels of survivin, MUC1 and flagellin, respectively. Mouse monoclonal antibody anti-Flag (Sigma, St. Louis, Mo.) were used to detected Flag-SOCS1 expression (Shen et al., *Nat Biotechnol,* 22: 1546-1553, 2004). The bound primary antibodies were detected by probing each blot with the appropriate HRP-conjugated anti-goat, anti-mouse, or anti-rabbit IgG, followed by detection with ECL-Plus reagent (Amersham, Piscataway, N.J.). Films were scanned with a Densitometer SI and bands were quantified with ImageQuant software (Molecular Dynamics, Sunnyvale, Calif.). The intensity of the bands were normalized to the intensity of the β-actin bands.

Quantitative RT-PCR Analysis. The relative expression of human SOCS1 in human DCs was evaluated by quantitative real-time RT-PCR. Briefly, total RNA was extracted from 3.5-5×10⁵ BM-DC using Trizol reagent (Invitrogen, Carlsbad, Calif.). One microgram (1.0 µg) of total RNA for each sample was reverse transcribed with random hexamer primers and SuperScript First-Strand Synthesis Kit (Invitrogen). Real-time 5'-nuclease fluorogenic PCR analysis was performed on an ABI 7900HT Sequence Detection System (Applied Biosystems) in 20 µl quadruplicate reactions with the equivalent of 5 ng starting RNA material per reaction as template. Pre-developed primer/probe sets for mouse SOCS1 (6FAM) and 18S ribosomal control (VIC) were purchased from Applied Biosystems (primers for SOCS1,5'-ACCT-TCTTGGTGCGCGAC-3' (SEQ ID NO: 161) and 5'-AAGC-CATCTTCACGCTGAGC-3' (SEQ ID NO: 162) and the hybridization probes, 5-6FAM-TCGCCAACGGAACT-GCTTCTTCG-TAMRA-3' (SEQ ID NO:163). PCR parameters were as recommended for the TaqMan Universal PCR Master Mix kit (Applied Biosystems), with SOCS1 and 18S reactions performed in separate tubes. SOCS1 levels were normalized to 18S rRNA, and SOCS1 expression relative to the control of mock-transfected, stimulated DCs was calculated by the comparative ΔΔCt method (Shen et al., *Nat Biotechnol*, 22: 1546-1553, 2004).

Generation of recombinant replication-defective adenoviruses. An Ad-Easy system (E1 and E3 deletion; Quantum Biotechnologies Inc., Palo Alto, Calif.) was used to construct and generate replication-defective adenoviruses, as described previously (Ren et al., *Cancer Res*, 64: 6645-6651, 2004). The DN truncated human survivin mutant gene was generated by PCR using the Thr34-Ala mutant hSVNT34A (Mesri et al., *J Clin Invest*, 108: 981-990, 2001) as a template with a pair of primers P-SF (5'-GAGTCGACATGAAGGACCACCG-CATCT-3', SEQ ID NO:164) and P-SR (5'-ACCAAGCT-TATCCATGGCAGCCAGCTG-3', SEQ ID NO:165). Oligonucleotide duplexes containing the human MUC1 three-repeat MUC1 sequence were synthesized by Operon and PCR amplified with primers P-MF (5'-ATTAACAAGCTTG-GTGTCACCTCGGC-3', SEQ ID NO:166) and P-MR (5'-TTAATTGCGGCCGCTTAGTGGGCTG-3', SEQ ID NO:167) to add cloning sites Hind III and Not I. The amplified survivin and MUC1 fragments were digested with restriction enzyme HindIII and ligated at room temperature for 1 h. The DN survivin mutant-MUC1 fusion fragment was then amplified by PCR with primers (P-SF and P-MR) to generate the DN survivin mutant-MUC1 fragment containing a Sal I restriction site at the 5' end and a NotI site at the 3' end. The modified flagellin (fliC) gene with a signal leader sequence from human tyrosinase was amplified by PCR using *Salmonella enterica* serovar *Typhimurium* (ATCC) as a template with a pair of primers SEQ ID NO: 168
(5'-TAGTCGACCTCGAGATGCTCCTGGCTGTTTTGTACTGCCTGCT
GTGGAGTTTCCAGACCTCCGCTGGCCATTTCCCTAGAATGGCACAAG
TCATTA-3',
and

SEQ ID NO: 169
5'-GGCTCTAGAGCGGCCGCTTAACGCAGTAAAGAGAGG-3',.

Encephalomyocarditis virus IRES sequence was amplified from the pShuttle-CMV-HSPIRES-E1A vector generated by Huang et al. (*Cancer Res*, 63: 7321-7329, 2003) with primers (5'-AATTGCGGCCGCTAAATTCCGCCCCTCT-3', SEQ ID NO:170 and 5'-GGCCTCGAGTGTGGCCATATTAT-CATCG-3 SEQ ID NO:171). Survivin-mucin-IRES fragment was constructed by ligation of NotI digested survivin-mucin fragment and IRES fragment. The resultant shuttle vector pshuttle-siSSF was constructed by inserting SalI/XhoI digested survivin mutant-MUC1-IRES fragment into a Sal I/Xho 1-digested pshuttle-SF vector, which was previously constructed by inserting the modified, secretory flagellin into an XhoI/XbaI-digested pshuttle-hSOCS1 vector. The pshuttle-hSOCS1 vector was generated by inserting the human H1 RNA promoter, human SOCS1-siRNA and transcriptional termination sequence PCR-amplified from the pSuper-hsiS1 vector into an Ad pshuttle vector. Subsequently, the recombinant replication-deficient Ad-siSSF virus containing the human SOCS1 siRNA under H1 RNA promoter (from pSuper vector), and DN human survivin mutant-MUC fusion gene linked to the modified flagellin with the encephalomyocarditis virus IRES sequence under the control of CMV promoter was generated according to the manufacturer's instruction. The insertion of these gene fragments in the recombinant Ad virus was confirmed by PCR and DNA sequencing. Recombinant adenoviruses were produced and titrated in 293 cells according to the manufacturer's instructions (Quantum Biotechnologies Inc., Palo Alto, Calif.).

Generation of human DC from peripheral blood mononuclear cells (PBMC) and Ad transfection. DCs from human PBMCs were performed as described in by Schroers et al. (Schroers et al., *Methods Mol Biol*, 246: 451-459, 2004; Schorers et al., *Clinical Can Res*, 9: 4743-4755, 2003). Briefly, PBMCs were isolated by Ficoll-paque (GIBCO-BRL, Grand Island, N.Y.) density gradient centrifugation of heparinized blood obtained from buffy coat preparations of healthy donors from the Gulf Coast Regional Blood Bank of Houston. Cells in the culture medium were seeded into 150-mm cell culture plates at the cell density of 5×10⁶ per mL. After 3 h of incubation at 37° C., nonadherent cells were removed and frozen at 1×10⁶ per mL for future use. The adherent blood monocytes were cultured in CellGro DC culture medium (Freiburg im Breisgau, Germany) supplemented with human recombinant granulocyte-macrophage colony-stimulatory factor (rhGM-CSF, 1,000 U/mL, R&D Systems, Minneapolis, Minn.) and interleukin-4 (rhIL-4, 1,000 U/ml, R&D Systems, Minneapolis, Minn.). rhGM-CSF and rhIL-4 were replenished every 3 d. On day 5 PBMC-derived DCs were harvested, reseeded onto 12-well culture plates at the cell density of 1×10⁶ per mL, and then transfected with different MOIs of Ad vectors in serum-free RPMI1640 medium for 1.5 h, followed by 48 h incubation in DC culture medium supplemented with 1000 U/mL rhIL4 and 1000 U/mL rhGM-CSF. Ad-transfected DCs were harvested and washed with serum-free RPMI1640 medium for further studies.

Flow cytometric analysis. Phenotypes of DCs and T cells were determined by flow cytometric assays. Fluorescein isothiocyanate (FITC)-, phycoerythrin (PE)- and (APC)-conjugated monoclonal antibodies (Mabs) against human CD40 (B-ly6), CD80 (L307.4), CD86 (2331), HLA-DR (TU39), HLA-A2 (BB7.2), CD11c (B-ly6) (BD Bioscience, Franklin Lakes, N.J.), OX40 ligand (OX40L) (ANC10G1), GITR ligand (GITRL) (109101), and CCR7 receptor (150503) (R&D Systems), and matched isotype controls were used for multiple color staining of DCs. FITC- or PE-conjugated MAbs against human CD4 (RPA-T4), CD8 (G42-8), and IFN-γ (4S.B3) (BD Bioscience, Franklin Lakes, N.J.) were used to stain T cells. DC viability was determined with anti-Annexin V staining (BD Bioscience, Franklin Lakes, N.J.). Mouse anti-human CD227 (MUC1, Clone C595, Serotec, Oxford, UK) were used to stain human tumor cell lines. Cells were washed and suspended in phosphate-buffered saline containing 2% FCS and 0.02% sodium azide.

For direct staining, cells were pre-incubated in 200 µg/mL of polyclonal human IgG (Sigma, St. Louis, Mo.) for 10 min on ice. Specific labeled Mabs or appropriate isotype controls were added, and cells were further incubated on ice for 25 min. For indirect staining, cells were preincubated with 200 µg/mL of polyclonal human IgG before incubation with anti-human CD227 Ab. Specific Mab was revealed with goat anti-mouse Ab labeled with FITC (Santa Cruz Biotechnology, Santa Cruz, Calif.). Staining with goat anti-mouse Ab labeled with FITC without primary antibodies was always performed in a separate tube as control. Stained cells were then analyzed on a FACSaria (Becton Dickinson, Franklin Lakes, N.J.) with FloJo software. ELISA and Cytokine Antibody Array assays Cytokine and chemokine concentrations in DC cultures were measured by commercially available two-site sandwich enzyme-linked immunosorbent assays (ELISA) from BD Bioscience (IL-6, IL-12, IL-10, TNF-α, IFN-γ and Rantes) according to manufacturers' instructions (Evel-Kabler et al., *J Clin Invest*, 116: 90-100, 2006). RayBio® Human Cytokine Antibody Array 3 (Ray Biotech, Norcross, Ga.) was used to detect the relative levels of 42 human cytokines and chemokines in the culture media of DCs according to the manufacturer's instruction.

Chemotaxis assay. DC migration was measured using a transwell system (24-well plates; 8 µM pore size; Costar, Corning, N.Y.) (Giordano et al., *Blood*, 107: 1537-1545, 2006.). Human PBMC-derived DCs transfected with different Ad vectors for 48 h were collected and seeded into 24-well transwell plates (5 µM pore size) in upper chambers (100 µL of $1\times10^5$ cells per well). Five-hundred microliters (500 µL) of DC culture medium with 100 ng/ml CCL21 (Genetex, San Antonio, Tex.) or only culture medium was plated in the lower chambers. Wells with medium only were used as a control for spontaneous migration. After culture for 3 h at 37° C., 500 µL medium in the lower well was collected and cell numbers were calculated with FACS collection for 50 s. The counts fell within a linear range of the control titration curves obtained by testing increasing concentrations of cells. The mean number of spontaneously migrated cells was subtracted from the total number of cells that migrated in response to the chemokine. Migration rate (%)=(Cell number in CCL21 medium−Cell number in DC medium)/(Cell number in DC medium)×100.

Endocytotic assay of human DC. The endocytotic capability of PBMC-derived DCs was tested using Dextran-Texas Red, as previously reported (Sallusto et al., *J Exp Med*, 182: 389-400, 1995). $1\times10^6$ cells human PBMC-derived DCs were transfected with different Ad vectors at a MOI of 25,000 vp. Forty-eight hours (48 h) later, $2\times10^5$ transfected DCs were pulsed with Dextran-Texas Red (Invitrogen, Carlsbad, Calif.) at a concentration of 1 mg/mL for 4 h. Cold staining buffer (1% FBS in PBS) was added to stop the reaction. The cells were washed four times and stained with PE-conjugated anti-CD11c Abs, and then analyzed on a FACSaria. Nonspecific binding of dextran to DCs, determined by incubation of DCs with Dextran-Texas Red at 4° C., was shown. The medium used in the culture was supplemented with GM-CSF, because the ability of DCs to capture Ag is lost if DCs were cultured without GM-CSF (Inaba et al., *J of Exp Med*, 176: 1693-1702, 1992).

In vitro T cell sensitization. In vitro sensitization of autologous T cells was performed as reported (32, 36, 37). $1\times10^6$ human PBMC-derived DCs were mock-transfected or transfected with Ad vector at an MOI of 25000 vp for 1.5 h in 1 mL serum-free RPMI1640 medium in 12-well culture plate, followed by the addition of 1 ml DC culture medium with 20% FBS for 48 h. Transfected DCs were harvested, washed with RPMI1640, and then cocultured with autologous T cells at a DC: effector ratio of 1:20 in 2 min DC culture medium without rhIL-4 and rhGM-CSF at 37° C., in a humidified atmosphere containing 5% $CO_2$ for 7 days. Every 3 days, the cultures were replenished with recombinant human IL-2 (R&D Systems, Minneapolis, Minn.) at a concentration of 50 U/mL. The T cells were restimulated weekly with freshly prepared mock or Ad-transfected autologous DCs. After 14 d of cocultures, the T cells were collected for intracellular cytokine staining, ELISPOT and CTL assays.

In vitro T cell proliferation and suppression assays. To assess the effect of Ad-transfected DCs on Treg function, human PBMC-derived DCs (day 5) were transfected with different Ad vectors at an MOI 25000 vp for 48 h as described above. Human CD4+CD25+ Treg cells and CD4+CD25− Teff cells from different donors were isolated by using human CD4+CD25+ MACS kit (Miltenyi Biotec, Auburn, Calif.) as specifications. Ad-transfected DCs ($5\times10^5$) were cocultured with autologous CD4+CD25+ Treg cells ($1\times10^5$) for 5 d in 12-well cell culture plate. CD4+CD25+ Treg cells ($1\times10^5$) were purified with CD4+CD25+ MACS kit and cocultured with $1\times10^5$ CD4+CD25− Teff cells and $5\times10^4$ autologous mock DC in the presence of 0.5 µg/mL of anti-human CD3 for another 60 h in 96-well plates. One microcurie (1 µCi) of [$^3$H] thymidine (DuPont NEN, Wilmington, Del.) were then added into each well and incubated for another 16 h. The cells in triplicate wells were harvested onto fiberglass filters using Filter Mate Harvester (Packard), and filters were washed extensively. After drying, 25 µL of MicroScint 20 (Packard) were added into each well, and radioactivity was counted with a TopCount NXT Microplate Scintillation and Luminescence Counter (Packard). In parallel, $1\times10^5$ allogenic CD4+CD25− T cells were labeled with 20 µM CFSE (Invitrogen, Carlsbad, Calif.) for 15 min at 37° C. The CFSE-labeled T cells were added to above coculture system to monitor proliferation.

ELISPOT assays. ELISPOT assays were performed as described previously (Schroers et al., *Methods Mol Biol*, 246: 451-459, 2004; Schorers et al., *Clinical Can Res*, 9: 4743-4755, 2003), with some modifications. Briefly, MultiScreen-HA plates (Millipore, Bedford, Mass.) were coated overnight at 4° C. with 10 µg/mL of the antihuman IFNγ mAb 1-D1K (Mabtech, Stockholm, Sweden) in coating buffer (carbonate-bicarbonate buffer (pH 9.6)). Plates were blocked with RPMI 1640 and 10% human serum (Bethyl, Inc., Montgomery, Tex.) for at least 2 h at 37° C. Stimulated T cells were seeded at $2\times10^5$ per well and cocultured with irradiated $4\times10^3$ autologous DCs without Ad transfection in the presence of 20 µg/mL HLA-A2-restricted survivin peptide (ELTLGEFLKL, SEQ ID NO: 172) (Schmidt et al., *Blood*, 102: 571-576, 2003) and 20 µg/ml HLA-A2-restricted MUC1 peptide (STAPPAHGV, SEQ ID NO: 173) (Brossart et al., *Blood*, 93: 4309-4317, 1999; Brossart et al., *Blood*, 96: 3102-3108, 2000) at 37° C., 5% $CO_2$ in triplicate. Plates were incubated at 37° C. in a humidified 5% $CO_2$ incubator for 16 h, and cells were then removed by six washes with PBS-0.05% Tween 20 (Sigma, St. Louis, Mo.). Biotinylated antihuman IFNγ antibody 7-B6-1 (Mabtech, Stockholm, Sweden) at a concentration of 1 µg/ml in PBS-0.5% human serum was added, and plates were incubated for 2 h at 37° C. Streptavidin-conjugated alkaline phosphatase (Mabtech, Stockholm, Sweden) was added for an additional 1 h. Cytokine-producing cells were detected after a 4 min reaction with 5-bromo-4-chloro-3-indolylphosphate and nitroblue tetrazolium (Life Technologies, Inc., Gaithersburg, Md.). The results were evaluated in a blinded fashion by ZellNet Consulting, Inc. (New York, N.Y.) with an automated ELISPOT reader system (Carl Zeiss, Inc., Thornwood, N.Y.), using KS ELISPOT 4.3 software.

CTL assays. CTL standard $^{51}$Cr-release assay was performed, as described by Schroers et al. (*Cancer Res,* 62: 2600-2605, 2002). DC-sensitized T cells were re-stimulated with 20 µg/mL MUC1 and 20 µg/mL survivin peptides-pulsed autologous DCs without Ad transfection for 2 h. Target cells (MCF7, A498, SK-OV3 and MDA-MB-231) were labeled with [$^{51}$Cr]-sodium chromate in RPMI 1640 for 1 h at 37° C. Target cells (104) were transferred to wells of round-bottomed 96-well plates. Various numbers of DC-sensitized T cells were added to give a 16 final volume of 200 µL and incubated for 4 h at 37° C. At the end of the assay, supernatants (50 µL/well) were harvested and counted in a beta-plate counter. The percentage of cell lysis was calculated as follows: 100× (experimental release–spontaneous release/maximal release-spontaneous release). Spontaneous and maximal releases were determined in the presence of either medium or 1% SDS, respectively.

Example 2

Construction and Characterization of Recombinant Ad Vector Ad-siSSF

In accordance with one embodiment of the present invention, a recombinant expression construct was designed to coexpress an inhibitor of a negative immune regulator, a proinflammatory molecule, and an antigen. In particular, this Example describes the construction of a recombinant replication-deficient adenoviral vector was designed to coexpress a small hairpin human SOCS1-siRNA (siSOCS1), dominant negative (DN) survivin and MUC1 fusion protein, and a secretory flagellin, the TLR5 ligand (FIG. 1). The vector was assembled using PCR amplification of individual gene segments, as described in Example 1.

In order to construct the recombinant replication-deficient adenoviral vector, designated as Ad-siSSF, which coexpresses a small hairpin human SOCS1-siRNA (siSOCS1), dominant negative (DN) survivin and MUC1 fusion protein, and a secretory flagellin, the TLR5 ligand (FIG. 1), survivin, MUC1, and flagellin genes were modified. Furthermore, one example of a siRNA that can effectively silence human SOCS1 was identified. The adenoviral vector system was selected, because of its high transfection efficiency of human DCs, well-established Ad manufacture system, the transient nature of transgene expression that limits the potential risk of autoimmune toxicity, and the demonstrated safety in more than a thousand humans (Song et al., *J Exp Med,* 186: 1247-1256, 1997; van Ginkel et al., *J Immunol,* 159: 685-693, 1997; Dietz et al., *Blood,* 91: 392-398, 1998; Barouch et al., *Hum Gene Ther,* 16: 149-156, 2005; Shiver et al., *Annu Rev Med,* 55: 355-372, 2004).

Because of the anti-apoptotic biological activity of survivin for the potential promotion of malignant cell survival and transformation, two mutations were introduced into the survivin gene to generate a DN survivin mutant. A substitution mutation of Thr with Ala in position 34 was made to eliminate the p34cdc2-cyclin B1 phosphorylation site and anti-apoptotic activity, as described previously (O'Connor et al., *Proc Natl Acad Sci USA,* 97: 13103-13107, 2000). Moreover, to avoid possible reverse mutation of the surviving mutant back to a functional phosphorylation site, a 16 amino acid truncation at the N-terminus of survivin was further made since the N-terminal sequence is required for its inhibition of apoptosis (Sun et al., *Nature,* 401: 818-822, 1999). A short human mucin 1 (MUC1) fragment containing only a three 20 amino acid tandem repeat sequence was used, because a known dominant T cell epitope is located within the 20 amino acid repeat (Fontenot et al., *J Biomol Struct Dyn,* 13: 245-260, 1995) and full-length or lengthy MUC1 protein was found to have immune suppressive activity by inhibiting a Th1-type CTL response (Carlos et al., *J Immunol,* 175: 1628-1635, 2005).

To generate a DN survivin-MUC1 fusion gene (DN SM) as target tumor-associated antigens for the Ad-siSSF vector, the double mutated DN survivin was genetically linked in-frame to the three 20 amino acid repeat fragment of MUC1. For facilitating the secretion and subsequent interaction with surface TLR5 on DCs of flagellin by transfected DCs, a signal leader sequence derived from human tyrosinase was genetically linked to the N-terminus of the flagellin gene.

Using the computer program described in Example 1, small interfering RNAs (siRNA) with the ability to specifically downregulate human SOCS1 were identified (siRNA1, siRNA2, and siRNA3). FIG. 2 shows that human SOCS1 siRNA1, but not SOCS1 siRNA2 and siRNA3, efficiently downregulated human SOCS1 expression. The specificity of human SOCS1 mRNA down-regulation by siRNA was confirmed by the inability of a scrambled siRNA1 oligonucleotide duplex (mut) to down-regulate SOCS1 mRNA. Human SOCS1 siRNA1 (SEQ ID NO: 5) was therefore selected for the construction of Ad-siSSF vector.

The resultant Ad vector Ad-siSSF was constructed, as schematically shown in FIG. 1, and insertion of these genes in the recombinant adenovirus was confirmed by DNA sequencing. In addition, an adenovirus vector Ad-SM that only expresses the DN SM fusion protein and an adenovirus vector Ad-GFP expressing a GFP marker were constructed and produced as controls (FIG. 1).

Figure 3B:
FIG. 3B is a western blot analysis of human SOCS1 downregulation in 293T cells that were transfected with a human SOCS1 expression vector DNA and infected with different MOIs (0, 10, 100, 1,000, 10,000, and 20,000 vp; lanes 1-6 of FIG. 3B, respectively) of Ad-siSSF or control Ad-GFP (MOIs of 10, 100, 1,000, 10,000, and 20,000 vp; lanes 7-11 of FIG. 3B, respectively).
Figure 3C:
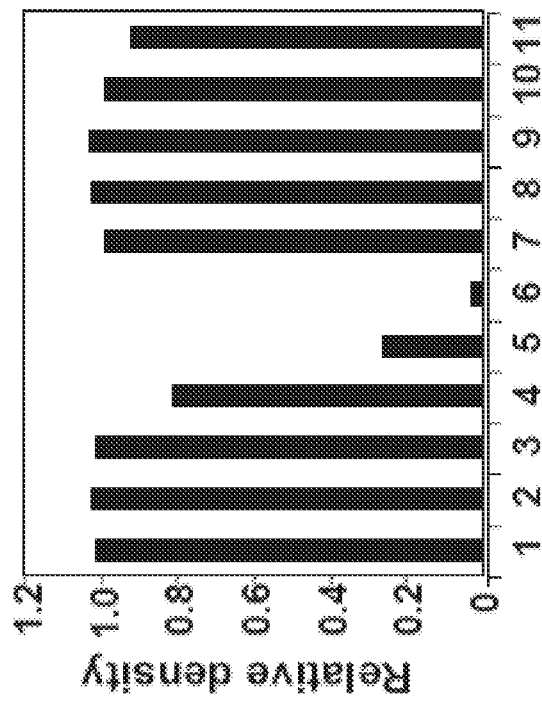
FIG. 3C is a quantitative analysis of the western blot of FIG. 3B by densitometry. Relative density of the human SOCS1 band to actin is shown in the histogram.
Figure 3A:
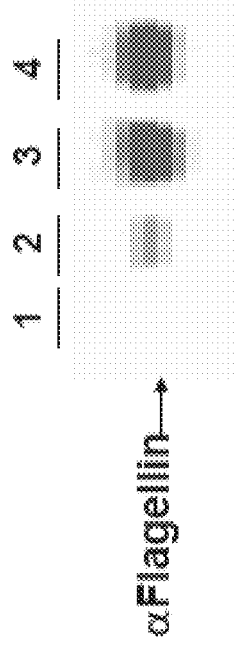
FIG. 3A is a western blot of the dominant negative (DN) survivin-MUC1 fusion protein and flagellin in 293T cells that were transfected with different multiplicities of infectivity (MOIs) (10, 100, 1000, and 10000 viral particles (vp), lanes 1-4, respectively) of Ad-siSSF.

The ability of the Ad-siSSF virus to efficiently coexpress the three components of siSOCS1, DN SM fusion protein, and secretory flagellin in transfected cells was demonstrated by Western blotting analysis. FIG. 3A shows the expression of the DN survivin-MUC1 fusion protein and flagellin in 293T cells that were transfected with different MOIs (10, 100, 1000, and 10000 vp, Lanes 1-4) of Ad-siSSF. MOIs of 100 vp or higher showed good expression of the polypeptides. FIG. 3B shows a western blot of the lysates of 293T cells that were transfected with a human SOCS1 expression vector DNA and infected with different MOIs (0, 10, 100, 1,000, 10,000, and 20,000 vp) (Lanes 1-6) of Ad-siSSF or control Ad-GFP (MOIs of 10, 100, 1,000, 10,000, and 20,000 vp; Lanes 7-11). Relative density of the human SOCS1 band to actin is shown in the histogram (FIG. 3C). A MOI of 1,000 vp or greater is able to significantly decrease the expression of SOCS1 in 292T cells, while simultaneously providing good expression of flagellin and the DN surviving-MUC1 fusion protein. Thus, the results in this Example demonstrate that polynucleotides encoding an inhibitor of a negative immune regulator, a proinflammatory molecule, can be coexpressed in the same cell.

Example 3

Efficient Maturation of Human DCs by Ad-siSSF

In accordance with one aspect of the present invention, a vaccine composition comprising polynucleotides encoding an inhibitor of a negative immune regulator, a proinflammatory molecule, and an antigen was administered to DCs in order to induce their maturation.

Figure 4:
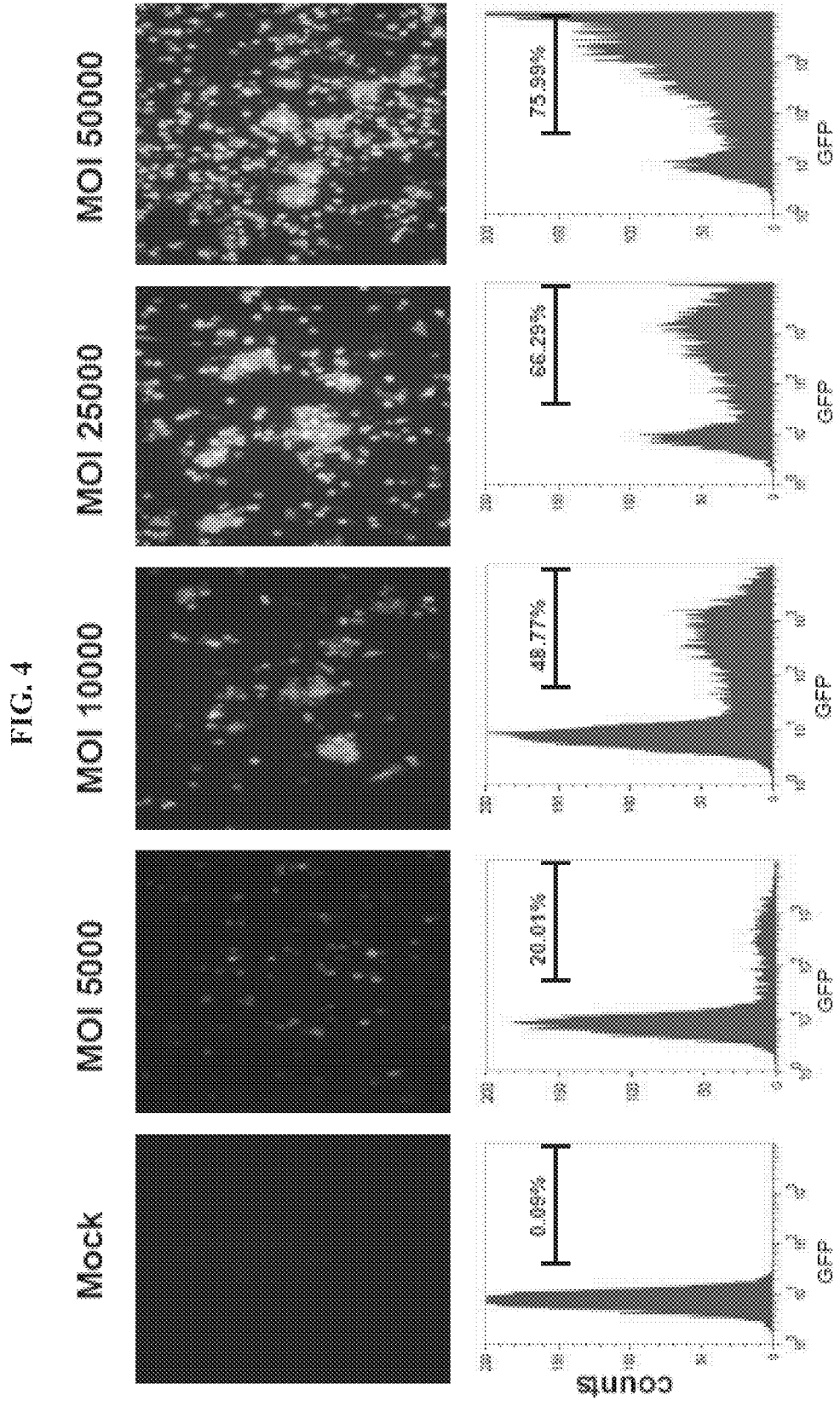
FIG. 4 presents fluorescence micrograph (upper row of panels) and flow cytometry data (lower row of panels) of human DCs transfected with Ad-GFP at different MOIs.
Figure 5:
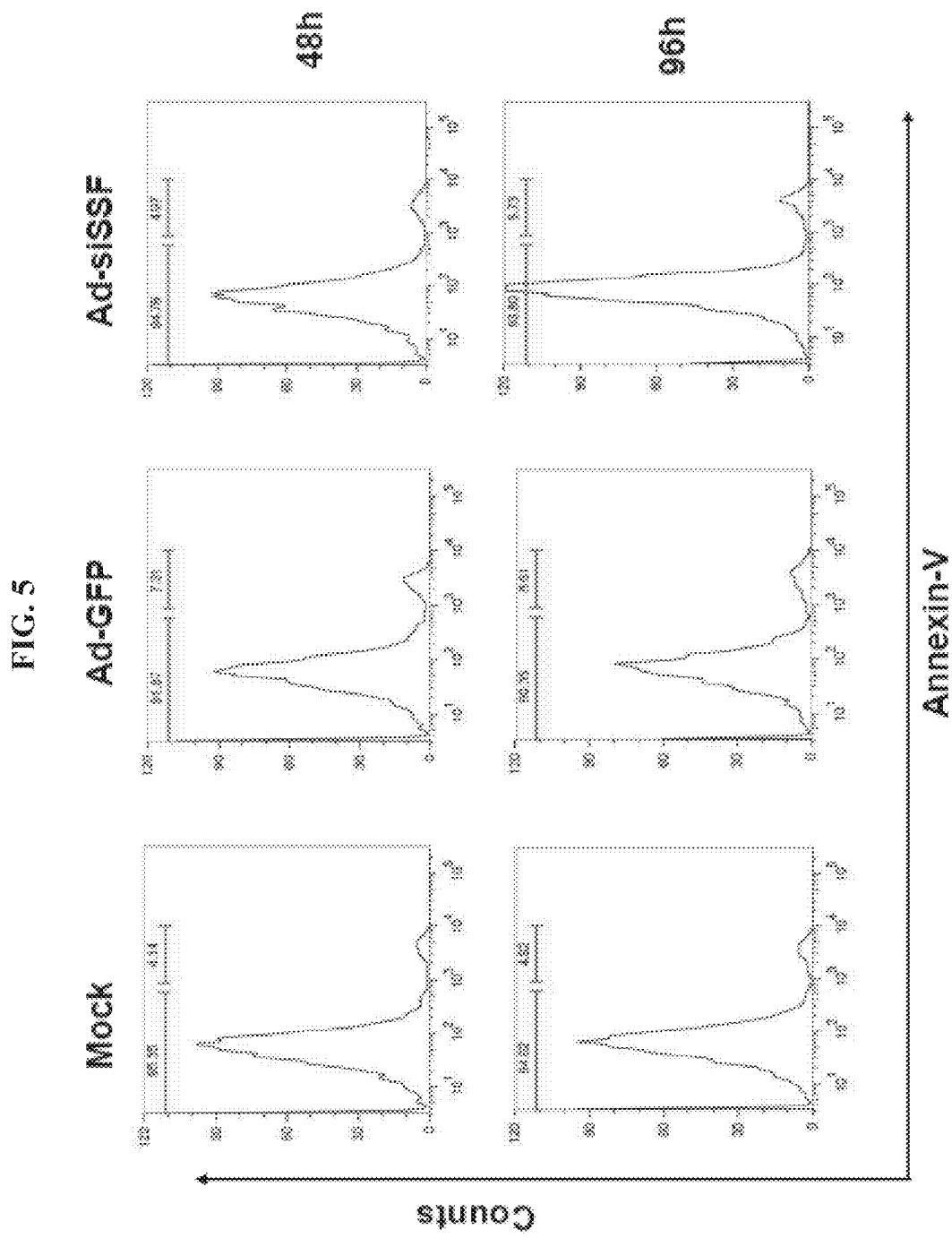
FIG. 5 is a graph of flow cytometry data showing the viability of Ad-siSSF transfected PBMC-DCs as evidenced by Annexin-VI (BD Bioscience) staining at 48 h and 96 h post-transfection from one of three repeated experiments.

The polynucleotides were provided in the Ad-vector as described in Example 2. First, a suitable MOI (multiplicity of infectivity) of Ad vector was determined which would allow for efficient transfection of human PBMC-derived DCs, but would not have significant toxicity. The transfection efficiency of human PBMC-derived DCs was determined by examining the percentage of GFP+ DCs after 24 h of Ad-GFP transfection. With a MOI of 25,000 or 50,000 viral particles (vp), about 66% or 75% of DCs, respectively, were transfected when examined 24 h post-transfection (FIG. 4). DC viability of DCs at different times after transfection with Ad-siSSF or Ad-GFP was determined by trypan blue, propidium iodide (PI), and Annexin-V staining. When the MOI of 25,000 vp was used, the majority of Ad-siSSF-transfected DCs were still viable (>94%) as evidenced by staining at 48 h and 96 h post-transfection (FIG. 5). However, transfection with higher MOIs caused considerable toxicity to DCs with a reduced percentage of their viability. Thus, a MOI of 25,000 vp for Ad transfection of human PBMC-derived DCs was chosen for use in the following studies.

Figure 6:
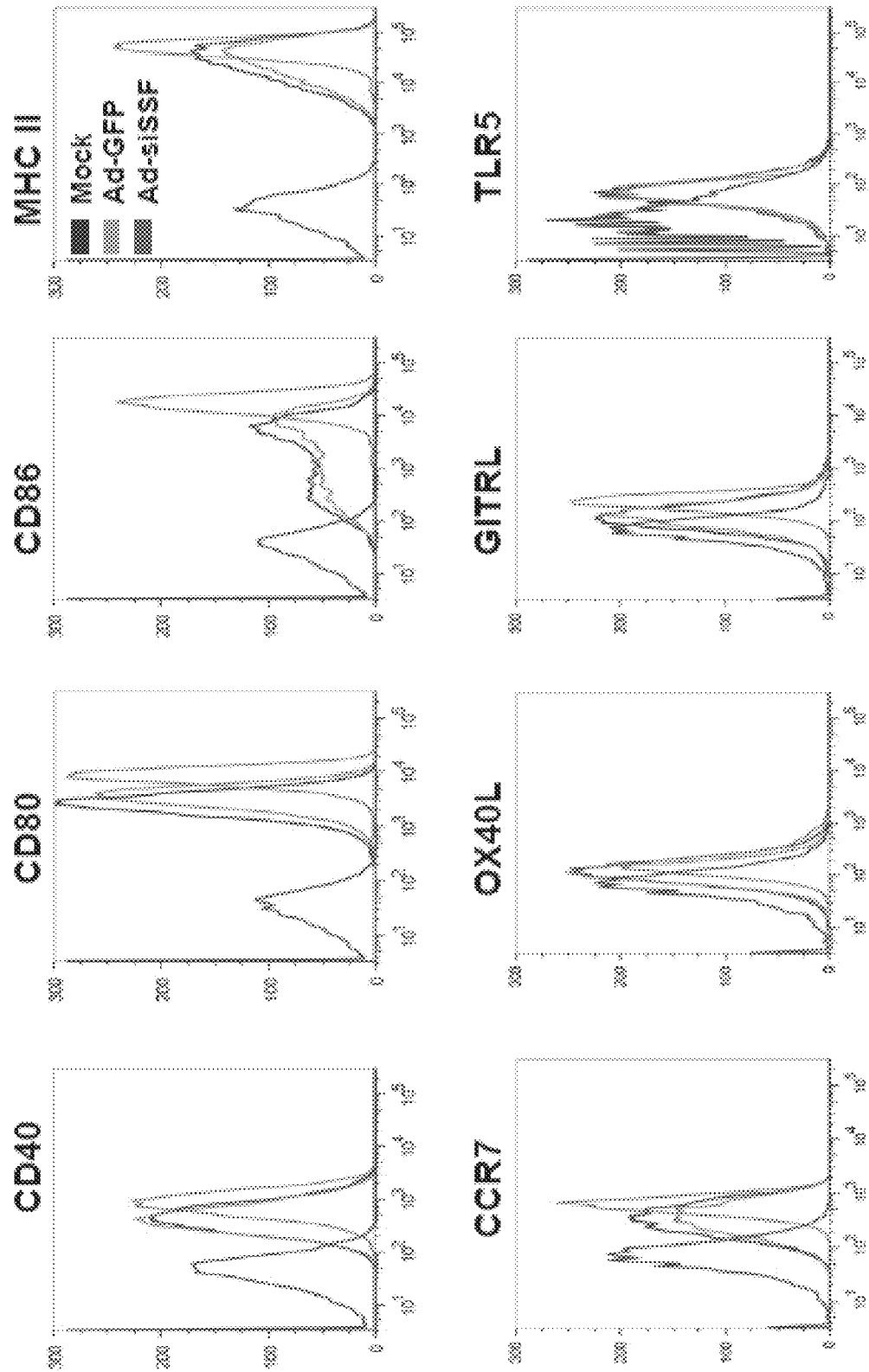
FIG. 6 is a series of graphs of flow cytometry data showing enhanced maturation of Ad-siSSF-transfected human DCs. The expression levels of a panel of surface markers on human PBMC-DCs at 48 h post-transfection with Ad-siSSF and control Ad-GFP virus (MOI=25,000 vp) from one of three repeated experiments are shown.
Figure 7:
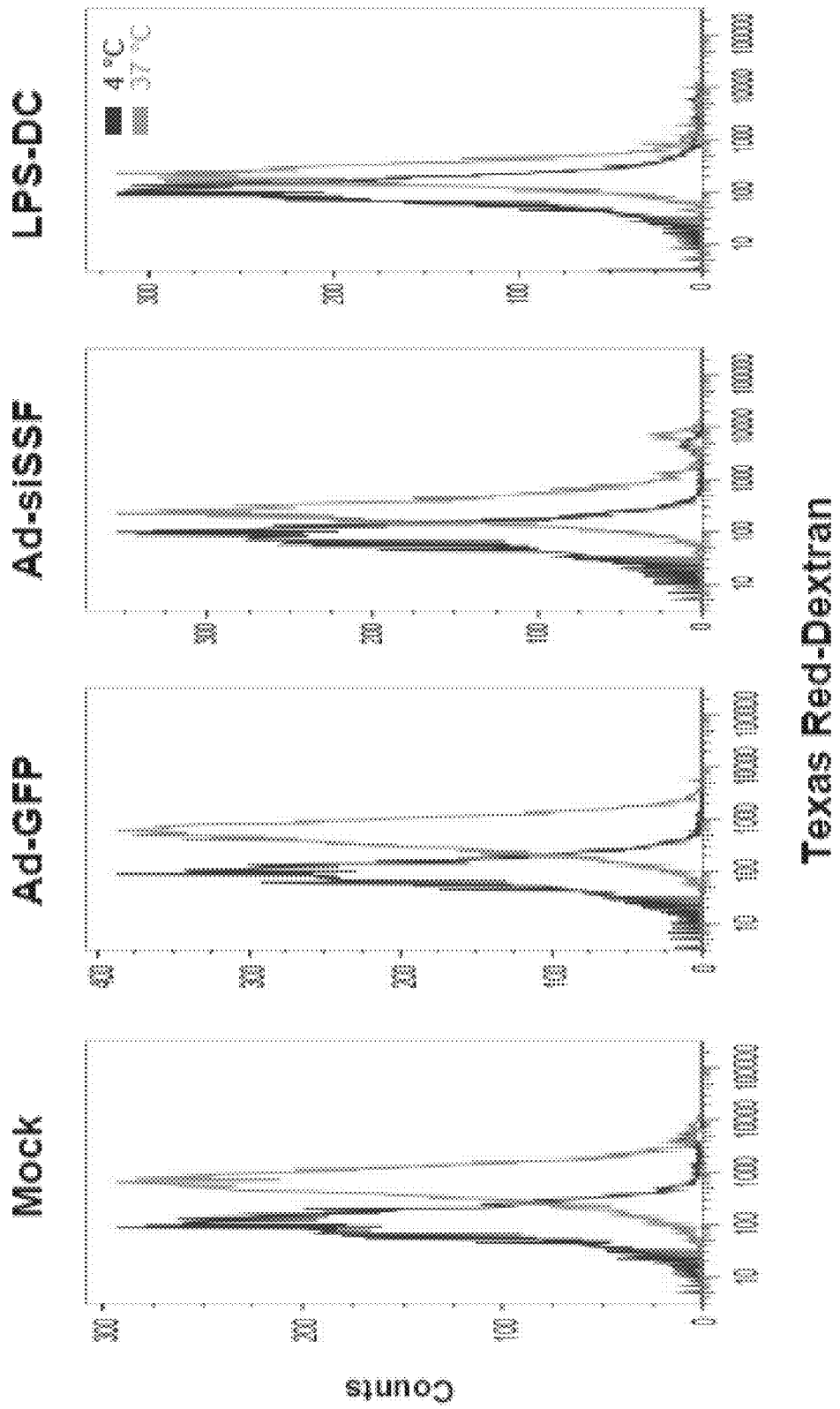
FIG. 7 is a series of graphs of flow cytometry data showing endocytic activity of Ad-siSSF-transfected human DCs. The percentages of transfected human PBMC-DCs internalizing Dextran-Texas-Red (Invitrogen, Carlsbad, Calif.) after 90 min incubation at 4° C. or 37° C. were evaluated by FACS from one of three repeated experiments.

Next, the effect of Ad-siSSF transfection on the maturation of human PBMC-derived DCs by flow cytometric assays was examined. The flow cytometric methods and antibodies used for detection are described in Example 1. FIG. 6 shows that levels of surface costimulatory molecules, such as CD40, CD80, and CD86, and MHC class II molecules were significantly upregulated on Ad-siSSF-transfected DCs at 48 h post-transfection, compared those on Ad-SM transfected DCs. Surface levels of members of the tumor necrosis factor receptor (TNFR) family such as GITR (glucocorticoid-induced tumor necrosis factor receptor) ligand and OX40 ligand (T-cell costimulatory signal ligand) were also significantly enhanced on Ad-siSSF-DCs (FIG. 6). TLR5 was expressed on human PBMC-derived DCs, but its expression was not upregulated by Ad-siSSF transfection. Furthermore, it was shown that Ad-siSSF-transfected DCs retained the endocytic ability to internalize Texas Red-conjugated dextran (FIG. 7) after 90 min incubation at 4° C. or 37° C.

Thus, in accordance with the vaccine aspect of the present invention, these results demonstrate the potency of the Ad-siSSF vector expressing an inhibitor of a negative immune regulator, a proinflammatory molecule, and an antigen to efficiently promote human DC maturation as evidenced by the increased expression of surface costimulatory molecules.

Example 4

Figure 8:
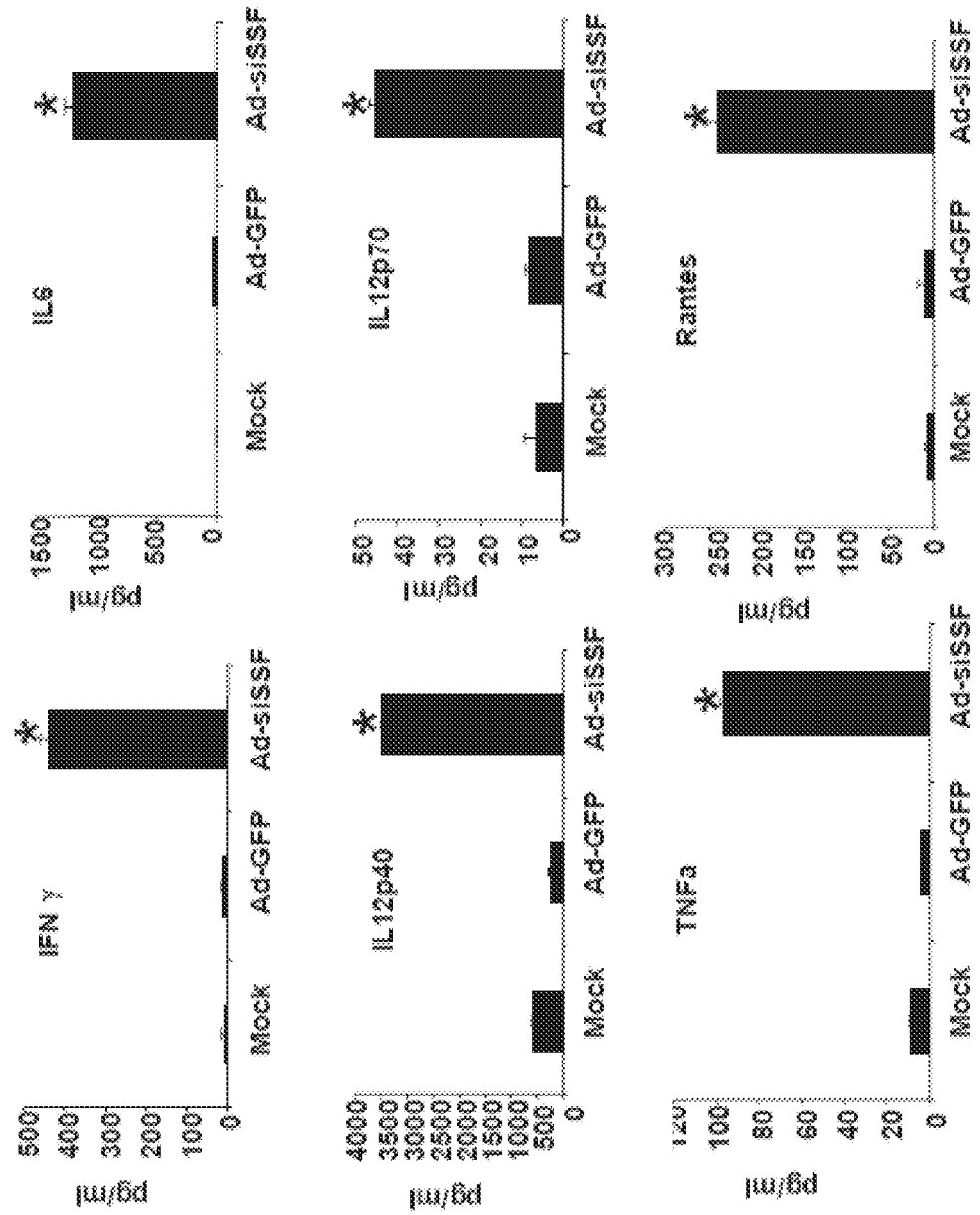
FIG. 8 is a series of graphs showing the quantitation by ELISA of proinflammatory cytokines and chemokines produced by Ad-siSSF-transfected human DCs.

Robust Production of Proinflammatory Cytokines by Human DCs Transfected with Ad-siSSF In this Example, an embodiment of the vaccine compositions of the present invention was examined for its effects on the production of proinflammatory cytokines by transfected human PBMC-derived DCs. Cytokines are critically involved in the regulation of activation, proliferation, and differentiation of immune cells. Recent studies suggest that cytokines produced by DCs function as a third signal for the priming and activation of T and B cells (Curtsinger et al., *J Exp Med*, 197: 1141-1151, 2003; Valenzuela et al., *J Immunol*, 169: 6842-6849, 2002). Studies of mouse DCs demonstrated the enhanced production of proinflammatory cytokines by SOCS1-siRNA-transduced DCs (Shen et al., *Nat Biotechnol*, 22: 1546-1553, 2004; Evel-Kabler et al., *J Clin Invest*, 116: 90-100, 2006). As described in Example 1, human DCs were transfected with Ad-siSSF or control Ad-GFP or Ad-SM and, at different times post-transfection, the culture media were collected for cytokine ELISA assays. FIG. 8 shows the enhanced production of representative proinflammatory cytokines such as IL-12p40, IL-12p70, IFN-γ, IL-6, and TNF-α by Ad-siSSF-DCs, compared to Ad-GFP-DCs.

Figure 9:
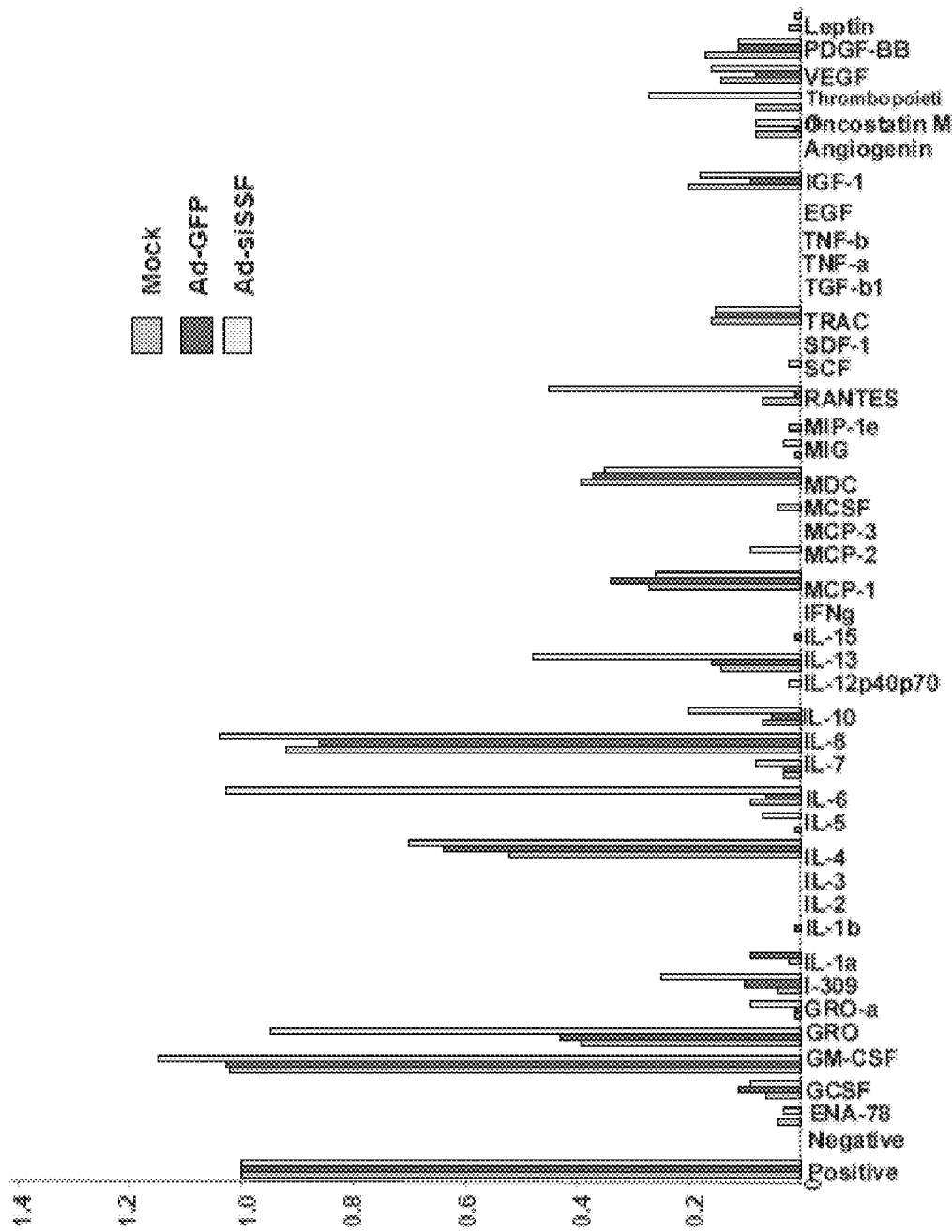
FIG. 9 is a graph showing the quantitation by RayBio® Human Cytokine Antibody Array 3 (detecting 42 cytokines) (Ray Biotech, Norcross, Ga.) of proinflammatory cytokines and chemokines produced by Ad-siSSF-transfected human DCs.

To further assess the effect of Ad-siSSF transfection on cytokine production by DCs, the RayBio® Human Cytokine Antibody Array (Ray Biotech, Norcross, Ga.) was used to detect 42 cytokines in the culture media of Ad-transfected DCs. It was found that the production and secretion of various proinflammatory cytokines were broadly upregulated in Ad-siSSF-transfected DCs (FIG. 9). Moreover, ELISA assays showed that chemokines such as RANTES were significantly elevated in Ad-siSSF-DC culture (FIG. 8). In supporting the ELISA data, human cytokine array data also showed the enhanced levels of chemokines, such as MIP3 and RANTES, in the culture media of Ad-siSSF transfected DCs. Taken together, these results indicate that transfection with Ad-siSSF effectively stimulates the maturation of human PBMC-derived DCs as well as their production of a broad array of proinflammatory cytokines and chemokines.

Example 5

Efficient Trafficking of Ad-siSSF-DCs

In this Example, an embodiment of the vaccine compositions of the present invention was examined for its effects on the migration of transfected human PBMC-derived DCs. The migration of antigen-presenting DCs into draining lymph nodes where they prime antigen-specific T and B cells is critical for the induction of antitumor immunity in immunized cancer patients. DCs after maturation express their main lymph node-homing chemokine receptor, CC-chemokine receptor 7 (CCR7), to migrate to lymph nodes by responding to a chemotactic gradient of CCR7 ligands, CCL19 and/or CCL21, that originates from peripheral lymphatic vessels (51). Interestingly, it was observed that the level of chemokine receptor CCR7 was significantly upregulated on Ad-siSSF-transfected DCs, compared to that on the control Ad-GFP-DCs (FIG. 6). Consequently, the significantly higher levels of CCR7, a key lymph node homing receptor, expressed by transfected cells suggests that the vaccine composition may enhance the migration ability of AdsiSSF-DCs to draining lymph nodes in immunized patients.

Figure 10:
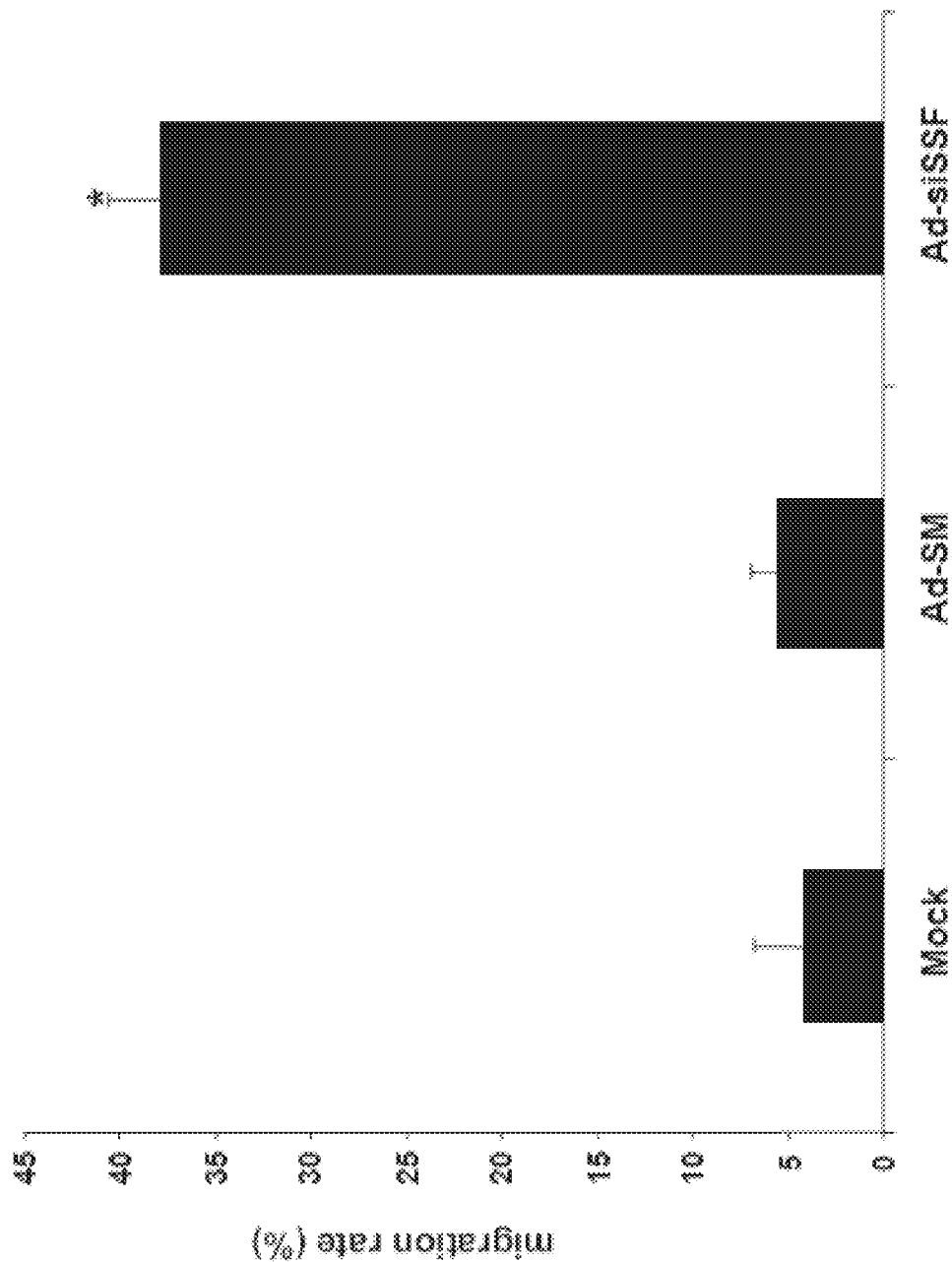
FIG. 10 is a graph showing enhanced migration activity of Ad-siSSF-transfected DCs. Migration rates of transfected human PBMC-DCs in response to recombinant CCL21 (Genetex, San Antonio, Tex.) (100 ng/mL) are presented from one of three repeated assays. P<0.05, Ad-siSSF vs. Ad-SM DCs.

Next, the migration ability of Ad-siSSF-DCs was examined by using transwell migration assays in vitro, as described in Example 1. Human PBMC-derived DCs were transfected with Ad-siSSF or control Ad-SM and then added to the upper compartment of the transwell in triplicate. Recombinant CCL21, a CCR7 ligand, was added to the lower compartment and the migration rates of Ad-transfected DCs were then determined after 3 h incubation. FIG. 10 shows a significantly (P<0.05) increased migration rate of Ad-siSSF-transfected DCs in response to CCL21, compared to that of Ad-SM-transfected DCs, suggesting an enhanced migration ability of Ad-siSSF transected DCs to draining lymph nodes of immunized patients, likely as a result of the elevated expression of chemokine receptors. Thus, these results indicate that the vaccine compositions of the present invention are able to efficiently stimulate migration of DCs, and may enhance the ability of DCs to localize to lymph nodes upon administration to patients.

Example 6

Vigorous Immunostimulatory Potency of Ad-siSSF-DCs to Activate CTLs

Figure 11:
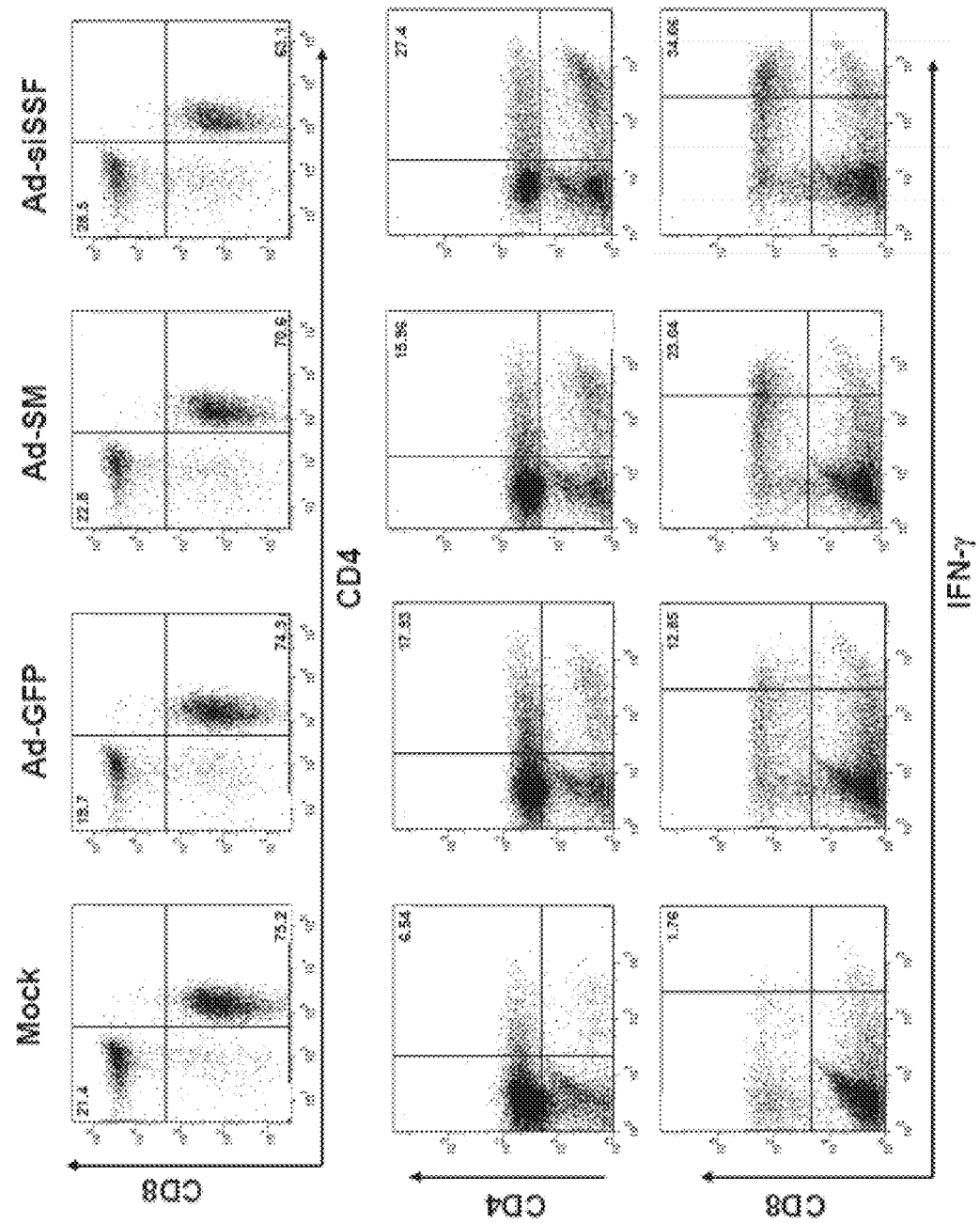
FIG. 11 is a series of graphs from ELISPOT assays demonstrating enhanced priming of TAA-specific T cells by Ad-siSSF-DCs. Human autologous T cells were cocultured with Ad-transfected DCs (20:1) for 2 weeks. The cocultured CD4+ and CD8+ T cells were then stained for intracellular IFN-γ.
Figure 12:
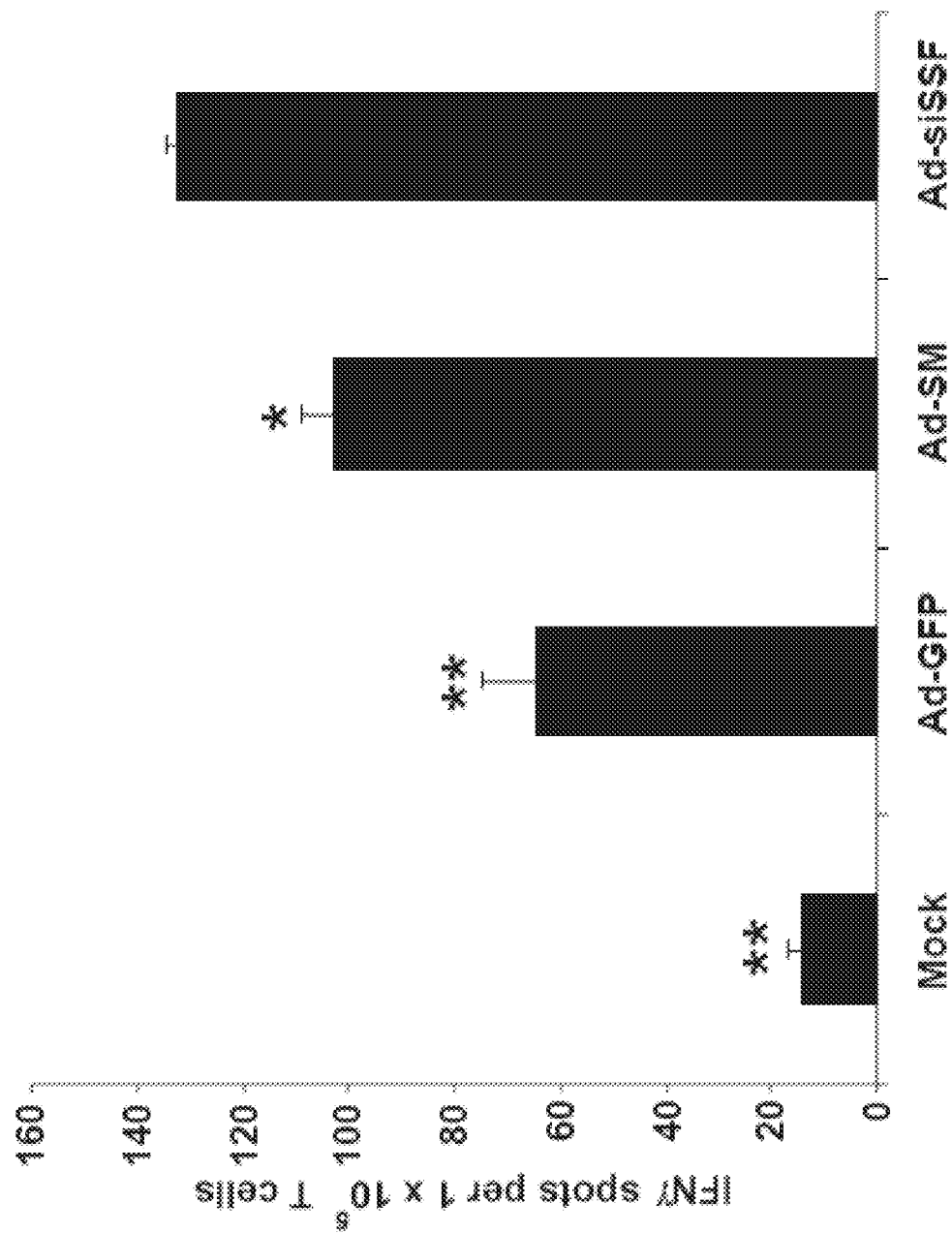
FIG. 12 is a chart summarizing the data in FIG. 11. Representative data from one HLA-A2+ donor out of 5 HLA-A2+ donors are shown. P<0.05, Ad-siSSF vs. Ad-SM.

In one aspect, the present invention provides vaccine compositions that stimulate CTL responses against cells expressing various antigens. The immunostimulatory potency of Ad-siSSF-DCs to prime antigen-specific CTLs was tested using an in vitro T cell sensitization assays, as described in Example 1. HLA-A2+ human PBMC-derived DCs were transfected with Ad vectors and then cocultured with autologous T cells for 2 weeks. The numbers of antigen-specific T cells in the cocultures were determined by IFN-γ ELISPOT and intracellular staining assays after restimulation with survivin and MUC1 peptides-pulsed autologous DCs that were not transfected with Ad. IFN-γ intracellular staining assays showed enhanced percentages of IFN-γ producing CD8+ T cells and CD4+ T cells in the coculture with Ad-siSSF-DCs, compared to Ad-SM-DCs (FIG. 11). In agreement, IFN-γ ELISPOT assays show the enhanced numbers of IFN-γ producing T cells in the Ad-siSSF-DC cocultures (FIG. 12). Thus, these results indicate that DCs transfected with Ad-siSSF have powerful immunostimulatory potency to prime antigen-specific CTL responses.

Figure 13B:
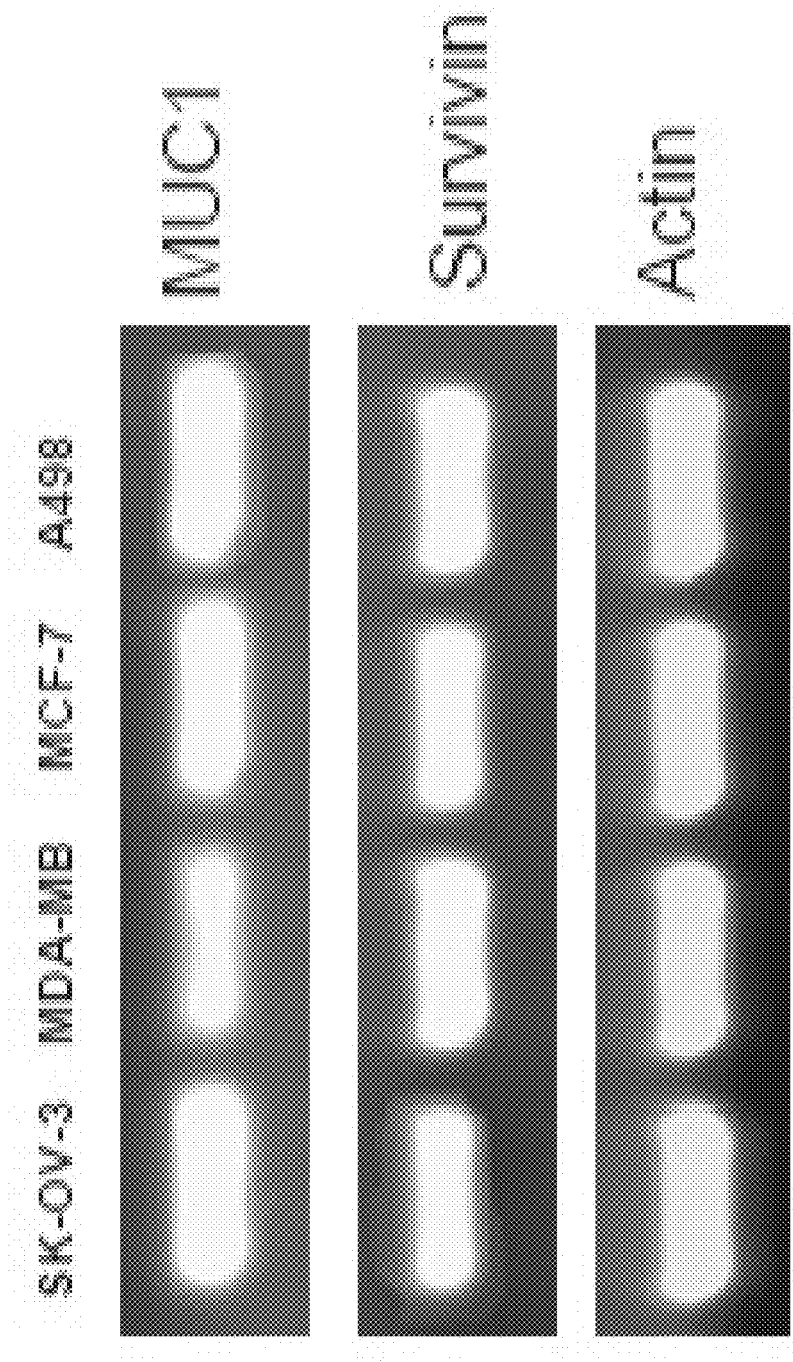
FIG. 13B is a photograph of an ethidium-bromide stained agarose gel showing the expression of intracellular survivin in these human tumor cell lines as determined by quantitative RT-PCR.

The cytolytic activity of the primed T cells to human tumor cells was further tested using a standard $^{51}$Cr release assay. By flow cytometric assays, it was shown that human breast (MDA-MD-231 and MCF-7), and renal (A498) tumor cells were HLA-A2+ and MUC1+ (FIG. 13A), while human ovarian (SK-OV-3) cancer cells were HLA-A2- and MUC1+ (FIG. 13A). The expression of intracellular survivin was detected in all of these human tumor cell lines by RT-PCR (FIG. 13B). To perform the $^{51}$Cr release assay, T cells from HLA-A2+ donors after two-week in vitro sensitization by transfected DCs were restimulated with MUC1 and survivin peptides-pulsed autologous DCs without Ad transfection, and then incubated with the target $^{51}$Cr-labeled human tumor cells at different ratios. FIG. 14 shows that HLA-A2+ T cells primed by Ad-siSSF-DCs had more potent cytolytic activity to HLA-A2+ and survivin/MUC1+ human tumor cells (MCF-7, MDA-MB-231 and A498) than those primed by Ad-SM-DCs. The specificity of cytolytic activities was demonstrated by the inability of the HLA-A2+ T cells primed by Ad-siSSF-DC to kill HLA2-survivin/MUC1+ SK-OV-3 cells and the inability of the HLA-A2+ T cells primed by Ad-GFP-DCs to kill these HLA2+, survivin/MUC1+ MDAMB-231, MCF-7 and A498 tumor cells. Taken together, these results demonstrate the powerful immunostimulatory potency of the vaccine compositions of the present invention to prime antigen specific antitumor CTL responses capable of selectively killing human tumor cells.

Example 7

Overcoming Treg-Mediated Suppression by Ad-siSSF-DC

Figure 15A:
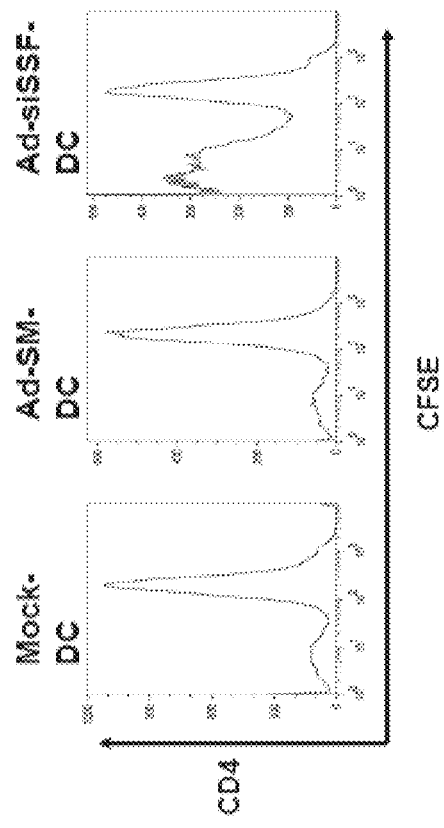
FIG. 15 is a series of charts and graphs showing the ability of Ad-siSSF-DCs to overcome CD4+CD25high Treg-mediated suppression. The proliferation rates of CFSE-labeled or non-labeled CD4+CD25– Teff cells in the presence of CD4+ CD25high Treg that had been co-cultured with Ad-transfected DCs in the presence of 0.5 µg/ml anti-human CD3 were examined by $^3$H thymidine incorporation (FIG. 15A) or CFSE dilution assay (FIG. 15B).
Figure 15B:
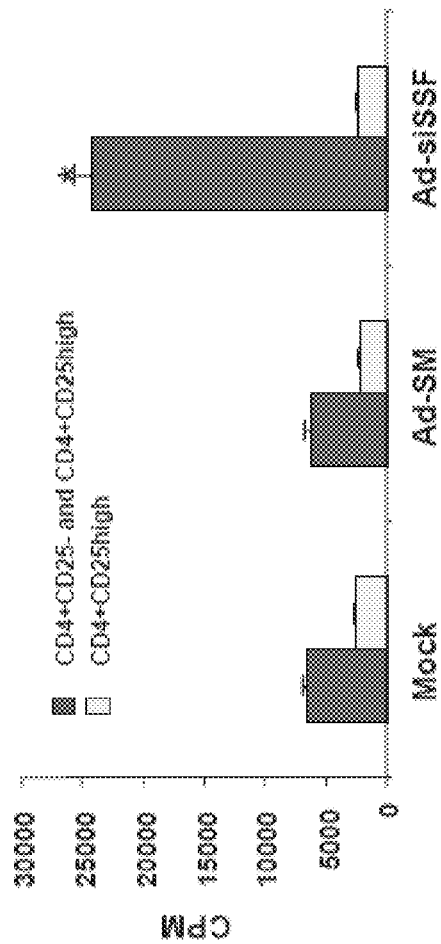

In this Example, an embodiment of the vaccine compositions of the present invention was examined for its effects on overcoming suppression by CD4+CD25+Foxp3+ T regulatory (Treg) cells. Treg cells play a suppressive role in limiting antitumor immunity in mice and humans (Sakaguchi, *Nat Immunol*, 6: 345-352, 2005). The proliferation and expansion of effector T cells can be suppressed by CD4+CD25+ Treg (Sakaguchi, *Nat Immunol*, 6: 345-352, 2005). In this study, it was found that GITRL and OX40L levels were significantly elevated on Ad-siSSF-DC (FIG. 6) and that higher levels of cytokines such as IL-6 and TNFα were produced by Ad-siSSF-DCs (FIGS. 8 and 9). These proinflammatory costimulatory molecules and cytokines were found to not only stimulate effector T cells, but also suppress the suppressive activity of Treg cells (Pasare et al., *Science*, 299: 1033-1036, 2003; Peluso et al., *J Immunol*, 178: 732-739, 2007). As such, according to the methods described in Example 1, it was tested whether the Ad-siSSF-transfected, hyperactivated DCs are able to override the suppressive activity of human CD4+CD25high Treg. Autologous CD4+CD25high Treg were sorted by FACS and then co-cultured with Ad-transfected DCs for 5 days. Both $^3$H thymidine incorporation and CFSE dilution assays showed that, after coculture with Ad-siSSF-DCs, CD4+CD25high Treg were no longer able to suppress the proliferation of CD4+CD25- effector T cells, while CD4+CD25high Treg after coculture with Ad-SM-DCs still efficiently suppressed the proliferation of CD4+CD25- effector T cells (FIG. 15), indicating the unique ability of Ad-siSSF-DCs to overcome Treg-mediated immune suppression.

Example 8

Adjuvants for Protective Immune Responses for Enhancing Levels of Proinflammatory Cytokines and Costimulatory Molecules in Mouse and Human DCs This example describes an adjuvant that includes a TLR5 ligand and an inhibitor of the regulator of cytokine receptor and TLR signaling, SOCS1. The adjuvant is drastically more potent and persistent than TLR agonists in stimulating the level and duration of inflammatory cytokine production by both murine and human dendritic cells and activating both cellular and humoral immune responses in vivo. Thus, this adjuvant has the unique capability of boosting more potent immune responses to a higher level that cannot be achieved by stimulation with TLR agonists or natural infections. Consequently, this adjuvant is useful in methods for protective immune responses against pathogens associated with chronic infections.

Figure 16:
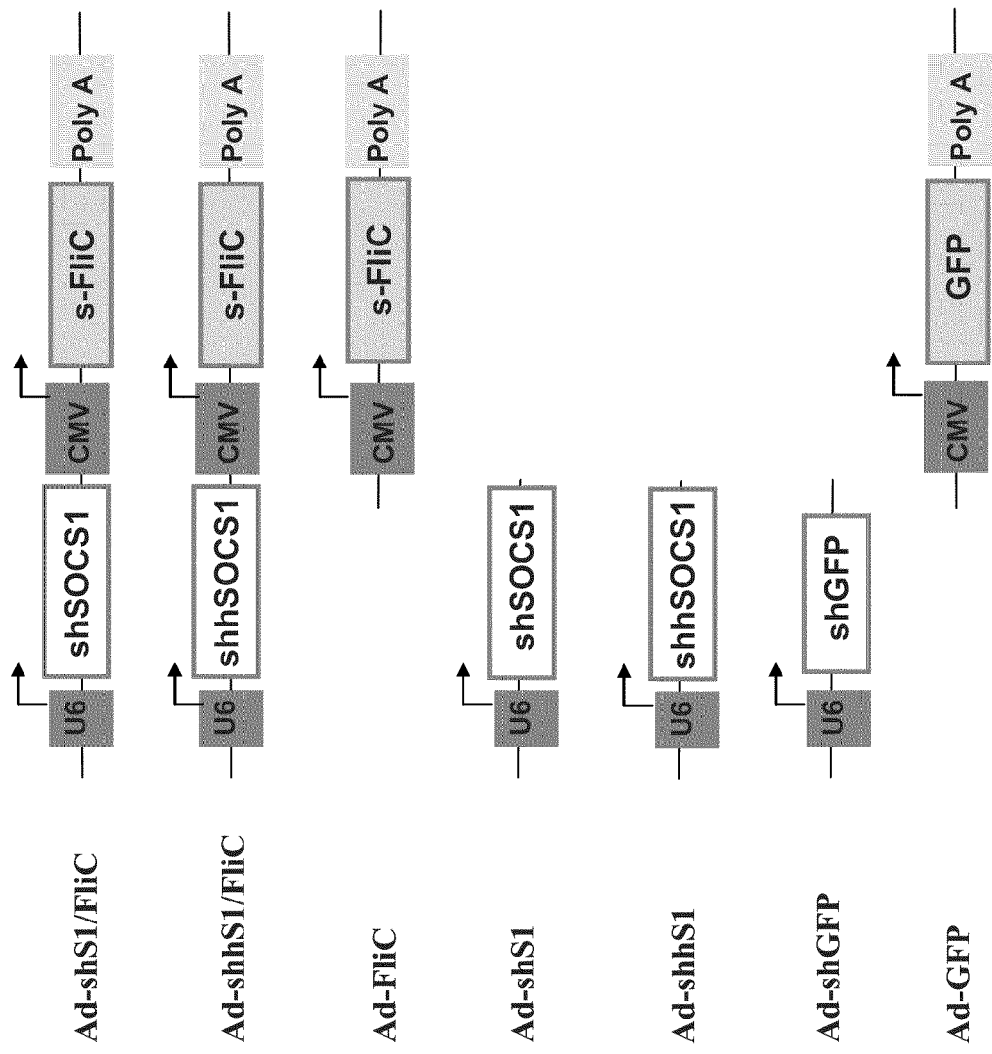
FIG. 16 is a schematic representation of recombinant Ad vectors.

A recombinant replication-deficient adenoviral vector coexpressing SOCS1-shRNA (shS1) and a modified secretory flagellin (FliC), a TLR5 ligand, designated as Ad-shS1/FliC, and a panel of recombinant Ad vectors expressing shS1, shGFP, or secretory FliC alone were constructed (FIG. 16). FliC stimulates antigen-specific cellular and humoral immune responses. An Ad-Easy system (E1 and E3 deletion; Quantum Biotechnologies Inc., Palo Alto, Calif.) was used to construct and generate the replication-defective adenoviruses. The flagellin (FliC) gene was amplified by PCR using *Salmonella enterica* serovar *Typhimurium* as a template as described in Example 1. The mouse shS1 CTACCTGAGTTCCTTCCCCTT (SEQ ID NO: 175) and human shS1 CACGCACTTCCGCACATTC (SEQ ID NO: 176) were inserted into the Ad vector, and the inserts of these resultant Ad vectors were confirmed by DNA sequencing.

Figure 17:
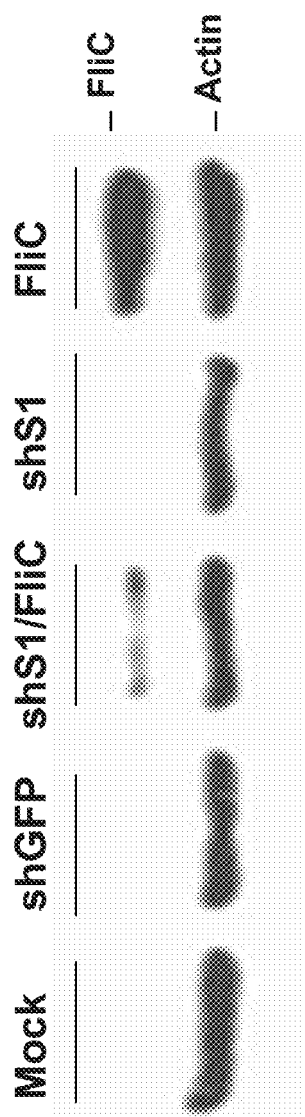
FIG. 17 is a western blot of FliC expression in murine BM-DCs transduced with indicated Ad vectors at an MOI of 250 ifu, stained with an anti-FliC antibody (Miravista Diagnostics, Indianapolis, Ind.).
Figure 18:
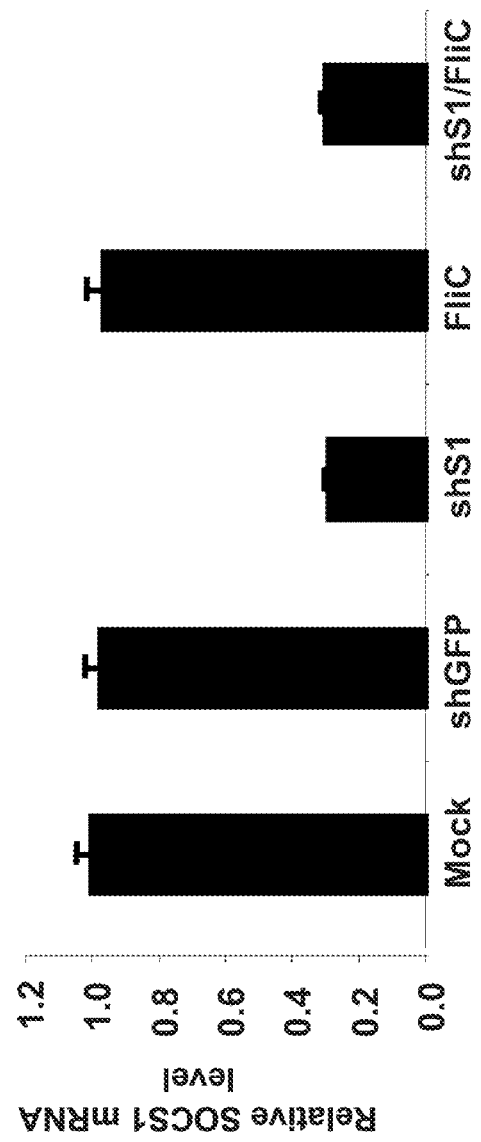
FIG. 18 is a graph showing quantitative RT-PCR analysis of SOCS1 mRNA levels in murine BM-DCs transduced with indicated Ad vectors at an MOI of 250 ifu.

Recombinant Ad vectors are known for high transduction efficiency of DCs. The ability to downregulate SOCS1 by Ad-shS1/FliC and Ad-shS1 was confirmed by qRT-PCR and Western blotting (FIG. 17). High levels of FliC proteins were produced by bone marrow (BM)-derived DCs transduced with Ad-shS1/FliC and Ad-FliC (FIG. 18).

Figure 19:
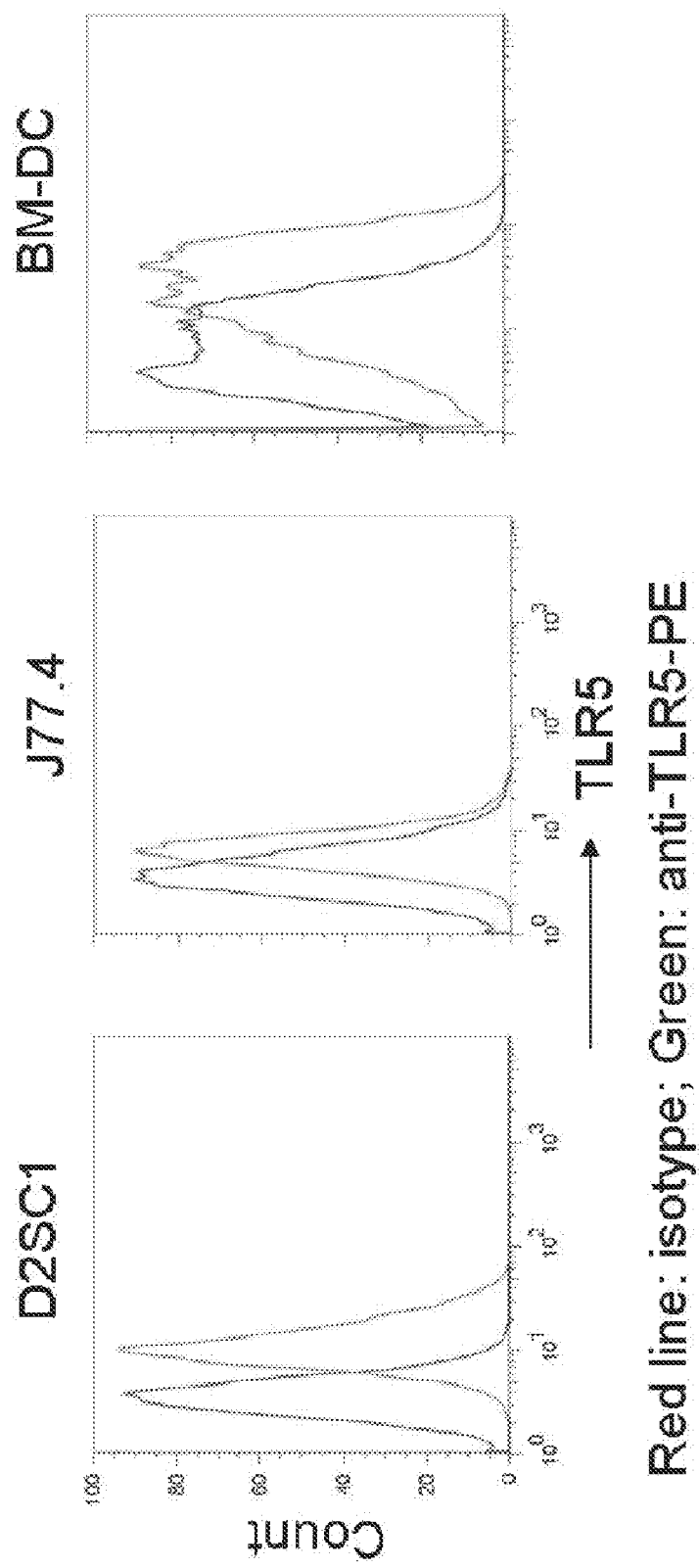
FIG. 19 is a series of graphs show flow cytometric analysis of surface TLR5 with an anti-TLR5-PE in D2SC1, J77.4 and BM-DC cells (IMG-663D, IMGENEX).
Figure 20A:
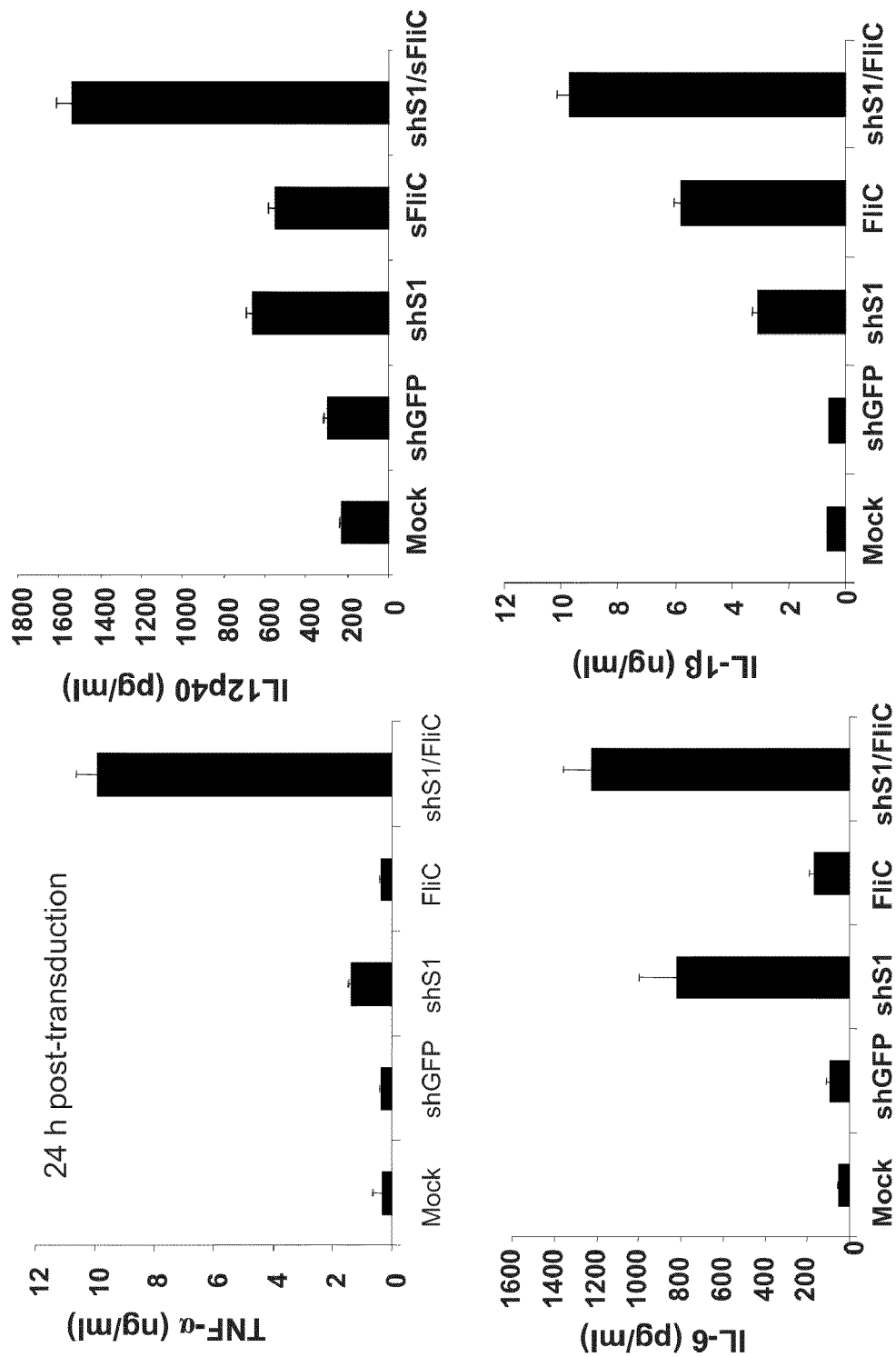
FIGS. 20A-20C, 20F, and 20G show charts of flow cytometry results of assays for representative cytokines after 24 h.
Figure 20B:
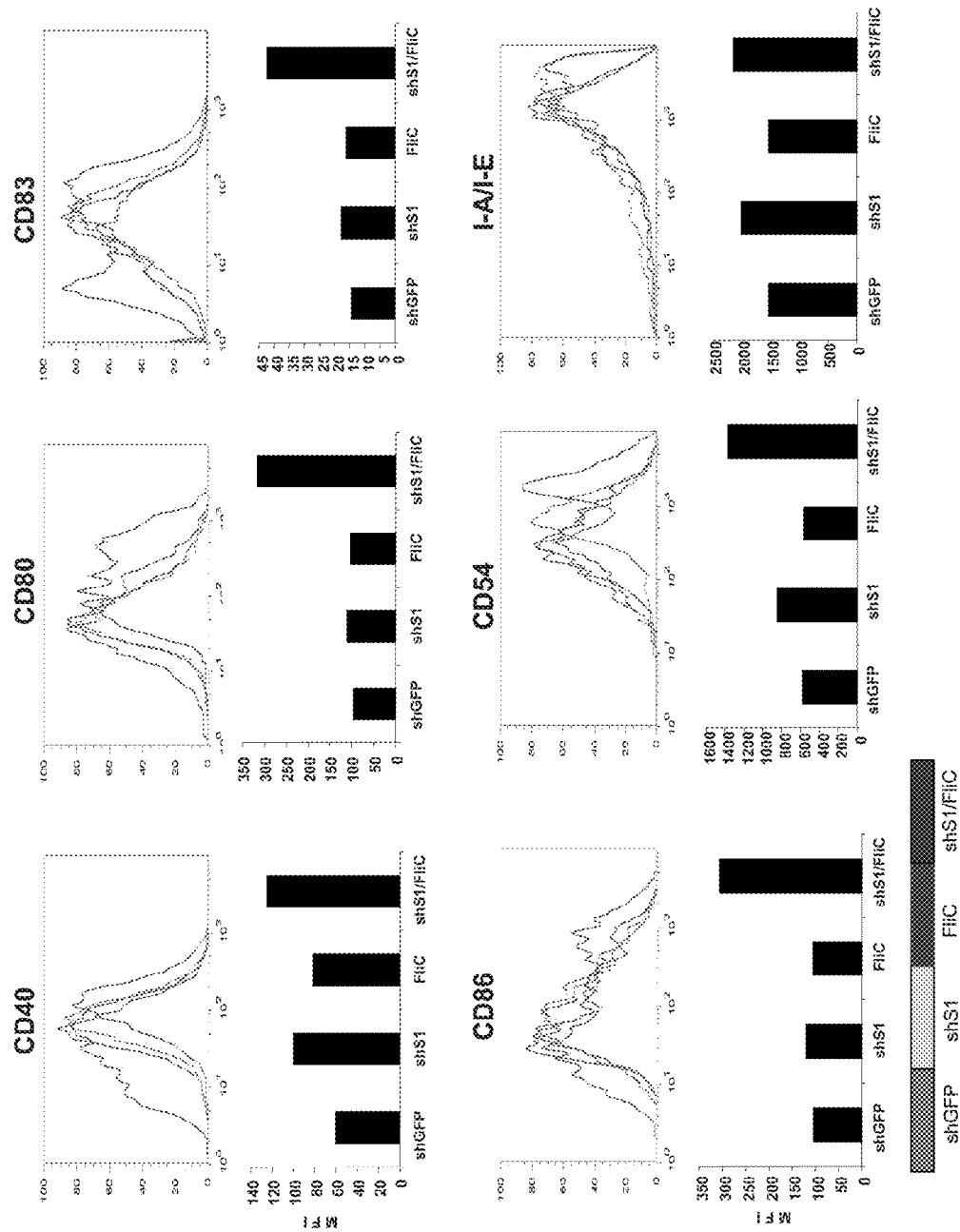

Next, it was tested whether Ad-shS1/FliC is more potent than Ad-shS1 and Ad-FliC in enhancing the levels of proinflammatory cytokines and costimulatory molecules expressed by DCs. Murine BM-DCs, J774A.1 macrophages, and D2SC/1 DCs that express surface TLR5 (FIG. 19) were used for this study. We found that higher levels of proinflammatory cytokines such as IL-12, IL-6 and TNF-α were produced by Ad-shS1/FliC-transduced BM-DCs compared to those by Ad-shS1 or Ad-FliC-BM-DCs (FIG. 20A). Higher levels of surface costimulatory molecules were also observed on Ad-shS1/FliC-BM-DCs (FIG. 20B). Similar results were obtained in Ad-transduced J774A.1 macrophages and D2SC/1 DCs, indicating a marked synergistic effect of SOCS1 silencing and TLR stimulation.

Figure 20C:
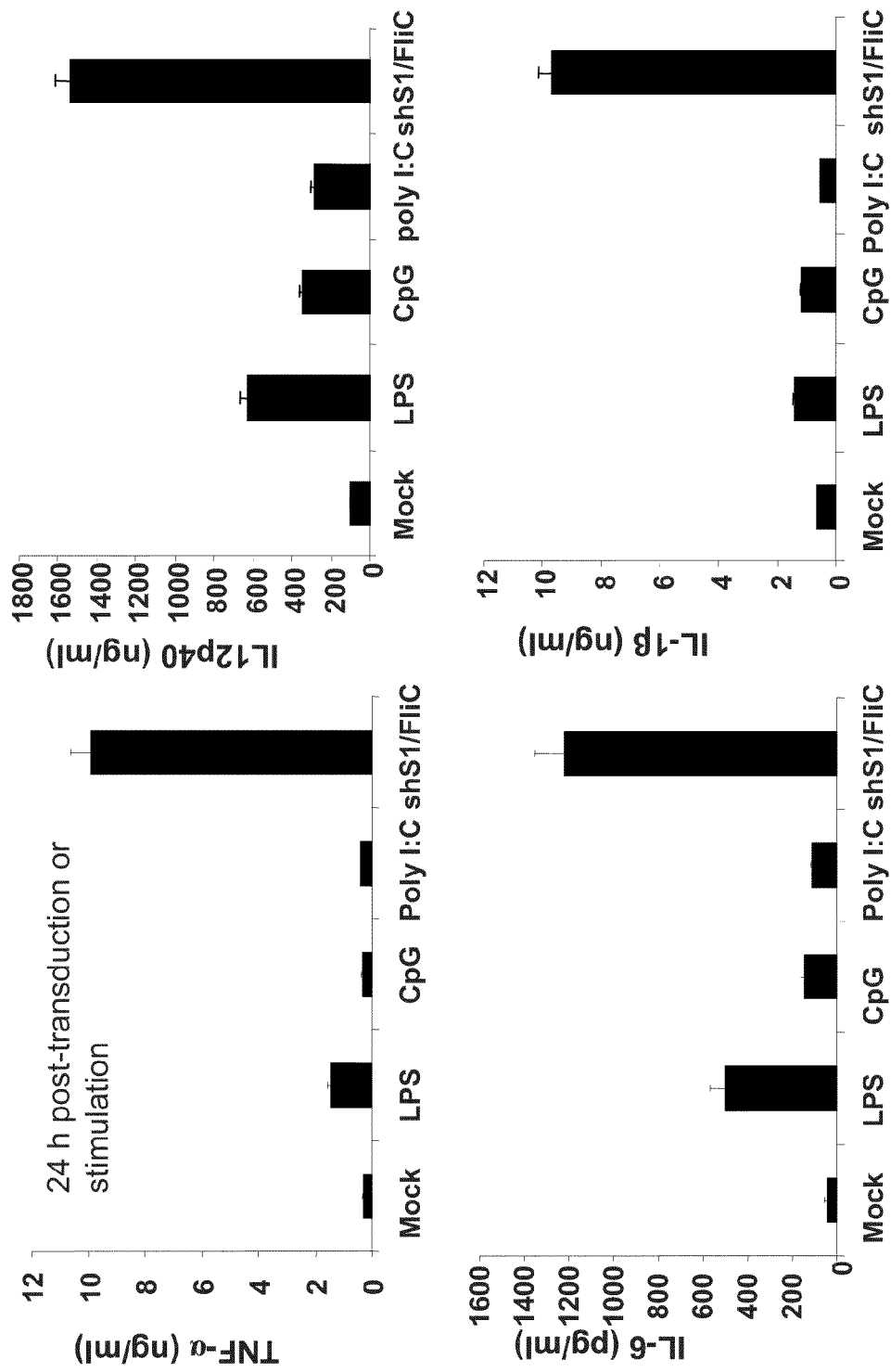

Numerous TLR agonists, such as imiquimod, polyI:C, and CpG, have been developed for use as adjuvants. It was examined whether Ad-shS1/FliC is more potent than commonly used TLR agonists in enhancing the expression levels of proinflammatory cytokines and costimulatory molecules produced by DCs. FIG. 20C shows that Ad-shS1/FliC was more potent than commonly used TLR agonists (LPS, PolyI:C, CpG, and Imiquimod) in stimulating the expression of proinflammatory cytokines and costimulatory molecules (data not shown), indicating the superior stimulatory potency of Ad-shS1/FliC.

Figure 20D:
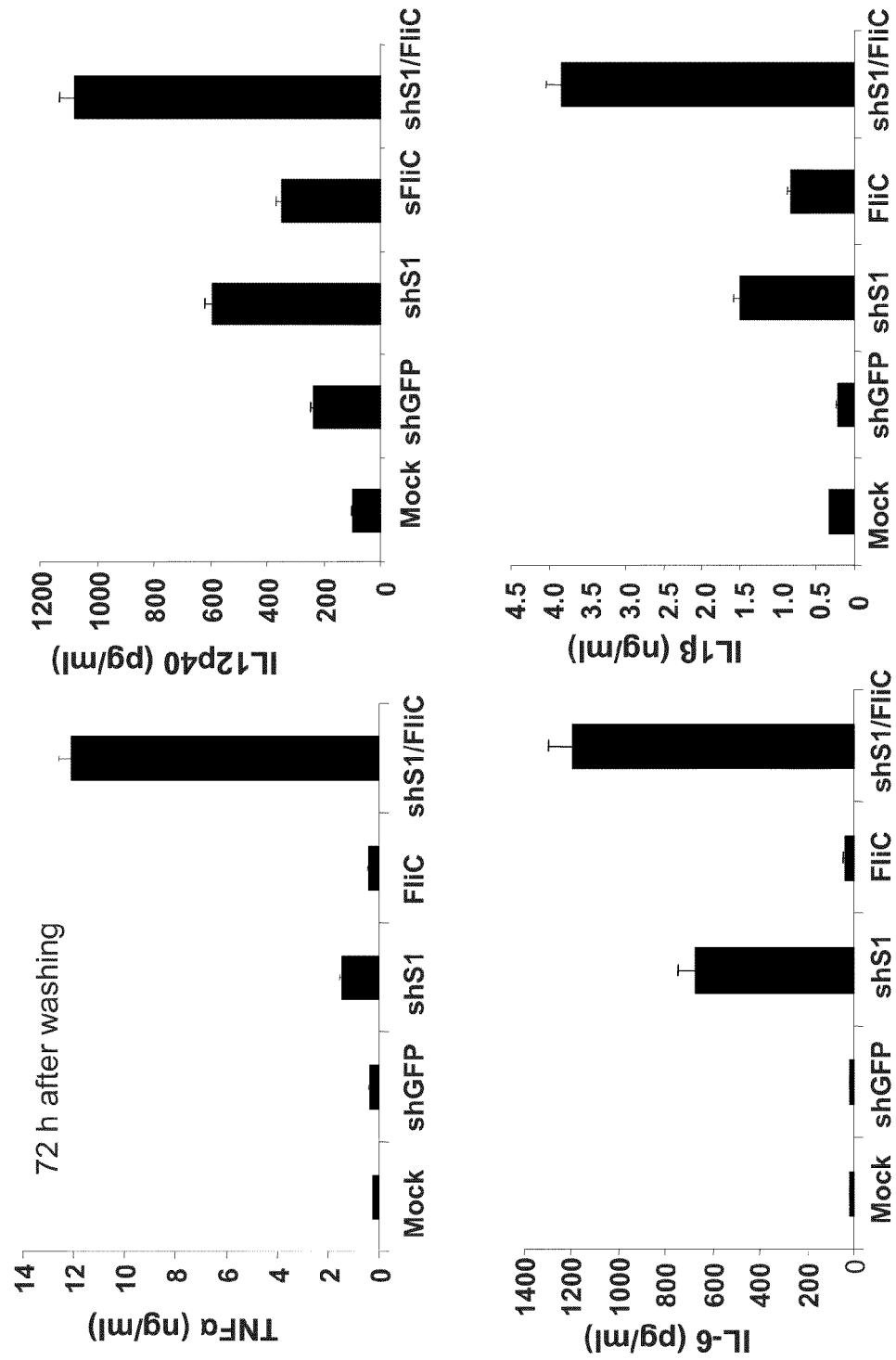
FIGS. 20D, 20E, 20H, and 20I show charts of flow cytometry results of assays for representative cytokines after the cultures were washed and replaced with fresh medium that does not contain stimuli for 24 h. Data are representative of three repeated experiments.
Figure 20E:
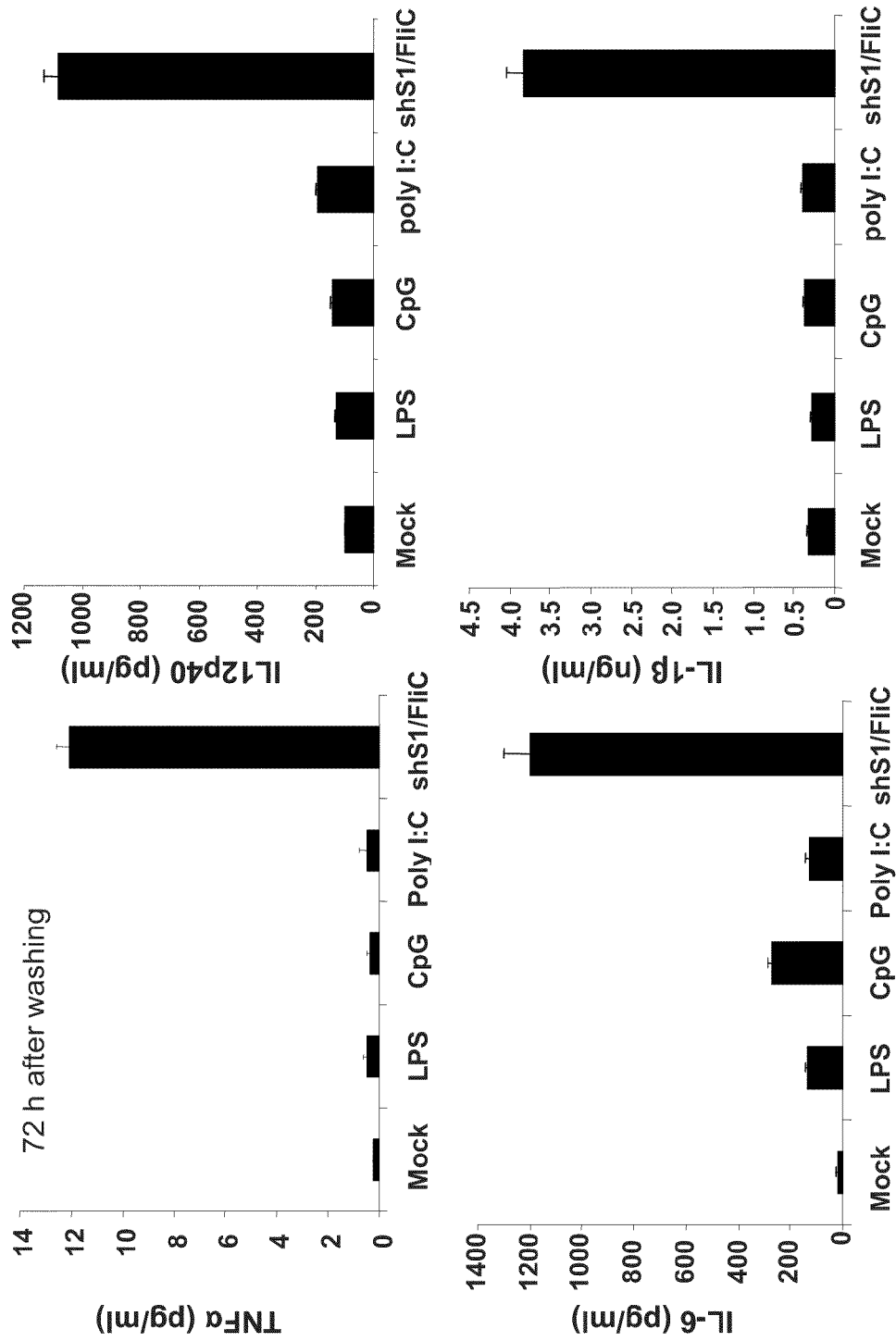

Since the duration and intensity of antigen presentation is important in determining the magnitude and memory of adaptive immune responses, the duration of inflammatory cytokine production by DCs treated with different stimuli was compared. BM-DCs were transduced with different Ad vectors or stimulated with TLR agonists for 24 hr, then washed and replaced with fresh culture medium that does not contain stimuli. The cytokine concentrations in culture medium were examined before and after washing. FIG. 20D shows that Ad-shS1/FliC-DCs still produced high levels of inflammatory cytokines after washing. In contrast, TLR agonist-DCs were unable to actively produce cytokines after washing. It was also examined whether Ad-shS1/FliC uniquely triggers and sustains TLR signaling cascades in DCs by comparing the kinetics of inflammatory signaling in Ad-transduced or TLR agonist-stimulated DCs. Western blotting analyses show the prolonged phosphorylation of key intracellular proinflammatory signaling molecules, such as pIκBα and pSTAT4 (data not shown). Collectively, these data indicate that Ad-shS1/FliC possesses a unique ability to stimulate the prolonged and enhanced production of proinflammatory cytokines by DCs.

Figure 20F:
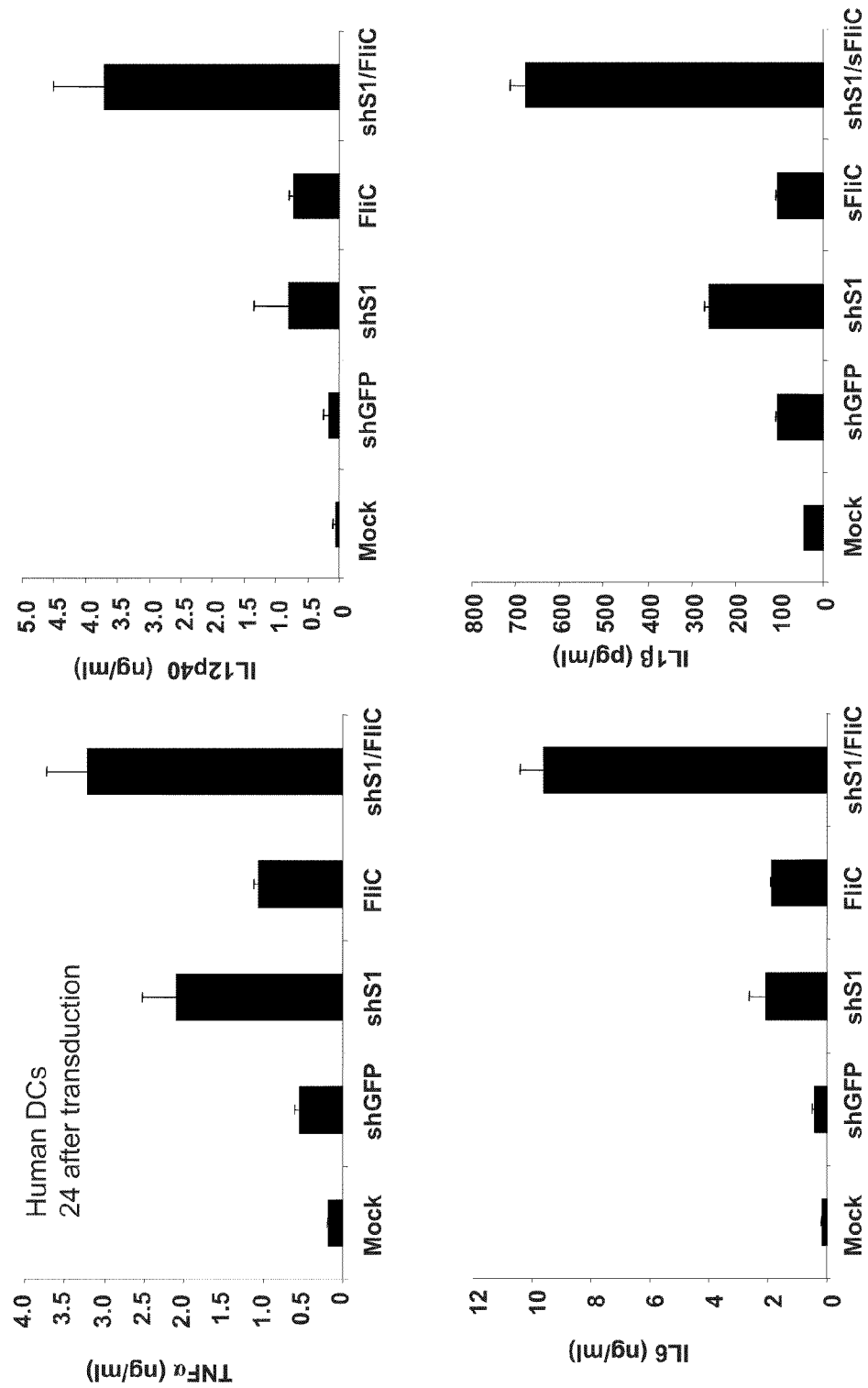
Figure 20G:
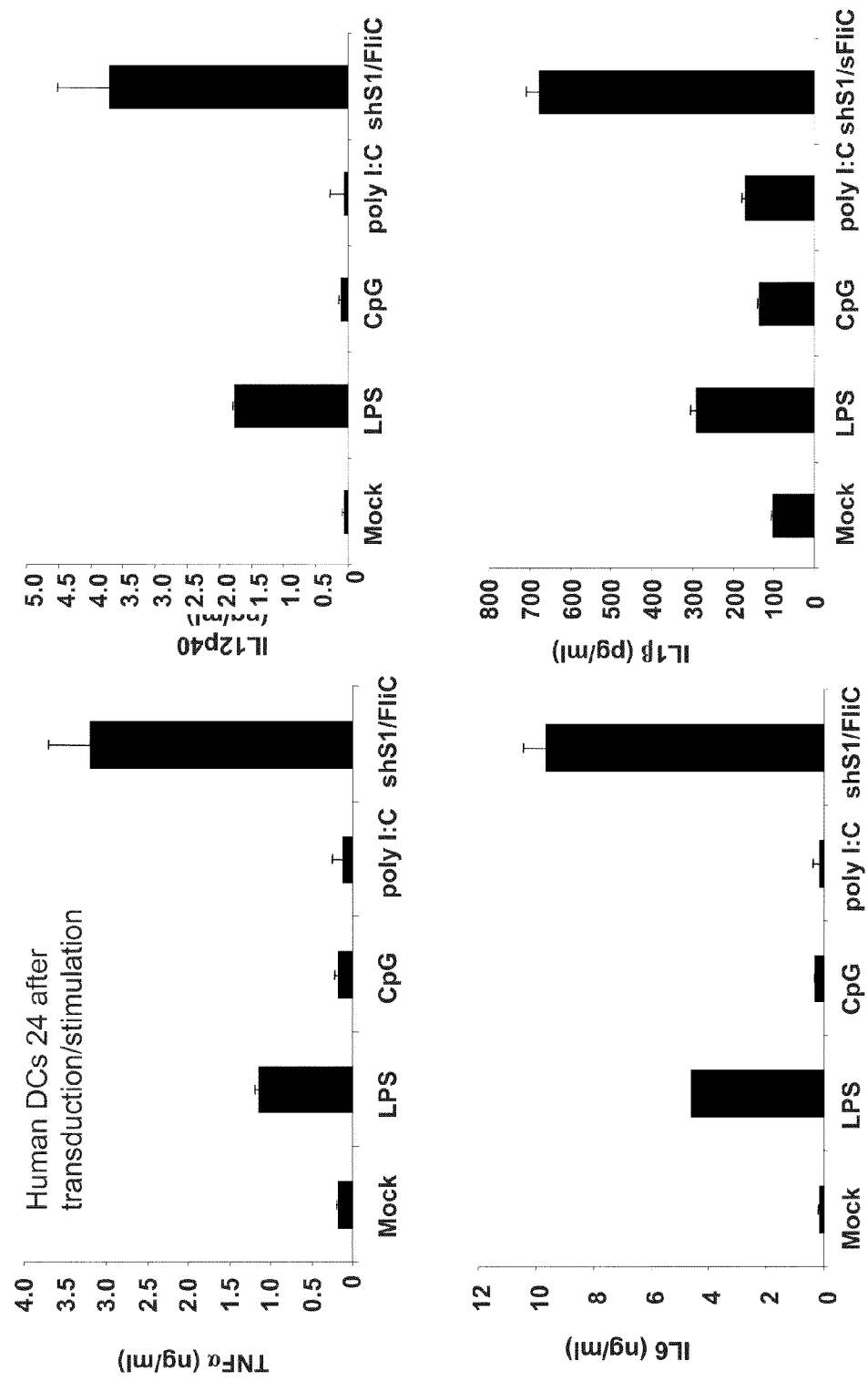
Figure 20H:
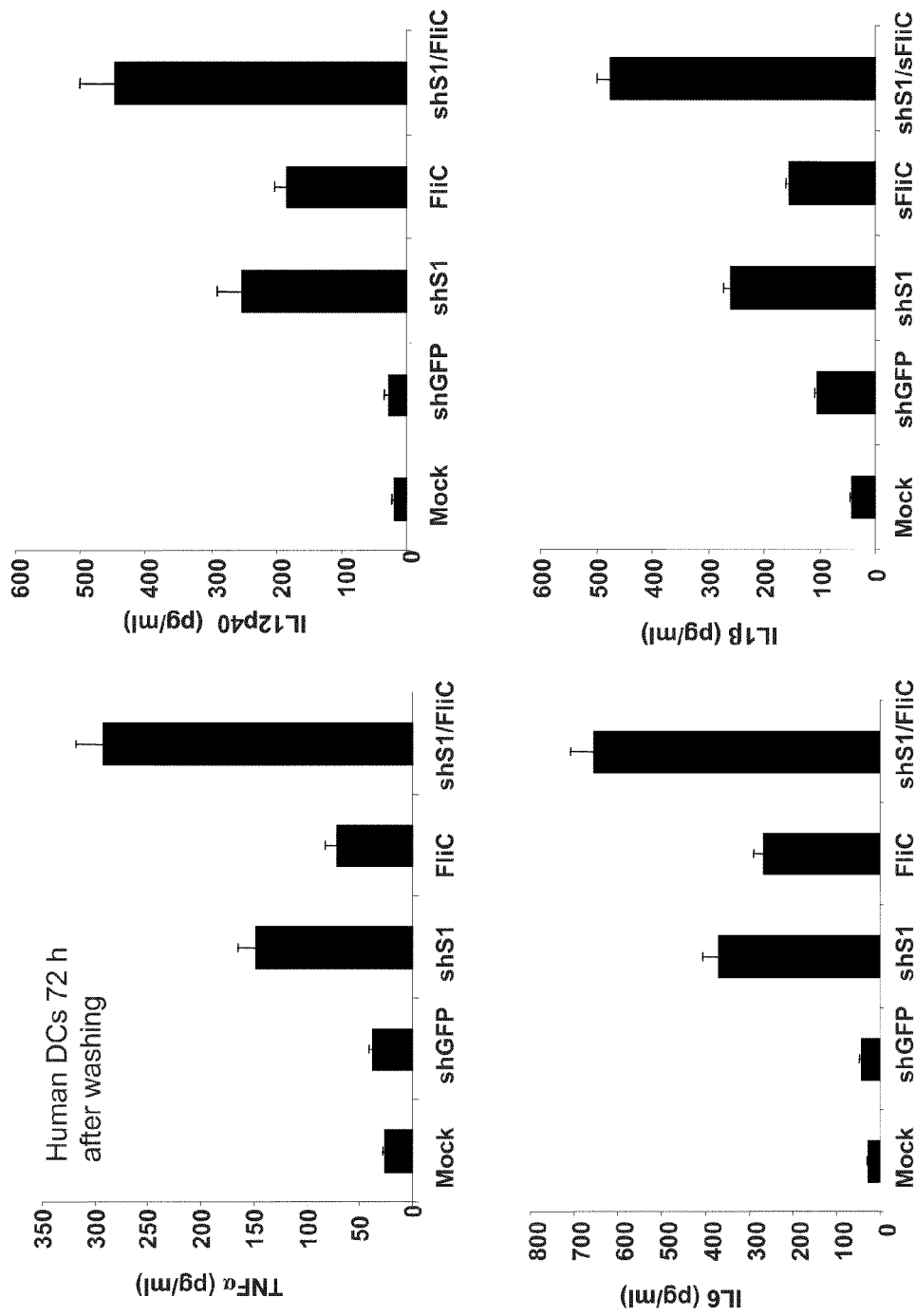
Figure 20I:
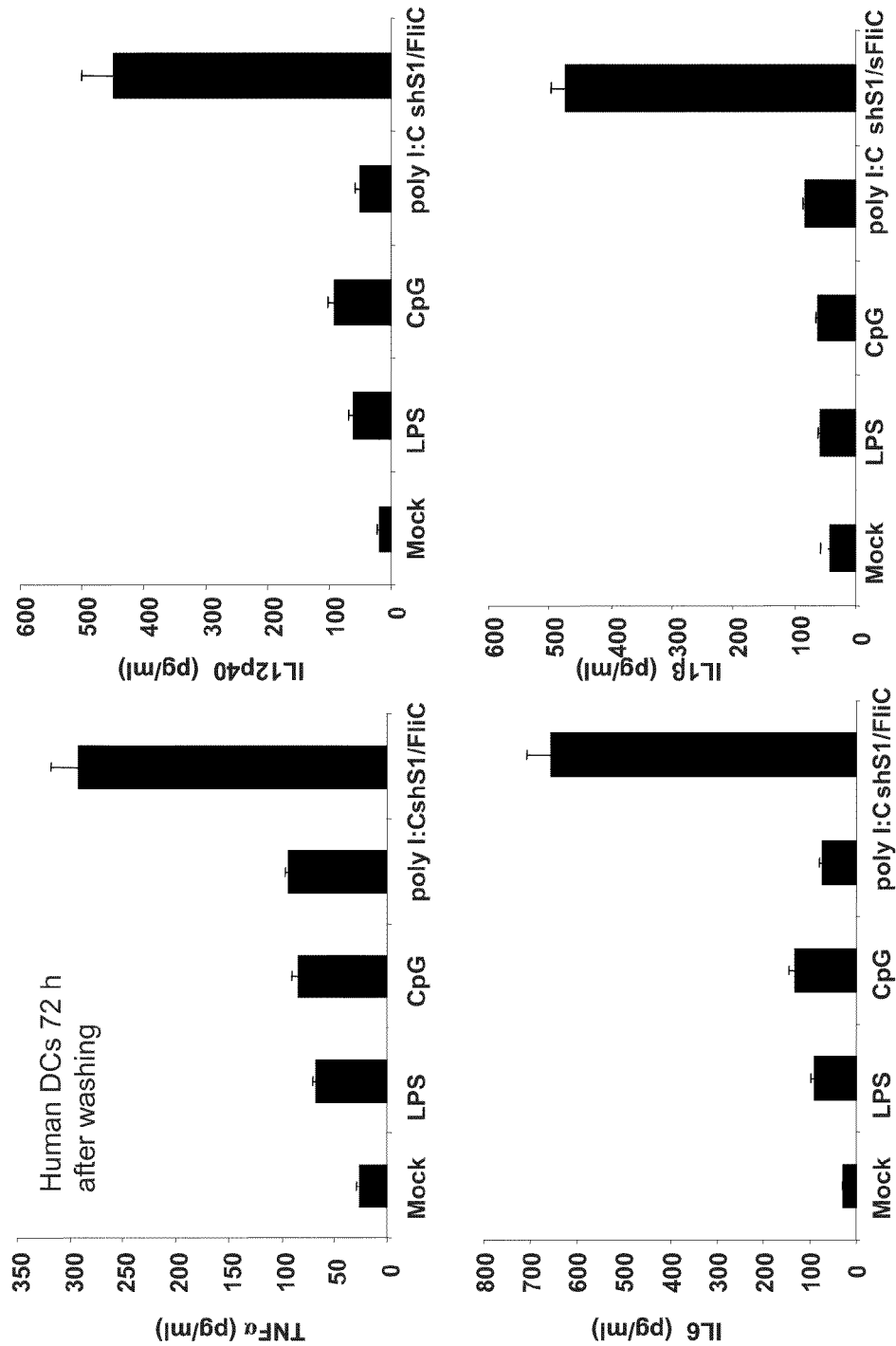

To assess the translational potential of this adjuvant, it was tested whether Ad-shS1/FliC is also potent in stimulating human DCs. Due to the heterogeneity of mouse and human SOCS1 sequences, we generated a recombinant vector Ad-shhS1/FliC that coexpresses FliC and a human (h) shS1-shRNA capable of efficiently silencing human SOCS1 mRNA (>80% reduction). FIG. 20F shows that human DCs transduced with Ad-shhS1/FliC produced higher levels of proinflammatory cytokines than human DCs transduced with Ad-shhS1 or Ad-FliC. It was observed that human DCs transduced with Ad-shhS1/FliC produced significantly higher levels of cytokines than DCs stimulated with commonly used TLR agonists (FIG. 20G). Furthermore, the duration of inflammatory cytokine production was significantly prolonged in human DCs transduced with Ad-shhS1/FliC compared to human DCs transduced with Ad-shhS1 or Ad-FliC, or stimulated with TLR agonists (FIGS. 20H & 20I). These results indicate that SOCS1 also plays a critical role in human DCs and that combined FliC stimulation and human SOCS1 silencing more potently and persistently stimulates human DCs than commonly used TLR agonists. Accordingly, compositions comprising a siRNA inhibitor of a SOCS and a flagellin polypeptide are useful as vaccine adjuvants for enhancing an immune response.

Example 9

Ad-shS1/FliC Adjuvants for Protective Immune Responses for Enhancing Potency of DC Vaccines In Vivo The ability of Ad-shS1/FliC to enhance the potency of DC vaccines was assessed in vivo. Groups of wild-type mice were immunized (footpads) with BM-DCs that are transduced with Ad vectors or stimulated with LPS, the most potent of TLR agonists, and pulsed with a model antigen ovalbumin (OVA) or a representative viral antigen (HCV E2) two times at a weekly interval. Murine BM-DCs were transduced with an equal amount of recombinant Ad vectors at an MOI of 250 ifu or stimulated with LPS (100 ng/ml), respectively, for 24 hr and then pulsed with recombinant HCV-E2 protein (20 μg/ml) for additional 6 hr. Groups of C57BL/6 mice (6 mice/group) were immunized with the transduced or LPS-stimulated DCs ($1 \times 10^6$ cells per mouse) twice at a weekly interval via footpads.

FIGS. 21A-21D show that Ad-shS1/FliC-DCs were significantly more potent than DCs transduced with Ad-shS10 or Ad-FliC, or stimulated with TLR agonists, in inducing OVA-specific (data not shown) and HCV E2-specific CD8+ CTL and CD4+ Th responses, as demonstrated by IFNγ intracellular cytokine staining and ELISPOT assays, were indicative of the superior potency of Ad-shS1/FliC-DCs in activating both anti-HCV CD8+ CTL and CD4+ Th responses.

Figure 21A:
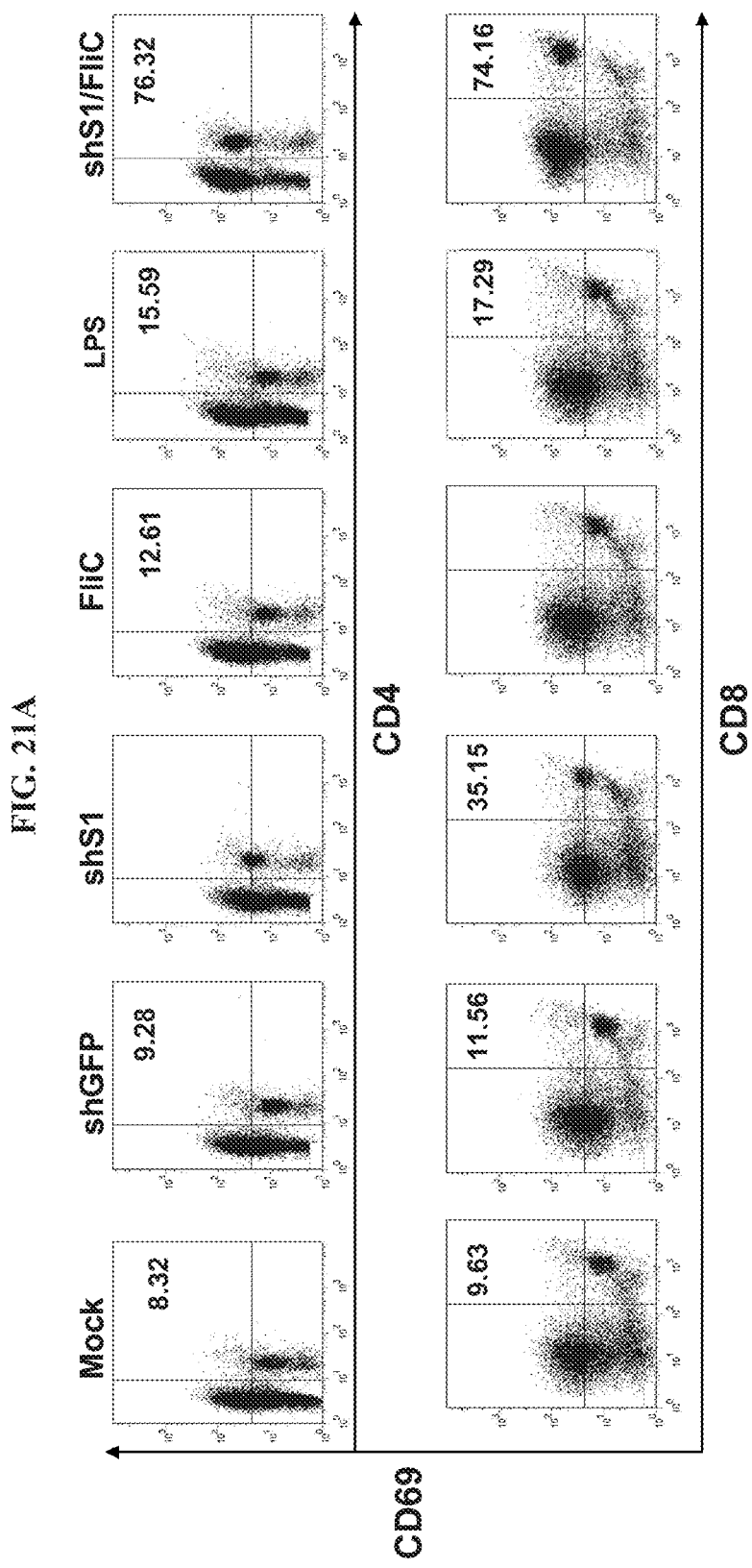
FIG. 21 is a series of charts showing the potency of anti-HCV E2 T cell and antibody responses induced by Ad-shS1/FliC-DCs. Mice were sacrificed for surface marker staining (FIG. 21A), intracellular cytokine staining (FIG. 21B), ELISPOT (FIG. 21C) and ELISA (FIG. 21D) assays.
FIG. 21E is a chart of HCV-E2-specific antibody titers in mice immunized with Ad-shS1/FliC-DCs.
FIG. 21F is a chart showing the level of IgG AFC progenitors in mice immunized with Ad-shS1/FliC-DCs and controls.
Figure 21B:
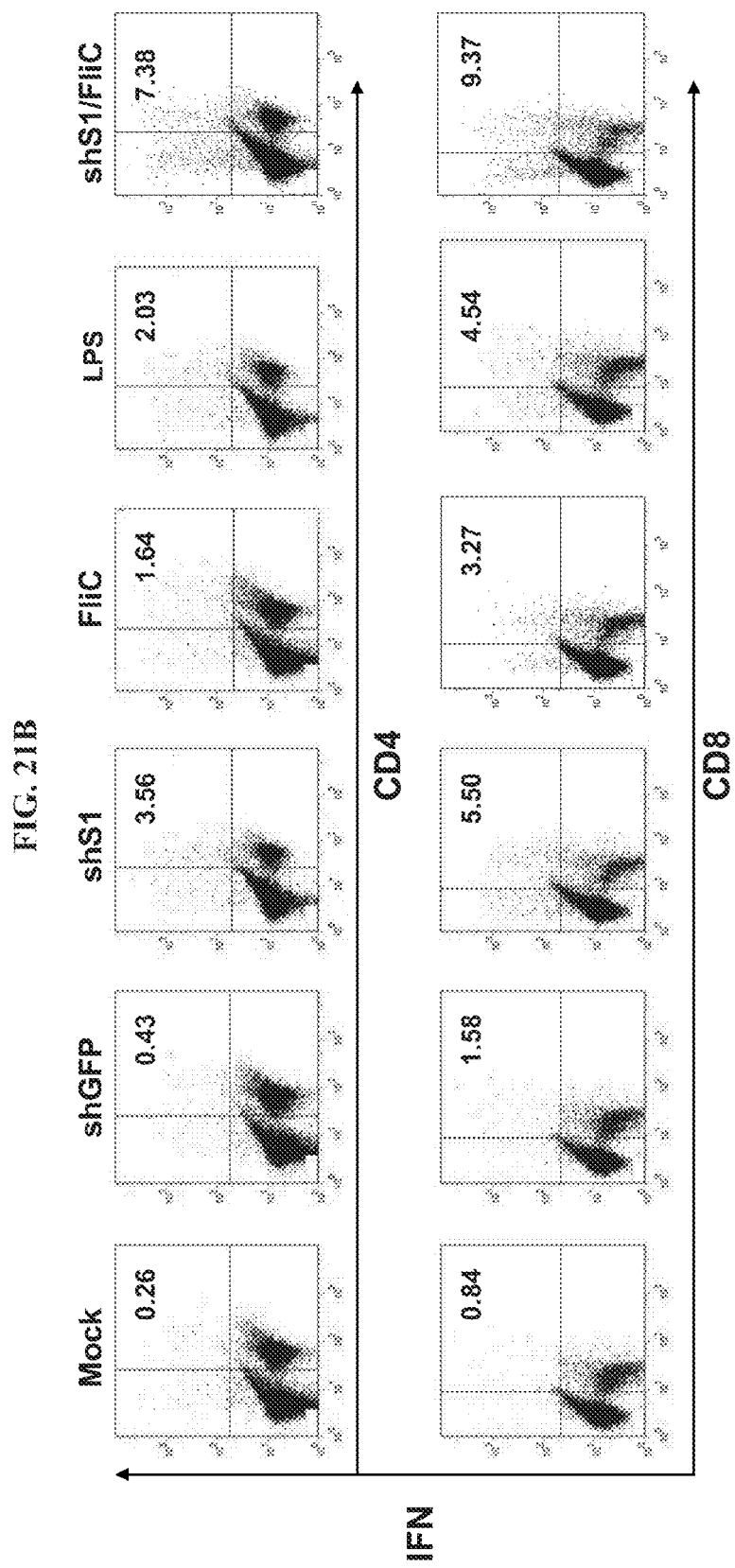
Figure 21E:
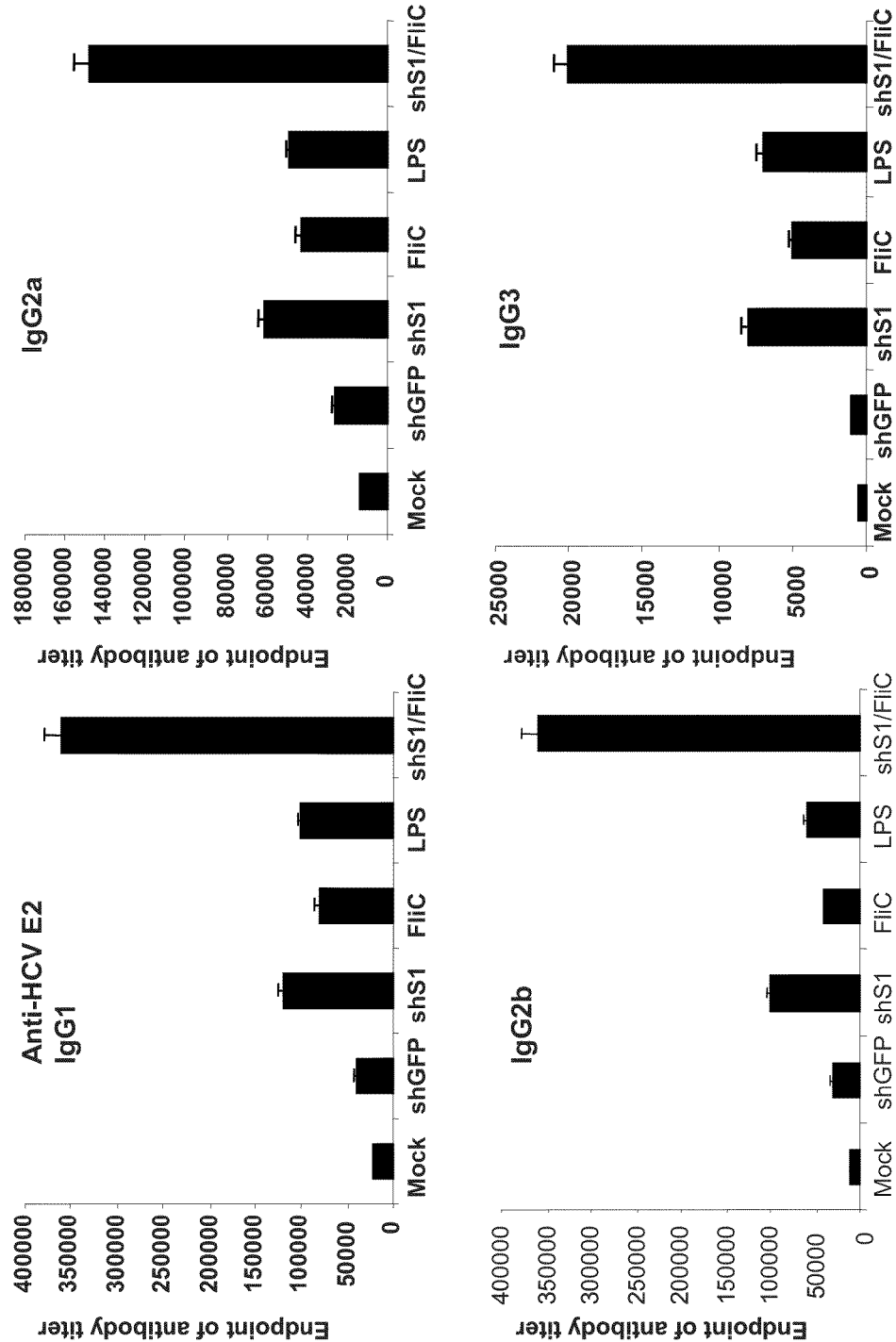

The stimulatory effect of Ad-shS1/FliC on the potency of DCs to induce anti-HCV antibody responses was also investigated. FIG. 21E shows an increase in overall HCV-E2-specific antibody titers in mice immunized with Ad-shS1/FliC-DCs, compared with the corresponding IgG subclasses in mice immunized with DCs transduced with Ad-shS1 or Ad-FliC or stimulated with TLR agonists. The HCV E2-specific antibody subclass profile showed a Th1-polarized IgG response, higher IgG2a, a subclass associated with a Th1 response, induced by Ad-shS1/FliC-DCs.

Figure 21F:
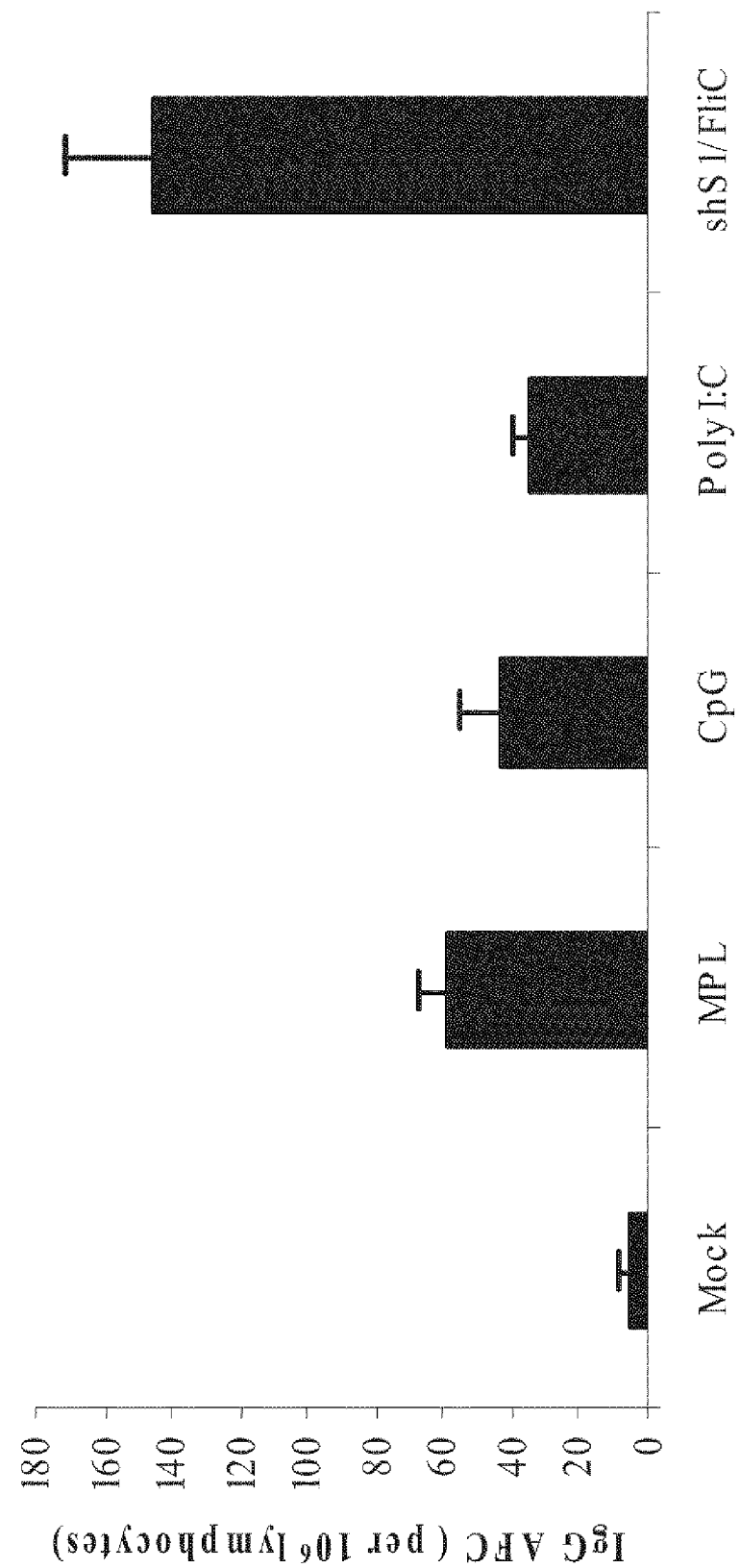

To directly test the enhanced ability of Ad-shS1/FliC-DCs to activate B cells, a B cell Elispot assay was used to examine the frequencies of anti-HCV E2 IgG-producing B cells in the immunized mice. FIG. 21F shows that frequencies of anti-HCV E2 IgG-producing B cells were significantly higher in Ad-shS1/FliC-DC mice than in mice immunized with DCs transduced with Ad-shS1 or Ad-FliC or stimulated with TLR agonists (P<0.01). Thus, these results demonstrate that Ad-shS1/FliC-DCs also more effectively activate HCV E2-specific B cells to produce higher titers of neutralizing antibodies.

Example 10

Figure 22:
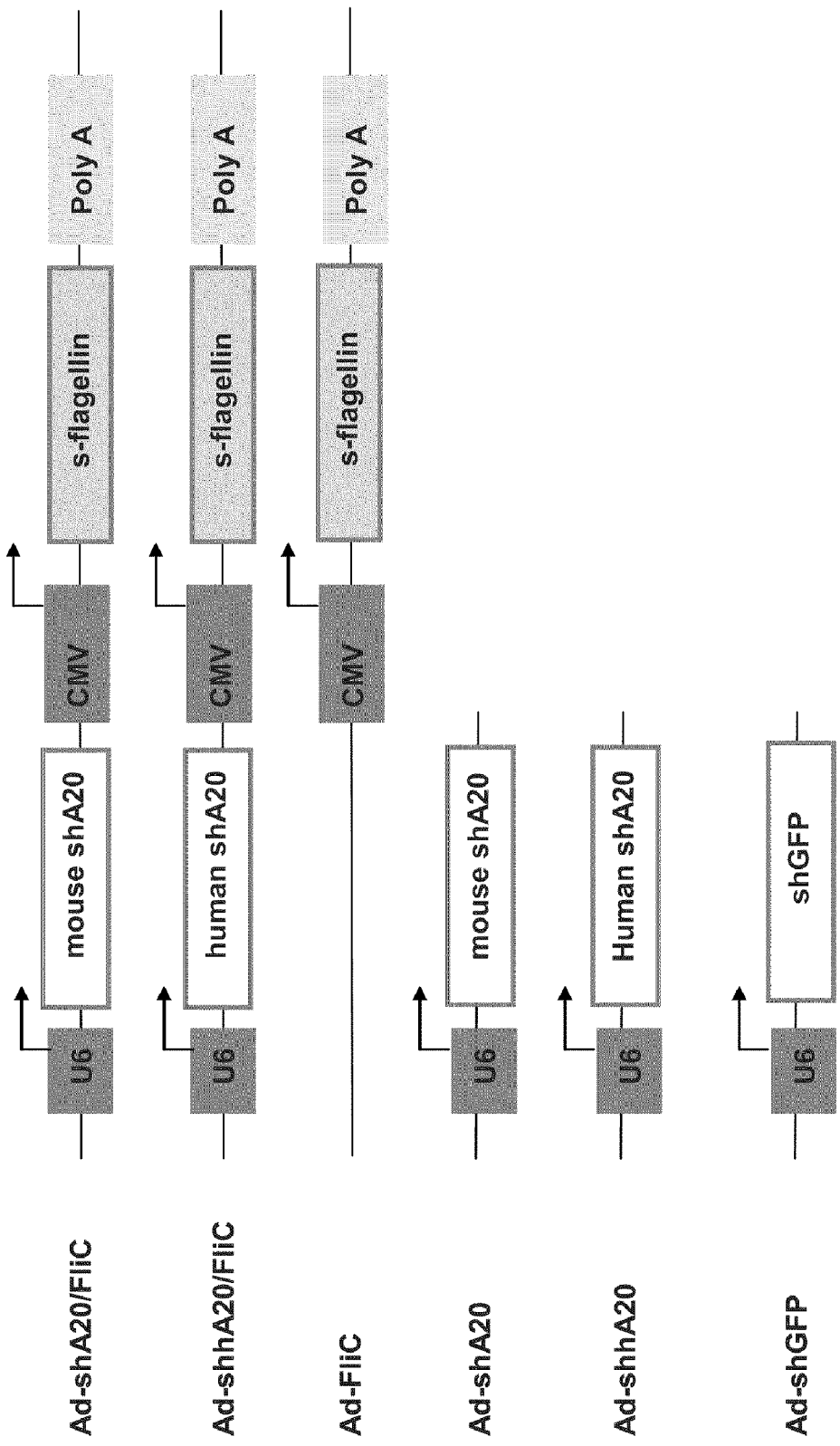
FIG. 22 is a schematic representation of recombinant Ad vectors.

Ad-shA20/FliC Adjuvants for Protective Immune Responses for Enhancing Potency of DC Vaccines In Vivo An AdEasy system (E1 and E3 deletion; Quantum Biotechnologies Inc., Palo Alto, Calif.) was used to construct and generate replication-defective adenoviruses. The modified flagellin (fliC) gene with a signal leader sequence from human tyrosinase was amplified by PCR as described above. pSuper vectors containing the mouse shA20 sequence (CAAAGCACTTATTGACAGA (SEQ ID NO: 177)) and the human (h) shA20 sequence (CCATGCACCGATACACACT (SEQ ID NO: 178)) were constructed. The shuttle vectors Ad-shA20/FliC and Ad-shhA20/FliC were constructed by inserting SpeI-digested U6-shA20 or U6-shhA20 from pSuper-shA20 or pSuper-shhA20 vectors into a SpeI-digested Ad-FliC vector. The recombinant replication-deficient viruses Ad-shA20/FliC and Ad-shhA20/FliC coexpressing the mouse A20 shRNA or human A20 shRNA under U6 RNA promoter and flagellin under control of the CMV promoter were generated and produced according to the manufacturer's instructions (Quantum Biotechnologies Inc., Palo Alto, Calif.). A schematic diagram of these recombinant adenoviral vectors is represented in FIG. 22. The expression of secretory FliC proteins and downregulation of A20 by shA20 were demonstrated in BM-DCs transduced with Ad-shA20/FliC and Ad-shhA20/FliC by Western blotting analysis and qRT-PCR.

First, it was tested in vitro whether Ad-shA20/FliC that coexpresses shA20 and secretory FliC is superior to Ad-shA20 that expresses shA20 only and Ad-FliC expresses secretory FliC only in stimulating DCs. It was found that Ad-shA20/FliC-transduced BM-DCs produced higher levels of proinflammatory cytokines than Ad-shA20 or Ad-FliC-transduced BM-DCs. Moreover, shA20/FliC-transduced BM-DCs produced higher levels of proinflammatory cytokines than DCs stimulated with TLR agonists such as PolyI:C and CpG.

Figure 23B:
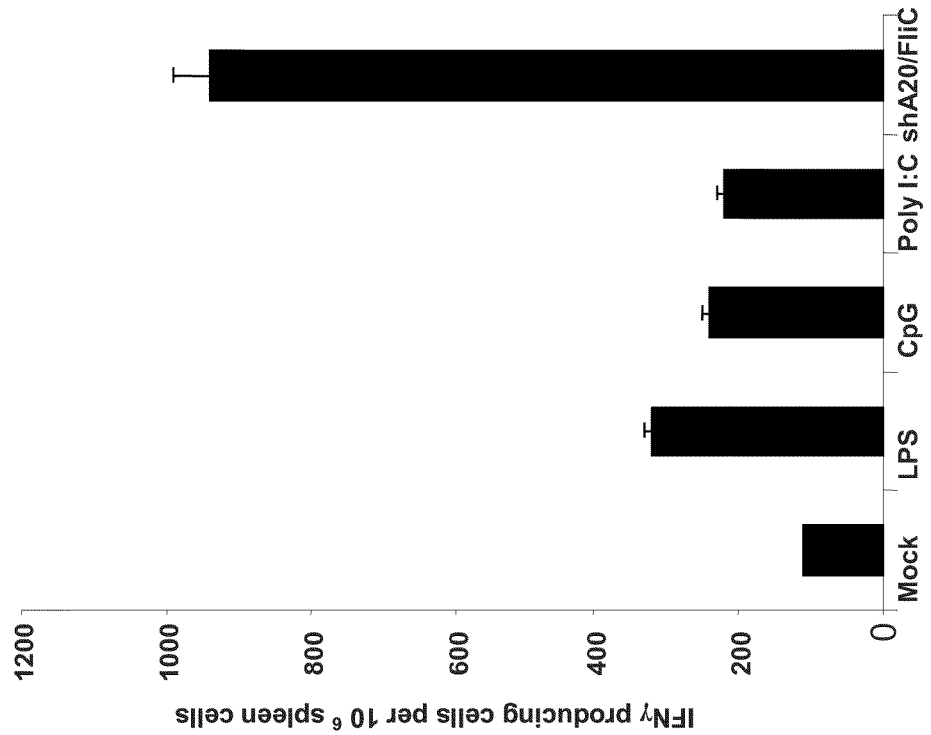
FIG. 23B shows the results of IFNγ ELISPOT assays after groups of C57BL/6 mice (4 per group) were immunized with HBsAg protein (50 μg/ml)-pulsed BM-DCs transduced with Ad vectors at a MOI of 250 ifu ($1\times10^6$ cells/mouse) or stimulated with commonly used TLR agonists via footpads twice at a weekly interval.
Figure 23A:
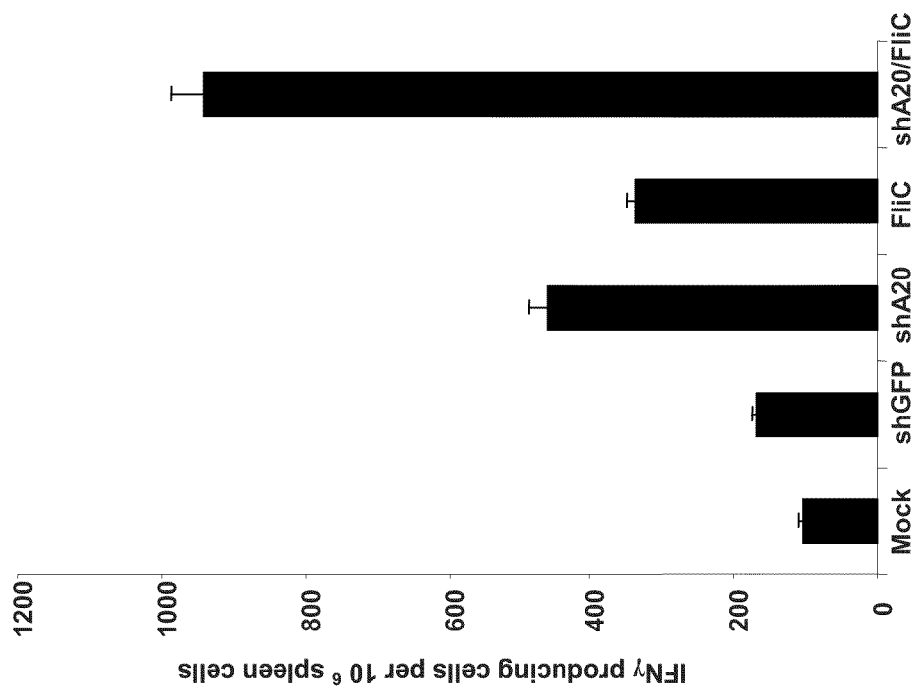
FIG. 23A shows the results of IFNγ ELISPOT assays after groups of C57BL/6 mice (4 per group) were immunized with HBsAg protein (Meridian Life Science, Inc., 50 μg/ml)-pulsed BM-DCs transduced with Ad vectors at a MOI of 250 ifu ($1\times10^6$ cells/mouse) via footpads twice at a weekly interval.
Figure 23D:
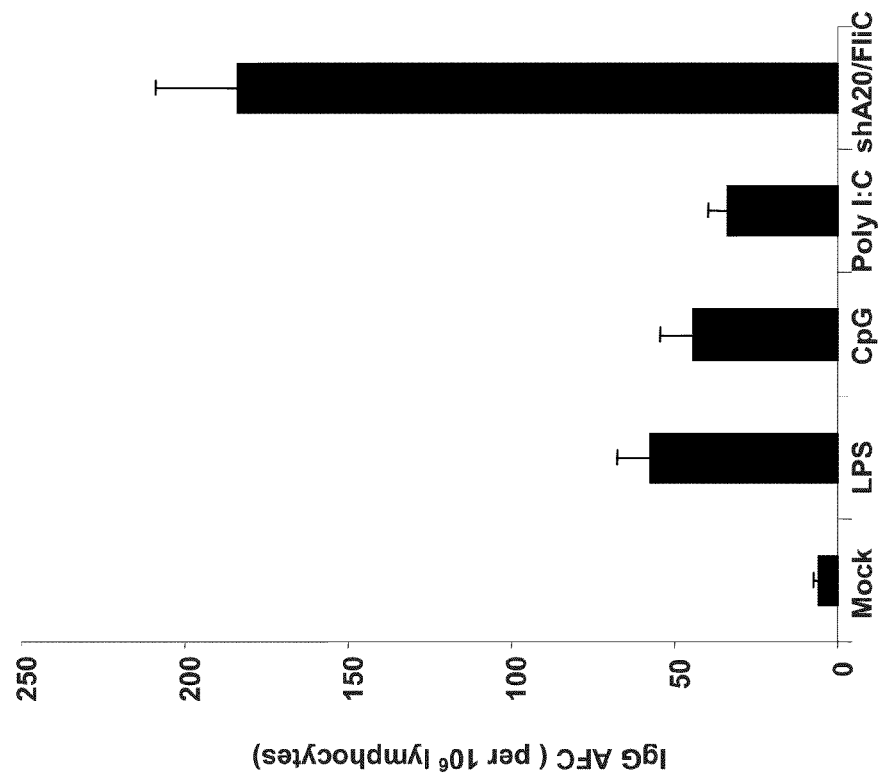
FIG. 23D shows the quantity of HBsAg-specific IgG secreting cells from pooled splenocytes obtained from groups of C57BL/6 mice immunized with HBsAg protein (50 μg/ml)-pulsed BM-DCs transduced with Ad vectors at a MOI of 250 ifu ($1\times10^6$ cells/mouse) or stimulated with commonly used TLR agonists.
Figure 23C:
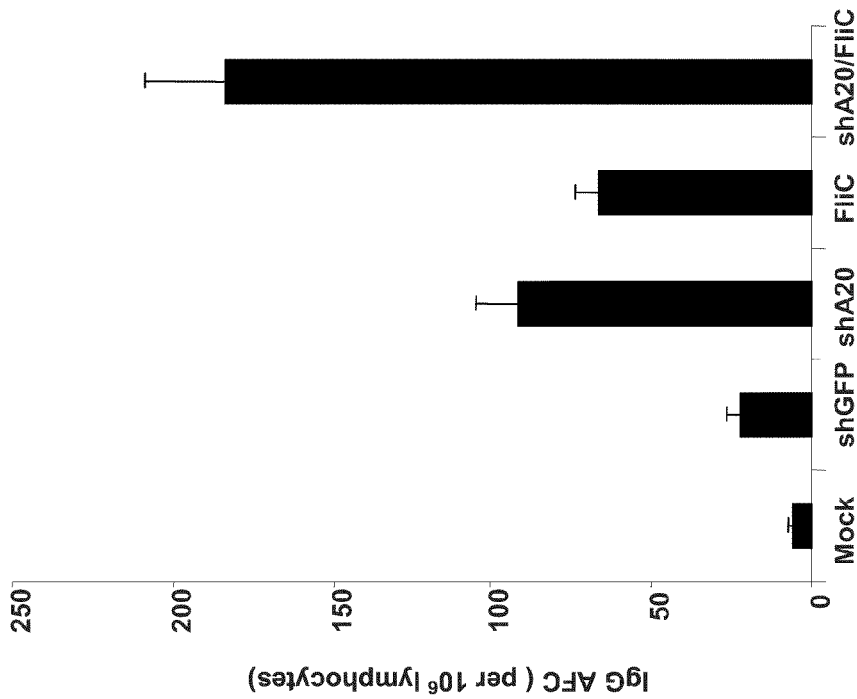
FIG. 23C shows the quantity of HBsAg-specific IgG secreting cells from pooled splenocytes obtained from groups of C57BL/6 mice immunized with HBsAg protein (50 μg/ml)-pulsed BM-DCs transduced with Ad vectors at a MOI of 250 ifu ($1\times10^6$ cells/mouse).

Next, it was tested n vivo whether Ad-shA20/FliC that coexpresses shA20 and secretory FliC is superior to Ad-shA20 and Ad-FliC in stimulating antigen-specific T and B cell responses by DC vaccines. It was found that HBsAg-pulsed, Ad-shA20/FliC-transduced BM-DCs induced much stronger HbsAg-specific T cell and B cell responses than HBsAg-pulsed, Ad-shA20 or Ad-FliC-transduced BM-DCs (FIG. 23A and FIG. 23C). Furthermore, HBsAg-pulsed, Ad-shA20/FliC-transduced BM-DCs induced much stronger HbsAg-specific T cell and B cell responses than HBsAg-pulsed BM-DCs stimulated with TLR agonists such as LPS, PolyI:C and CpG (FIG. 23 B and FIG. 23D).

In summary, the results shown in Examples 9 and 10 support the notion that the combined inhibition of TLR and downstream cytokine signaling and TLR stimulation may break the natural negative feedback barrier to trigger and sustain proinflammatory signaling cascades/loops in APCs. Persistent and enhanced inflammatory signaling will endow APCs to possess the unique ability to persistently activate innate and adaptive immunity Indeed, the prototype adjuvanst generated from this concept, Ad-siS1/FliC and Ad-siA20/FliC are more potent than commonly used TLR agonists in stimulating the levels of proinflammatory cytokines produced by murine and human DCs. Importantly, this adjuvant uniquely stimulates the production of inflammatory cytokines by DCs in a sustained manner. We further found that DCs stimulated with this adjuvant have drastically enhanced potency in inducing both cellular and humoral immune responses against antigens of pathogens associated with chronic infections. This novel adjuvant significantly boosts the magnitude and duration of both cellular and humoral immune responses to higher levels that cannot be achieved by stimulation with TLR agonists or natural infections, which can be used to develop more effectively prophylactic and therapeutic vaccines against infectious diseases. As such, compositions comprising a siRNA inhibitor of a negative immune regulator and a flagellin are useful in methods to enhance the immune response in mammals.

Example 11

FliC-Protamine Fusion Protein/siRNA Complexes as Vaccine Adjuvants

Figure 24:
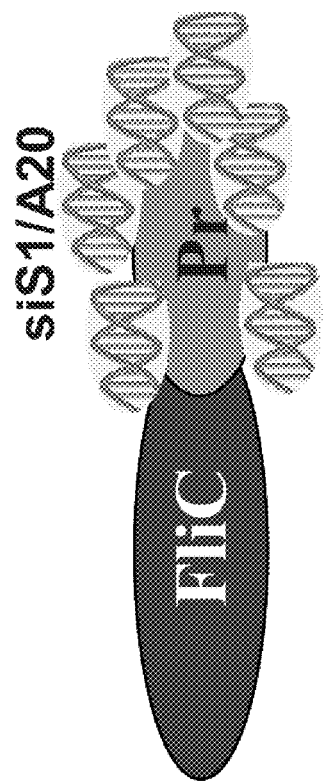
FIG. 24 is a schematic representation of FliC-protamine fusion protein/siRNA complexes for use as vaccine adjuvants.

Although Ad-siRNA/FliC vectors can be used as adjuvants for ex vivo therapeutic DC vaccines, the immunogenicity of Ad vectors may limit their efficacy and utility as in vivo adjuvants. Autologous DC vaccines prepared from individual patients would likely not be used for the treatment of chronic infections, due to the technical difficulty and costs associated with these treatments. A main obstacle to developing siRNA-based therapeutics is delivering it in vivo across the cell membrane to the cytoplasm for mediating mRNA degradation. Accordingly, this example describes a FliC-protamine fusion protein/siRNA complex for use as a vaccine adjuvant (FIG. 24).

In an earlier study, a recombinant bifunctional fusion protein was generated for the delivery of nucleic acids. This fusion protein consisted of an antibody anti-HIV Fab F105 (against gp120, the envelope glycoprotein of HIV-1) and a DNA binding moiety, protamine, that nucleates DNA in sperm, as a targeted gene carrier. See Chen et al. *Gene Ther* 2, 116-23 (1995). Nucleic acids (negative charge) statically interact with the protamine proteins (positive charge) to form soluble protein-nucleic acid complexes without the need of covalent coupling. These complexes can be specifically transferred into targeted HIV-1-infected cells by receptor-mediated endocytosis. Recently, it was found that siRNA oligos (negative charge) can efficiently bind to the anti-HIV F105 Fab-protamine fusion protein for effective delivery into targeted HIV-infected cells. Song et al. *Nat Biotech* 23, 709-717 (2005). An anti-ErbB2-protamine fusion protein was also shown to efficiently deliver siRNAs specifically to ErbB2-expressing breast cancer cells. In a recent collaborative study with a former fellow, anti-HBsAg single chain antibody and protamine fusion proteins were found to efficiently carry siRNA-expressing plasmids into HBsAg-positive cells to inhibit HBV gene expression and replication. Wei-Hong et al., *Hepatology* 46, 84-94 (2007). In addition, Peer et al. *PNAS* 104, 4095-4100 (2007) demonstrated that antibody-protamine fusion proteins targeting LFA-1 efficiently delivered siRNAs and specifically induced silencing in primary monocytes and DCs. Moreover, they used protamine-condensed siRNA in anti-integrin beta nanoparticles to systemically deliver siRNA into leukocytes. Taken together, these studies demonstrate the feasibility of using protamine fusion proteins as carriers for targeted delivery of siRNA.

A baculoviral expression system (Novagen) was used to produce a recombinant FliC-Protamine fusion protein. The FliC gene was fused in-frame with human protamine gene (aa 1-51) that was PCR-amplified using the plasmid pCMV-Fab105-Protamine vector previously constructed as a template by overlapping PCR (See Table 6).

TABLE 6

Sequence of FliC-Protamine Fusion Protein (SEQ ID NO: 174)
MAQVINTNSLSLLTQNNLNKSQSALGTAIERLSSGLRINSAKDDAAG

QAIANRFTANIKGLTQASRNANDGISIAQTTEGALNEINNNLQRVRE

TABLE 6-continued

Sequence of FliC-Protamine Fusion Protein

LAVQSANSTNSQSDLDSIQAEITQRLNEIDRVSGQTQFNGVKVLAQD

NTLTIQVGANDGETIDIDLKQINSQTLGLDTLNVQQKYKVSDTAATV

TGYADTTIALDNSTFKASATGLGGTDQKIDGDLKFDDTTGKYYAKVT

VTGGTGKDGYYEVSVDKTNGEVTLAGGATSPLTGGLPATATEDVKNV

QVANADLTEAKAALTAAGVTGTASVVKMSYTDNNGKTIDGGLAVKVG

DDYYSATQNKDGSISINTTKYTADDGTSKTALNKLGGADGKTEVVSI

GGKTYAASKAEGHNFKAQPDLAEAAATTTENPLQKIDAALAQVDTLR

SDLGAVQNRFNSAITNLGNTVNNLTSARSRIEDSDYATEVSNMSRAQ

ILQQAGTSVLAQANQVPQNVLSLLRMARYRCCRSQSRSRYYRQRQRS

RRRRRRSCQTRRRAMRCCRPGFSSISAHHHHHHHH

Figure 25:
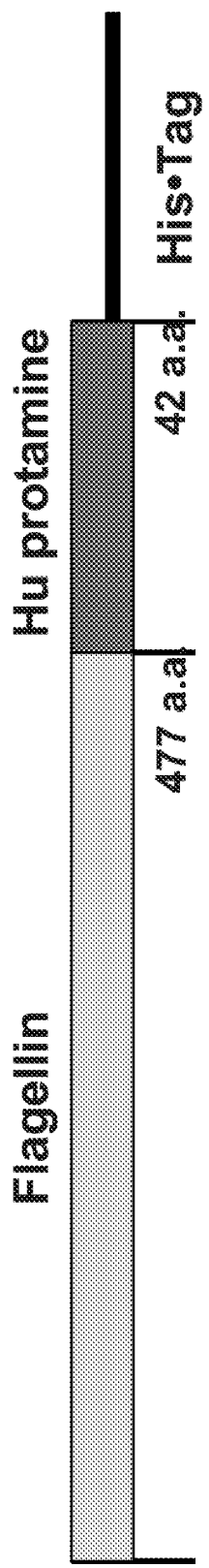
FIG. 25 is a schematic representation of a baculoviral expression vector for the expression of recombinant FliC-Protamine fusion proteins.
Figure 26:
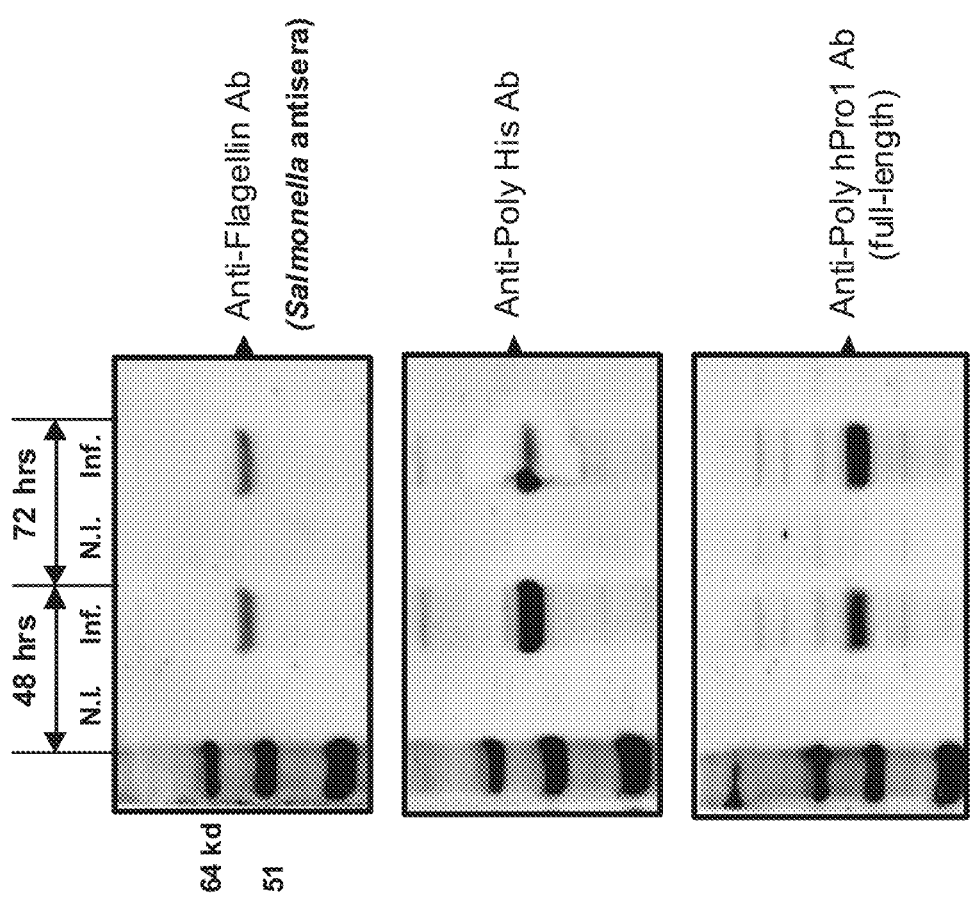
FIG. 26 is a series of western blots showing the expression of recombinant FliC-protamine (FliC-P) fusion proteins in cell lysates of FliC-P-infected or uninfected Sf9 cells.

The FliC-protamine fusion gene was then inserted into the baculoviral transfer vector pBAC (Novagen) for the expression of a histidine tag-FliC-protamine (P) fusion protein under the control of the baculovirus early promoter (FIG. 25). The resultant expression vector was confirmed by DNA sequencing. The baculoviral transfer vector and BacMagic DNA were cotransfected into insect cells to generate recombinant baculoviruses for protein expression according to the manufacturer's instruction. The estimated molecular weight of this FliC-P fusion protein is about 58 kd. To examine the fusion protein expression, the supernatants of cell lysate of FliC-P baculovirus-infected Sf9 cells or control Sf9 cells after 3 freeze-thaw cycles were subjected to Western blotting analysis using an anti-histidine antibody and anti-human protamine antibody. FIG. 26 shows the specific recognition of the recombinant FliC-P fusion protein expressed by the baculoviral expression system by anti-FliC, anti-histidine, and anti-protamine antibodies.

The recombinant proteins in the supernatants of FliC-P-baculovirus-infected Sf9 cell lysate after 3 times of freeze-thaw were purified by Ni++ chromatography according to the manufacturer's instruction (Novagen). The purified protein was dialyzed into PBS, then concentrated and stored at −70° C. The FliC-P/siA20 oligonucleotide duplex complexes were formulated via static interaction of positive charge protamine of the fusion protein and negative siRNA oligo, as described in the studies described above.

siRNA oligo duplexes were mixed with fusion proteins or control proteins (albumin) at a 6:1 molar ratio in PBS for 30 min at 4° C. After incubation, the solution with the protein/siRNA complexes was used for transfection of antigen-presenting cells (APCs) in RPMI medium 1640/10% FCS in the presence of 1 mM $MgCl_2/CaCl_2$ or 5 mM $MgCl_2$/1 mM EDTA. FliC-P/siYFP-Cy5 complexes were able to transfect about 70% of murine bone marrow-derived DCs.

Figure 27A:
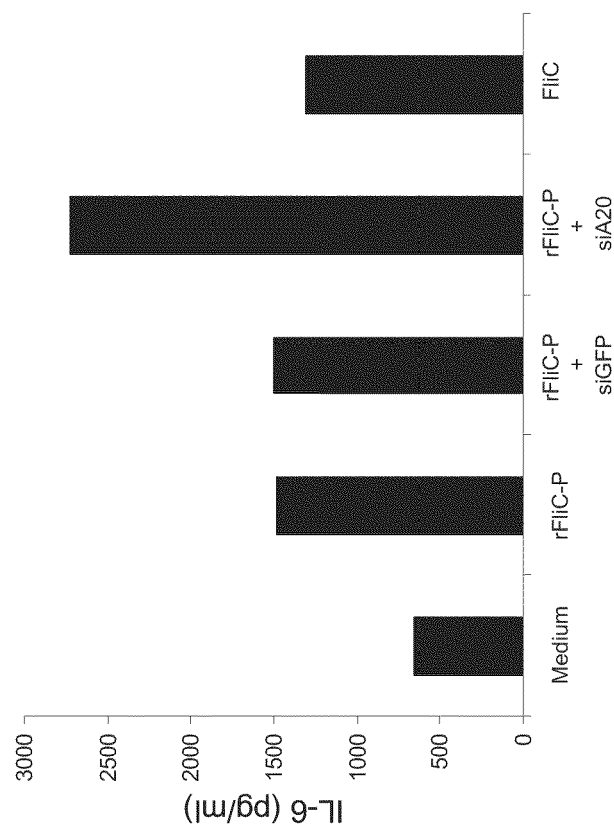
FIG. 27A shows production of TNF-α and FIG. 27B shows production of IL-6.
Figure 27B:
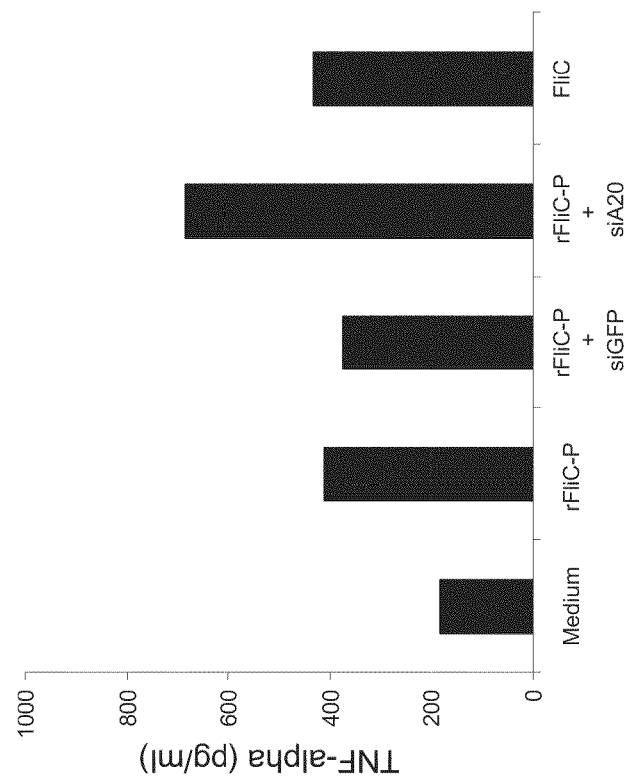

Next, it was examined whether FliC-P/siA20 complexes are more potent than FliC and other commonly used TLR agonists in enhancing the levels of proinflammatory cytokines produced by murine APCs. A20-siRNA oligo duplex was mixed with recombinant (r) FliC-P fusion protein, FliC protein, or albumin (Sigma) at a 6:1 molar ratio for 30 min. FliC proteins were isolated from *Salmonella typhimurium* strain 14028 and purchased from Axxora Inc (cat#ALX-522-058). GFP-siRNA oligo duplex was also mixed with FliC-P fusion protein as an additional control. Murine BM-derived DCs (1×106/ml) in triplicate were treated for 48 to 72 hr with FliC-P/siRNA complexes, FliC-P/siGFP complexes, FliC-P alone, or FliC alone, respectively. Culture media were collected for ELISA assays of representative cytokines (BD). FliC-P/siA20 complexes were more potent than FliC-P/siGFP complexes, FliC-P alone, and FliC alone in stimulating the production of proinflammatory cytokines by BM-DCs, indicating the superior stimulatory potency of FliC-P/siA20 complexes for the enhanced production of inflammatory cytokines TNF-α and IL-6 by APCs (FIGS. 27A and 27B, respectively). As such, compositions comprising a siRNA inhibitor of a negative immune regulator and a flagellin polypeptide linked to a protamine polypeptide are useful in methods for enhancing an immune response in a mammal in need thereof.

Example 12

Therapeutic Approaches Involving Ex Vivo Stimulation of DCs Cells Using the Compositions of the Present Invention The vaccine compositions of the present invention are useful in treating certain diseases, such as cancer. In this Example, subjects having a cancer expressing a survivin or MUC1 antigen are treated using a cell-based vaccine. The cell-based vaccine is generated by isolating and/or expanding DCs from a patient in need of treatment, transfecting the DCs with Ad-siSSF, and then reintroducing the DCs into the patient. In particular, DCs are expanded or isolated from a patient and transfected with the (i.e., transduced or transfected in vitro) with a vector expressing an inhibitor of SOCS1, a flagellin polypeptide operably linked to a secretory signal sequence, and an antigenic fusion protein comprising a dominant negative survivin mutant and MUC1.

Example 13

Therapeutic Approaches Involving In Vivo Vaccination Using the Compositions of the Present Invention In addition to using a cell-based vaccine for ex vivo immunization, the present invention also provides compositions and methods for in vivo immunization to elicit an immune response directed against an antigen in a patient. In this Example, subjects having a cancer expressing a survivin or MUC1 antigen are treated by administering to the patient a vector expressing an inhibitor of SOCS1, a flagellin polypeptide operably linked to a secretory signal sequence, and an antigenic fusion protein comprising a dominant negative survivin mutant and MUC1.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and compositions within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

Other embodiments are set forth within the following claims.

What is claimed is:

1. A composition comprising polynucleotides encoding:
   (a) a siRNA inhibitor of suppressor of cytokine signaling-1 (SOCS1) or A20; and
   (b) a flagellin polypeptide operably linked to a secretory signal sequence; wherein the polynucleotides are provided on the same or different mammalian expression vectors.

2. The composition of claim 1, wherein the siRNA inhibitor is an A20 inhibitor.

3. The composition of claim 1, further comprising a fusion of a dominant negative survivin mutant and a MUC1 fragment comprising a dominant T cell epitope.

4. The composition of claim 3, wherein the polynucleotide encoding the dominant negative survivin mutant and the MUC1 fragment has a sequence according to SEQ ID NO: 2.

5. The composition of claim 1, further comprising one or both of HCV E2 and HBsAg antigens.

6. The composition of claim 1, wherein the polynucleotide encoding the flagellin polypeptide operably linked to a secretory signal sequence has a sequence according to SEQ ID NO:3.

7. A composition comprising:
   (a) a siRNA inhibitor of a suppressor of cytokine signaling-1 (SOCS1) or A20; and (b) a flagellin polypeptide covalently linked to a protamine polypeptide, wherein the protamine polypeptide is capable of binding to the siRNA inhibitor.

8. The composition of claim 7, wherein the siRNA inhibitor is an A20 inhibitor.

9. The composition of claim 7 further comprising one or more antigens having at least one epitope, wherein the epitope is capable of eliciting an immune response in a mammal, and wherein the one or more antigens are associated with a pathogen.

10. The composition of claim 7, wherein the flagellin polypeptide covalently linked to a protamine polypeptide has a sequence according to SEQ ID NO: 174.

11. A method of generating a silenced and pulsed cell, the method comprising contacting a cell with the composition of claim 1.

12. The method of claim 11, wherein the cell is a dendritic cell.

13. The method of claim 11, wherein the step of contacting includes transduction with a viral vector, electroporation or nucleofection of plasmid DNA, or transfection of fusion proteins.

14. A method of producing an immune response against cancer cells in a mammal comprising administering to a mammal in need thereof an antigen presenting cell comprising an expression vector, wherein the expression vector comprises polynucleotides encoding:
   (a) a siRNA inhibitor of SOCS1 or A20;
   (b) a dominant negative survivin mutant and a MUC1 fragment comprising a dominant T cell epitope; and
   (c) a flagellin polypeptide operably linked to a secretory signal sequence, wherein the polynucleotides are expressed by the antigen presenting cell, thereby producing an immune response against cancer cells in the mammal.

* * * * *